US006210929B1

(12) United States Patent
Schlokat et al.

(10) Patent No.: US 6,210,929 B1
(45) Date of Patent: Apr. 3, 2001

(54) FUSION PROTEIN COMPRISING A FURIN DERIVATIVE OR A DERIVATIVE OF A FURIN ANALOGUE AND A HETEROLOGOUS SEQUENCE

(75) Inventors: Uwe Schlokat, Orth/Donau; Bernhard Fischer, Vienna; Falko-Guenter Falkner, Orth/Donau; Friedrich Dorner; Johann Eibl, both of Vienna, all of (AT)

(73) Assignee: Baxter Aktiengesellschaft, Vienna (AT)

( * ) Notice: Subject to any disclaimer, the term of this patent is extended or adjusted under 35 U.S.C. 154(b) by 0 days.

(21) Appl. No.: 08/753,247

(22) Filed: Nov. 22, 1996

(30) Foreign Application Priority Data

Nov. 24, 1995 (AT) .................................................. 1928/95

(51) Int. Cl.[7] ........................... C12N 15/62; C12N 15/70; C12P 21/06; C07K 19/00
(52) U.S. Cl. .................... 435/69.7; 435/68.1; 435/252.3; 435/252.33; 435/320.1; 435/471; 536/23.7
(58) Field of Search .................. 435/68.1, 69.1, 435/69.7, 172.3, 252.3, 252.33, 320.1, 471; 536/23.7, 23.2

(56) References Cited

U.S. PATENT DOCUMENTS

| | | | | |
|---|---|---|---|---|
| 5,108,910 | * | 4/1992 | Curtis et al. ........................ | 435/69.7 |
| 5,427,927 | * | 6/1995 | Meyer et al. ....................... | 435/69.7 |
| 5,460,950 | * | 10/1995 | Barr et al. .......................... | 435/69.1 |
| 5,532,142 | * | 7/1996 | Johnston et al. ................... | 435/69.1 |
| 5,571,697 | * | 11/1996 | Conneely et al. .................. | 435/69.7 |
| 5,618,690 | * | 4/1997 | Chaudhuri et al. ................ | 435/68.1 |
| 5,683,695 | * | 11/1997 | Shen et al. ......................... | 424/185.1 |
| 5,714,371 | * | 2/1998 | Ramanathan et al. ............. | 435/219 |
| 5,719,044 | * | 2/1998 | Shoseyov et al. .................. | 435/69.7 |
| 5,814,603 | * | 9/1998 | Oldenburg et al. ................. | 514/17 |

FOREIGN PATENT DOCUMENTS

| | | |
|---|---|---|
| 0 282 042 | 9/1988 | (EP) . |
| 0416890A1 | 3/1991 | (EP) . |
| 0565511A1 | 10/1993 | (EP) . |
| 91/06314 | 5/1991 | (WO) . |
| 92/09698 | 6/1992 | (WO) . |

OTHER PUBLICATIONS

He, M., et al., Journal of Protein Chemistry, vol. 12, "Specificity of Factor Xa in the cleavage of fusion proteins", pp. 1–10, 1993.*

Fischer et al. Febs Letters 375: 259–262 (1995).

A. Rehemtulla et al., "Regulation of PACE Propeptide–Processing Activity: Requirement for a Post–Endoplasmic Reticulum Compartment and Autoproteolytic Activation", PNAS, vol. 85, Sep. (1992), pp. 8235–8239.

W. J. M. Vand de Ven et al., "Structure and Function of Eukaryotic Proprotein Processing Enzymes of the Subtilisin Family of Serine Proteases", Critical Reviews in Oncogenesis, vol. 4, No. 2, (1993), pp. 115–136.

M. Hosaka et al., "Arg–X–Lys/Arg–Arg Motif as a Signal for Precursor Cleavage Catalyzed by Furin within the Constitutive Secretory Pathway", The Journal of Biological Chemistry, vol. 266, No. 19 Jul (1991), pp. 12127–12130.

A. J. M. Roebroek et al, "Characterization of Human C–fes/fps Reveals a New Transcription Unit (fur) in the Immediately Upstream Region of the Proto–Oncogene", Molec. Biol. Rep., vol. 11, (1986), pp. 117–125.

(List continued on next page.)

*Primary Examiner*—Ponnathapu Achutamurthy
*Assistant Examiner*—William W. Moore
(74) *Attorney, Agent, or Firm*—Foley & Lardner

(57) ABSTRACT

Fusion proteins of an optionally C-terminally deleted furin derivative, or of a derivative of a furin analogue, and a heterologous sequence, methods of preparing the same and methods of recovering proproteins from proteins by using the proproteins according to the invention are described.

22 Claims, 16 Drawing Sheets

OTHER PUBLICATIONS

H. D. Klenk et al., "Activation Cleavage of Viral Spike Proteins by Host Proteases", Cellular Receptors for Animal Viruses, (1994), pp. 241–280.

D. Baruch et al., "Von Willebrand Factor and Platelet Function", Bailliere's Clinical Haematology vol. 2, No. 3, Jul. (1989), pp. 627–673.

T. Clackson et al., "General Applications of PCR to Gene Cloning and Manipulation", PCR: A Practical Approach, (1991), pp. 187–214.

B. Fischer et al., "Structural Analysis of Recombinant von Willebrand Factor: Identification of Hetero– and Hom–dimers", FEBS Letters, vol. 351, (1994), pp. 345–348.

G. R. MacGregor et al., "Construction of Plasmids that Express E. coli β–Galactosidase in Mammalian Cells", vol. 17, No. 6, (1989), p. 2365.

F. Lee et al., "Glucocorticoids Regulate Expression of Dihydrofolate Reductase cDNA in Mouse Mammary Tumour Virus Chimaeric Plasmids", Nature, vol. 294, Nov. (1981), pp. 228–232.

C. Yanisch–Perron et al., "Improved M13 Phage Cloning Vectors and Host Strains: Nucleotide Sequences of the M13mp18 and pUC19 Vectors", Gene, vol. 33, (1989), pp. 103–119.

U. K. Laemmli et al., "Cleavage of Structural Proteins During the Assembly of the Head of Bacteriophage T4", Nature, vol. 227, Aug. (1970), pp. 680–685.

D. L. Wolf et al., "Design of Constructs for the Expression of Biologically Active Recombinant Human Factors X and Xa", The Journal of Biological Chemistry, vol. 266, No. 21, Jul. (1991), pp. 13726–13730.

D. S. Fair et al., "Human Hepatoma Cells Secrete Single Chain Factor X, Prothrombin, and Anti–thrombin III", Blood, vol. 64, No. 1, Jul. (1984), pp. 194–204.

A. J. M. Roebroek et al., "Evolutionary Conserved Close Linkage of the C–fes/fps Proto–Oncogene and Genetic Sequences Encoding a Receptor–Like Protein", The EMBO Journal, vol. 5, No. 9, (1986) pp. 2197–2202.

P. J. Barr et al., "cDNA and Gene Structure for a Human Subtilisin–Like Protease with Cleavage Specificity for Paired Basic Amino Acid Residues", DNA and Cell Biology, vol. 10, No. 5, (1991), pp. 319–328.

Ans M. W. Van den Ouweland et al., "Nucleotide Sequence Analysis of the Human fur Gene", Nucleic Acids Research, vol. 17, No. 17, (1989), pp. 7101–7102.

Ans M. W. Van den Ouweland et al., "Structural Homology Between the Human fur Gene Product and the Subtilisin––Like Protease Encoded by Yeast KEX2", Nucleic Acids Research, vol. 18, No. 3, Jan. (1990), p. 664.

S. P. Smeekens et al., "Identification of a Human Insulinoma cDNA Encoding a Novel Mammalian Protein Structurally Related to the Yeast Dibasic Processing Protease Kex2", The Journal of Biological Chemistry, vol. 265, No. 6, (1990), pp. 2997–3000.

S. P. Smeekens et al., "Identification of a cDNA Encoding a Second Putative Prohormone Convertase Related to PC2 in AtT20 Cells and Islets of Langerhans", Proc. Natl. Acad. Sci. USA, vol. 88, Jan. (1991), pp. 340–344.

M. C. Kiefer et al., "Idntification of a Second Human Subtilisin–Like Protease Gene in the fes/fps Region of Chromosome 15", DNA and Cell Biology, vol. 10, No. 10, (1991), pp. 757–769.

K. Nakayama et al., "Identification of the Fourth Member of the Mammalian Endoprotease Family Homologous to to the Yeast Kex2 Protease", The Journal of Biological Chemistry, vol. 267, No. 9 Mar. (1992), pp. 5897–5900.

K. Hatsuzawa et al., "Structure and Espression of Mouse Furin, a Yeast Kex2–Related Protease", The Journal of Biological Chemistry, vol. 265, No. 36, Dec. (1990), pp. 22075–22078.

P. A. Bresnahan et al., "Human fur Gene Encodes a Yeast KEX2–Like Endoprotease That Cleaves Pro–β–NGF In Vivo", The Journal of Cell Biology, vol. 111, No. 6, Pt. 2, Dec. (1990), pp. 2851–2859.

R. J. Wise et al., "Expression of a Human Proprotein Processing Enzyme: Correct Cleavage of the Von Willebrand Factor Precursor at a Paired Basic Amino Acid Site", Proc. Natl. Acad. Sci. USA., vol. 87, Dec. (1990), pp. 9378–9382.

G. Vidricaire et al., "Characterization of a Secreted Form of Human Furin Endoprotease", Biochem. Biophys. Research Comm., vol. 195, No. 2, Sep. (1993), pp. 1011–1018.

M. Vey et al., "Maturation of the Trans–Golgi Network Protease Furin: Compartmentalization of Propeptide Removal Substrate Cleavage, and COOH–Terminal Truncation", The Journal of Cell Biology, vol. 127, No. 6, Part 2, Dec. (1994), pp. 1829–1842.

R. Leduct et al., "Activation of Human Furin Precursor Processing Endoprotease Occurs by an Intramolecular Autoproteolytic Cleavage", The Journal of Biological Chemistry, vol. 267, No. 20, Jul. (1992), pp. 14304–14308.

S. S. Molloy et al., "Human Furin Is a Calcium–Dependent Serine Endoprotease That Recognizes the Sequences Arg–X–X–Arg and Efficiently Cleaves Anthrax Toxin Protective Antigen", The Journal of Biological Chemistry, vol. 267, No. 23, Aug. (1992), pp. 16396–16402.

L. C. Wasley et al., "Pace/Furin Can Process the Vitamin K–Dependent Pro–Factor IX Precursor within the Secretory Pathway", The Journal of Biological Chemistry, vol. 268, No. 12, Apr. (1993), pp. 8458–8465.

A. Rehemtulla et al., "Preferred Sequence Requirements for Cleavage of Pro–Von Willebrand Factor by Propeptide–Processing Enzymes", Blood, vol. 79, No. 9, May (1992), pp. 2349–2355.

K. Hatsuzawa et al., Purification and Charcterization of Furin, a Kex2–Like Processing Endoprotease, Produced in Chinese Hamster Ovary Cells, The Journal of Biology Chemistry, vol. 267, No. 3, Aug. (1992), pp. 16094–16099.

K. Hatsuzawa et al., "Molecular and Enzymatic Properties of Furin, a Kex2–Like Endoprotease Involved in Precursor Cleavage at Arg–X–Lys/Arg–Arg Sites", J. Biochem., vol. 111, (1992), pp. 296–301.

J. W. M. Creemerst et al., "Modulation of Furin–Mediated Proprotein Processing Activity by Site–Directed Mutagenesis", The Journal of Biological Chemistry, vol. 268, No. 29, Oct. (1993), pp. 21826–21834.

C. L. Verweij et al., "Full–Length Von Willebrand Factor (vWF) cDNA Encodes a Highly Repetitive Protein Considerably larger Than the Mature vWF Subunit", The EMBO Journal, vol. 5, No. 8, (1986) pp. 1839–1847.

W. J. M Van de Ven et al., "Furin is a Subtilisin–Like Proprotein Processing Enzyme in Higher Eukaryotes", Molecular Biology Reports, vol. 14, (1990), pp. 265–275.

E. Decroly et al., "The Convertases Furin and PC1 Can Both Cleave the Human Immunodeficiency Virus (HIV)–1 Envelope Glycoprotein gp160 into gp120 (HIV–I SU) and gp41 (HIV–I TM)", The Journal of Biological Chemistry, vol. 269, No. 16, Apr. (1994), pp. 12240–12247.

A. Stieneke–Groeber et al., "Influenza Virus Hemagglutininwith Multibasic Cleavage Site is Activated by Furin, a Subtilinsin–Like Endoprotease", The EMBO Journal, vol. 11, No. 7, (1992), pp. 2407–2414.

P. J. Barr., "Mammalian Subtilisins: The Long–Sought Dibasic Processing Endoproteases", Cell, vol. 66, Jul (1991), pp. 1–3.

K. R. Klimpel et al., "Anthrax Toxin Protective Antigen is Activated by a Cell Surface Protease with the Sequence Specificity and Catalytic Properties of Furin", Proc. Natl. Acad. Sci. USA. vol. 89, Nov. (1992), pp. 10277–10281.

N, Tsuneoka et al., "Evidence for Involvement of Furin in Cleavage and Activation of Diptheria Toxin", The Journal of Biological Chemistry, vol. 268, No. 35, Dec. (1993), pp. 26461–26465.

K. Oda et al., "Proteolytic Cleavages of Proalbumin and Complement Pro–C3 in Vitro by a Truncated Soluble Form of Furin, a Mammalian Homologue of the Yeast Kex2 Protease", Biochem. Biophys. Research Comm., vol. 189, No. 3, (1992), pp. 1351–1361.

J. A. Bristol et al., Profactor IX: The Propeptide Inhibits Binding to Membrane Surfaces and Activation by Factor XIa, Biochemistry, vol. 33, (1994), pp. 14136–14143.

J. W. M. Creemers., "Structural and Functional Characterization of the Mammalian Proprotein Processing Enzyme Furin", (1994), pp. 1–60.

S. S. Molloy et al., "Intracellular Trafficking and Activation of the Furin Proprotein Convertase Localization; to the TGN and Recycling from the Cell Surface", The EMBO Journal, vol. 13, No. 1, (1994), pp. 18–33.

D. A. Bravo et al., "Accurate and Efficient Cleavage of the Human Insulin Proreceptor by the Human Proprotein–Processing Protease Furin", The Journal of Biological Chemistry, vol. 269, No. 41, Oct. (1994), pp. 25830–25837.

G. I. Evan et al., "isolation of Monoclonal Antibodies Specific for Human c–myc Proto–Oncogene Product", Molecular and Cellular Biology, vol. 5, No. 12, Dec. (1985), pp. 3610–3616.

H. L. P. Van Duijnhoven et al., "Development and Characterization of a Panel of Monoclonal Anti–bodies Against the Novel Subtilisin–Like Proprotein Processing Enzyme Furin", Hybridoma, vol. 11, No. 1, (1992), pp. 71–86.

E. R. LaVallie et al., "Cloning and Functional Expression of a cDNA Encoding the Catalytic Subunit of Bovine Enterokinase", The Journal of Biological Chemistry, vol. 268, No. 31, Nov. (1993), pp. 23311–23317.

D. J. Matthews et al., "A Survey of Furin Substrate Specificity Using Substrate Phage Display", Protein Science, vol. 3, (1994), pp. 1197–1205.

R. Janknecht et al., "Rapid and Efficient Purification of Native Histidine–Tagged Protein Expressed by Recombinant Vaccinia Virus", Proc. Natl. Acad. Sci. USA, vol. 88, Oct. (1991), pp. 8972–8976.

A. Hoffman et al., "Purification of His–Tagged Proteins in Non–Denaturing Conditions Suggests a Convenient Method for Protein Interaction Studies", Nucleic Acids Research, vol. 19, No. 22, Aug. (1991), pp. 6337–6338.

G. Urlaub et al., "Isolation of Chinese Hamster Cell Mutants Deficient in Dihydrofolate Reductase Activity", Proc. Natl. Acad. Sci. USA, vol. 77, No. 7, Jul. (1980), pp. 4216–4220.

* cited by examiner

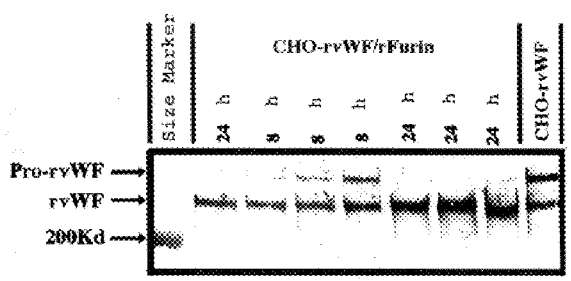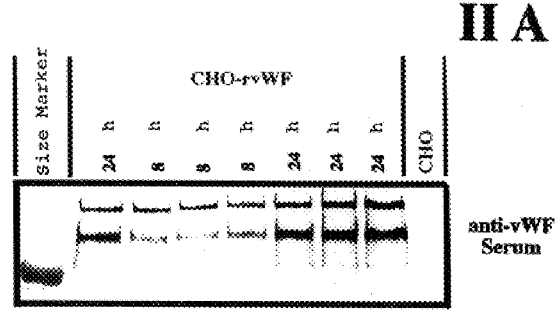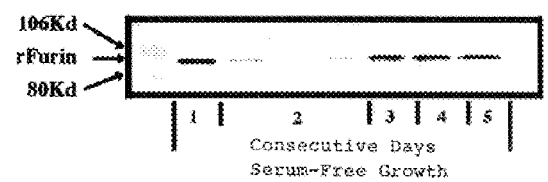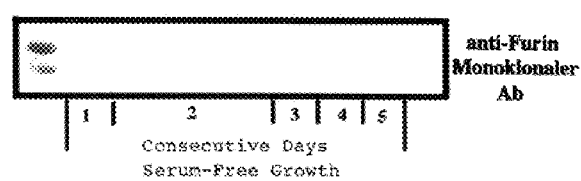
FIG. 2

FIG. 4-A-1

```
(-107)
         1
Frame 1  Met Glu Leu Arg Pro Trp Leu Leu Val Val Ala Ala Thr Gly Thr Leu Val Leu
         ATG GAG CTG AGG CCC TGG CTA TTG GTG GTA GCA GCA ACA GGA ACC TTG GTC CTG
                           18              27              36              45              54

Leu Ala Ala Asp Ala Gln Gly Gln Lys Val Phe Thr Asn Thr Trp Ala Val Arg Ile Pro Gly
         CTA GCA GCT GAT GCT CAG GGC CAG AAG GTC TTC ACC AAC ACG TGG GCT GTG CGC ATC CCT GGA
          66              75              84              93             102             111             120

Gly Pro Ala Val Ala Asn Ser Val Ala Arg Lys His Gly Phe Leu Asn Leu Gly Gln Ile Phe
         GGC CCA GCG GTG GCC AAC AGT GTG GCA CGG AAG CAT GGG TTC CTC AAC CTG GGC CAG ATC TTC
         129             138             147             156             165             174             183

Gly Asp Tyr Tyr His Phe Trp His Arg Gly Val Thr Lys Arg Ser Leu Ser Pro His Arg Pro
         GGG GAC TAT TAC CAC TTC TGG CAT CGA GGA GTG ACG AAG CGG TCC CTG TCG CCT CAC CGC CCG
         192             201             210             219             228             237             246

Arg His Ser Arg Leu Gln Arg Glu Pro Gln Val Gln Trp Leu Glu Gln Gln Val Ala Lys Arg
         CGG CAC AGC CGG CTG CAG AGG GAG CCT CAA GTA CAG TGG CTG GAA CAG CAG GTG GCA AAG CGA
         255             264             273             282             291             300             309
```

FIG. 4-A-2

```
        (-1) (+1)
        107  108
Arg Thr Lys Arg Asp Val Tyr Gln Glu Pro Thr Asp Pro Lys Phe Pro Gln Gln Trp Tyr Leu
CGG ACT AAA CGG GAC GTG TAC CAG GAG CCC ACA GAC CCC AAG TTT CCT CAG CAG TGG TAC CTG
        318             327             336             345             354             363             372

Ser Gly Val Thr Gln Arg Asp Leu Asn Val Lys Ala Ala Trp Ala Gln Gly Tyr Thr Gly His
TCT GGT GTC ACT CAG CGG GAC CTG AAT GTG AAG GCG GCC TGG GCG CAG GGC TAC ACA GGG CAC
        381             390             399             408             417             426             435

Gly Ile Val Val Ser Ile Leu Asp Asp Gly Ile Glu Lys Asn His Pro Asp Leu Ala Gly Asn
GGC ATT GTG GTC TCC ATT CTG GAC GAT GGC ATC GAG AAG AAC CAC CCG GAC TTG GCA GGC AAT
        444             453             462             471             480             489             498

Tyr Asp Pro Gly Ala Ser Phe Asp Val Asn Asp Gln Asp Pro Gln Pro Arg Tyr Thr
TAT GAT CCT GGG GCC AGT TTT GAT GTC AAT GAC CAG GAC CCT CAG CCT CGG TAC ACA
        507             516             525             534             543             552             561

Gln Met Asn Asp Asn Arg His Gly Thr Arg Cys Ala Gly Glu Val Ala Ala Val Ala Asn Asn
CAG ATG AAT GAC AAC AGG CAC GGA ACA CGG TGT GCG GGG GAA GTG GCT GCG GTG GCC AAC AAC
        570             579             588             597             606             615             624

Gly Val Cys Gly Val Gly Val Ala Tyr Asn Ala Arg Ile Gly Gly Val Arg Met Leu Asp Gly
GGT GTC TGT GGT GTA GGT GTG GCC TAC AAC GCC CGC ATT GGA GGG GTG CGC ATG CTG GAT GGC
        633             642             651             660             669             678             687
```

FIG. 4-B-1

```
Glu Val Thr Asp Ala Val Glu Ala Arg Ser Leu Asn Gly Leu Asn Pro Asn His Ile Tyr
GAG GTG ACA GAT GCA GTG GAG GCA CGC TCG CTG AAC GGC CTG AAC CCC AAC CAC ATC TAC
        696                     705                     714                     723                     732                     741        750

Ser Ala Ser Trp Gly Pro Glu Asp Asp Gly Lys Thr Val Asp Gly Pro Ala Arg Leu Ala Glu
AGT GCC AGC TGG GGC CCC GAG GAT GAC GGC AAG ACA GTG GAT GGG CCA GCC CGC CTC GCC GAG
        759                     768                     777                     786                     795                     804        813

Glu Ala Phe Phe Arg Gly Val Ser Gln Gly Arg Gly Gly Leu Gly Ser Ile Phe Val Trp Ala
GAG GCC TTC TTC CGT GGG GTT AGC CAG GGG CGA GGG GGG CTG GGC TCC ATC TTT GTC TGG GCC
        822                     831                     840                     849                     858                     867        876

Ser Gly Asn Gly Gly Arg Glu His Asp Ser Cys Asn Cys Asp Gly Tyr Thr Asn Ser Ile Tyr
TCG GGG AAC GGG GGC CGG GAA CAT GAC AGC AGC TGC AAC TGC GAC GGC TAC ACC AAC AGT ATC TAC
        885                     894                     903                     912                     921                     930        939

Thr Leu Ser Ile Ser Ser Ala Thr Gln Phe Gly Asn Val Pro Trp Tyr Ser Glu Ala Cys Ser
ACG CTG TCC ATC AGC AGC GCC ACG CAG TTT GGC AAC GTG CCG TGG TAC AGC GAG GCC TGC TCG
        948                     957                     966                     975                     984                     993        1002

Ser Thr Leu Ala Thr Thr Tyr Ser Ser Gly Asn Gln Asn Glu Lys Gln Ile Val Thr Thr Asp
TCC ACA CTG GCC ACC ACC TAC AGC AGT GGC AAC CAG AAT GAG AAG CAG ATC GTG ACG ACT GAC
        1011                    1020                    1029                    1038                    1047                    1056       1065

Leu Arg Gln Lys Cys Thr Glu Ser His Thr Gly Thr Ser Ala Pro Leu Ala Ala Gly
TTG CGG CAG AAG TGC ACG GAG TCT CAC ACG GGC ACC TCA GCC CCC TTA GCA GCC GGC
        1074                    1083                    1092                    1101                    1110                    1119  1128
```

FIG. 4-B-2

```
Ile Ile Ala Leu Thr Leu Glu Ala Asn Lys Asn Leu Thr Trp Arg Asp Met Gln His Leu Val
ATC ATT GCT CTC ACC CTG GAG GCC AAT AAG AAC CTC ACA TGG CGG GAC ATG CAA CAC CTG GTG
1137                    1146                    1155                    1164                    1173                    1182                    1191

Val Gln Thr Ser Lys Pro Ala His Leu Asn Ala Asn Asp Trp Ala Thr Asn Gly Val Gly Arg
GTA CAG ACC TCG AAG CCA GCC CAC CTC AAT GCC AAC GAC TGG GCC ACC AAT GGT GTG GGC CGG
        1200                    1209                    1218                    1227                    1236                    1245                    1254
                                                                        (+323)
                                                                         430

Lys Val Ser His Ser Tyr Gly Leu Leu Asp Ala Gly Ala Met Val Ala Leu Ala Gln
AAA GTG AGC CAC TCA TAT GGC CTT TTG GAC GCA GGC GCC ATG GTG GCC CTG GCC CAG
        1263                    1272                    1281                    1290                    1299                    1308                    1317

Asn Trp Thr Thr Val Ala Pro Gln Arg Lys Cys Ile Ile Asp Ile Leu Thr Glu Pro Lys Asp
AAT TGG ACC ACA GTG GCC CCC CAG CGG AAG TGC ATC ATC GAC ATC CTC ACC GAG CCC AAA GAC
        1326                    1335                    1344                    1353                    1362                    1371                    1380

Ile Gly Lys Arg Leu Glu Val Arg Lys Thr Val Thr Ala Cys Leu Gly Glu Pro Asn His Ile
ATC GGG AAA CGG CTC GAG GTG CGG AAG ACC GTG ACC GCG TGC CTG GGC GAG CCC AAC CAC ATC
        1389                    1398                    1407                    1416                    1425                    1434                    1443

Thr Arg Leu Glu His Ala Gln Ala Arg Leu Thr Leu Ser Tyr Asn Arg Arg Gly Asp Leu Ala
ACT CGG CTG GAG CAC GCT CAG GCG CGG CTC ACC CTG TCC TAT AAT CGC CGT GGC GAC CTG GCC
        1452                    1461                    1470                    1479                    1488                    1497                    1506
```

FIG. 4-C-1

```
Ile His Leu Val Ser Pro Met Gly Thr Arg Ser Thr Leu Leu Ala Ala Arg Pro His Asp Tyr
ATC CAC CTG GTC AGC CCC ATG GGC ACC CGC TCC ACC CTG GCA GCC AGG CCA CAT GAC TAC
    1515              1524              1533              1542              1551              1560              1569

Ser Ala Asp Gly Phe Asn Asp Trp Ala Phe Met Thr Thr His Ser Trp Asp Glu Asp Pro Ser
TCC GCA GAT GGG TTT AAT GAC TGG GCC TTC ATG ACA ACT CAT TCC TGG GAT GAG GAT CCC TCT
    1578              1587              1596              1605              1614              1623              1632

Gly Glu Trp Val Leu Glu Ile Glu Asn Thr Ser Glu Ala Asn Tyr Gly Thr Leu Thr Lys
GGC GAG TGG GTC CTA GAG ATT GAA AAC ACC AGC GAA GCC AAC TAT GGG ACG CTG ACC AAG
    1641              1650              1659              1668              1677              1686              1695

(+462)(+463)                                                    (+473)                     (+478)
           569  570                                                        580                       585
Phe Thr Leu Val Leu Tyr Gly Thr Ala Pro Glu Gly Leu Pro Val Pro Pro Glu Ser Ser Gly
TTC ACC CTC GTA CTC TAT GGC ACC GCC CCT GAG GGG CTG CCC GTA CCT CCA GAA AGC AGT GGC
    1704              1713              1722              1731              1740              1749              1758

Cys Lys Thr Leu Thr Ser Ser Gln Ala Cys Val Val Cys Glu Glu Gly Phe Ser Leu His Gln
TGC AAG ACC CTC ACG TCC AGT CAG GCC TGT GTG TGC GAG GAA GGC TTC TCC CTG CAC CAG
    1767              1776              1785              1794              1803              1812              1821

Lys Ser Cys Val Gln His Cys Pro Pro Gly Phe Ala Pro Gln Val Leu Asp Thr His Tyr Ser
AAG AGC TGT GTC CAG CAC TGC CCT CCA GGC TTC GCC CCC CAA GTC CTC GAT ACG CAC TAT AGC
    1830              1839              1848              1857              1866              1875              1884

Thr Glu Asn Asp Val Glu Thr Ile Arg Ala Ser Val Cys Ala Pro Cys His Ala Ser Cys Ala
ACC GAG AAT GAC GTG GAG ACC ATC CGG GCC AGC GTC TGC GCC CCC TGC CAC GCC TCA TGT GCC
    1893              1902              1911              1920              1929              1938              1947
```

FIG. 4-C-2

```
                                                  (+553)
                                                   660
Thr Cys Gln Gly Pro Ala Leu Thr Asp Cys Leu Ser Cys Pro Ser His Ala Ser Leu Asp Pro
ACA TGC CAG GGG CCG GCC CTG ACA GAC TGC CTC AGC TGC CCC AGC CAC GCC TCC TTG GAC CCT
            1956            1965            1974            1983            1992            2001            2010

Val Glu Gln Thr Cys Ser Arg Gln Ser Ser Arg Glu Ser Pro Pro Gln Gln Pro
GTG GAG CAG ACT TGC TCC CGG CAA AGC AGC CGA GAG TCC CCG CAG CAG CAG CCA
            2019            2028            2037            2046            2055            2064            2073

(+588)                                            (+600)  (+602)
               695                                               707    709
Pro Arg Leu Pro Pro Glu Val Glu Ala Gly Gln Arg Leu Arg Ala Gly Leu Leu Pro Ser His
CCT CGG CTG CCC CCG GAG GTG GAG GCG GGG CAA CGG CTG CGG GCA GGG CTG CTG CCC TCA CAC
            2082            2091            2100            2109            2118            2127            2136

(+613)
               720
Leu Pro Glu Val Val Ala Gly Leu Ser Cys Ala Phe Ile Val Leu Val Phe Val Thr Val Phe
CTG CCT GAG GTG GTG GCC GGC CTC AGC TGC GCC TTC ATC GTG CTG GTC TTC GTC ACT GTC TTC
            2145            2154            2163            2172            2181            2190            2199

Leu Val Leu Gln Leu Arg Ser Gly Phe Ser Phe Arg Gly Val Lys Val Tyr Thr Met Asp Arg
CTG GTC CTG CAG CTG CGC TCT GGC TTT AGT TTT CGG GGG GTG AAG GTG TAC ACC ATG GAC CGT
```

```
     2208      2217      2226      2235      2244      2253      2262
Gly Leu Ile Ser Tyr Lys Gly Leu Pro Pro Glu Ala Trp Gln Glu Glu Cys Pro Ser Asp Ser
GGC CTC ATC TCC TAC AAG GGG CTG CCC CCT GAA GCC TGG CAG GAG GAG TGC CCG TCT GAC TCA
     2271      2280      2289      2298      2307      2316      2325

(+687)
                                                                794
Glu Glu Asp Glu Gly Arg Gly Glu Arg Thr Ala Phe Ile Lys Asp Gln Ser Ala Leu TER
GAA GAG GAC GAG GGC CGG GAG AGG ACC GCC TTT ATC AAA GAC CAG AGC GCC CTC TGA
     2334      2343      2352      2361      2370      2379
```

FIG. 4-D t = Incubation at 37°C, stated in hours

FUSION PROTEIN COMPRISING A FURIN DERIVATIVE OR A DERIVATIVE OF A FURIN ANALOGUE AND A HETEROLOGOUS SEQUENCE

The invention relates to a new fusion protein, derived from furin or a furin analog, as well as to a method of preparing proteins from proproteins by means of the fusion protein, in particular of von Willebrand factor from pro-von Willebrand factor.

In addition to PACE4, PC1/PC3, PC2, PC4 and PC5/PC6, furin, also termed PACE, belongs to the group of the subtilisin-like serine proteases, which play an important role in the cleavage of proproteins, especially in the secretory synthesis (Van de Ven et al., Crit. Rev. Oncogen., 4:115–136, 1993). Proproteins are post-translationally, intracellularily processed to their mature form by the endogenous protease in the Golgi apparatus. The protease cleavage site comprises a recognition sequence which is characterized by the amino acid sequence Arg-X-Lys/Arg-Arg. The protease furin cleaves proproteins specifically after this consensus sequence (Hosaka et al., J. Biol. Chem. 266:12127–12130, 1991).

The DNA and amino acid sequence of human and murine furin, as well as further proteins with subtilisin-like protease function have been clarified (Roebroek et al., Mol. Biol. Rep. 11: 117–125, 1986, Roebroek et al., EMBO J. 5:2197–2202, 1986, Barr et al., DNA Cell Biol. 10:319–328, 1991, Van den Ouweland et al., Nucleic Acids Res. 17:7101–7102, 1989, Van den Ouweland et al., Nucleic Acids Res. 18:664, 1990, Smeekens et al., 1990, J. Biol. Chem. 265:2997–3000; Smeekens et al., 1991, Proc. Natl. Acad. Sci. USA. 88; 340–344; Kiefer et al., 1991, DNA Cell Bio. 10: 757; Nakayama et al., 1992, J. Bio. Chem. 267:5897–5900, Hatsuzawa et al., 1990. J. Biol. Chem. 265: 22075–22078). The human fur-gene encodes a protein consisting of 794 amino acids, certain functions being allocatable to individual characteristic regions: a catalytic center, a middle domain, a cystein-rich region, a transmembrane and a cytoplasmatic domain (Van de Ven et al., Crit. Rev. Oncogen., 4:115–136, 1993).

Intact furin is incorporated into the membrane system of the Golgi apparatus and there it is functionally active (Bresnahan et al., J. Cell Biol. 111:2851–2859, 1990). A truncated form of the over-expressed native furin of 75–80 kD could be detected in the cell supernatant as secreted protein (Wise et al., Proc. Natl. Acad. Sci. USA 87: 9378–9382, 1990). This naturally secreted furin is known as "shed furin" (Vidricaire et al., Biochem. Biophys. Res. Comm. 195:1011–1018, 1993) and is cleaved N-terminally of the transmembrane portion (Vey et al., J. Cell Biol. 127:1829–1842, 1994).

Furin truncated by genetical engineering, in which the encoding part of the transmembrane and cytoplasmatic domains has been deleted, can also be expressed and secreted correspondingly. Such N-terminal deletions have been described for amino acids Δ714–794 (Leduc et al., J. Biol. Chem. 267:14304–14308, 1992, Molloy et al., J. Biol. Chem. 267:16396–16402, 1992) and for amino acids Δ716–794 ("Sol-PACE") (Wasley et al., 1993. J. Biol. Chem. 268:8458–8465, Rehemtulla et al., Blood 79:2349–2355, 1992) and for amino acids Δ705–794 (Hatsuzawa et al., 1992. J. Biol. Chem. 267:16094–16099).

Furin mutants additionally comprising a deletion of the cystein-rich region have also been described (Hatsuzawa et al., 1992. J. Biochem. 101:296–301, Creemers et al., 1993. J. Biol. Chem. 268:21826–21834).

The endoproteolytic activity of furin and its selectivity for basic amino acids has first been determined in experiments with pro-von Willebrand factor (pro-vWF). Pro-vWF consists of a propolypeptide with 741 amino acids and mature von Willebrand factor (vWF) with 2050 amino acids (Verweij et al., EMBO J. 5:1839–1847, 1986). The liberation of mature vWF from pro-vWF results from a proteolytic cleavage after Arg763. Transfection of pro-vWF cDNA in eukaryotic expression vectors results in the production of equimolar amounts of the 360 kD pro-vWF and of the 260 kD mature vWF in the cell culture supernatant. vWF is probably processed into its mature form in transfected cells, by endogenously occurring furin (Wise et al., Proc. Natl. Acad. Sci. USA 87:9378–9382, 1990, Van de Ven et al., Mol. Biol. Rep. 14:265–275, 1990).

Among the further proproteins which are cleaved by furin or by subtilisin-like enzymes, respectively, are a series of hormones and growth factors (e.g., proactivin A, hepatocyte-growth factor), plasma proteins (albumin, factor VII, factor IX, factor X), receptors (insulin pro-receptor), viral proteins (e.g. HIV-1 gp160, influenza virus haemagglutinin) as well as bacterial proteins (diphteria toxin, anthrax toxin) (Decroly et al., J. Biol. Chem. 269:12240–12247, 1994, Stieneke-Gröber et al., EMBO J. 11:2407–2414, 1992, Barr, Cell 66:1–3, 1991, Wasley et al., J. Biol. Chem. 268:8458–8465, 1993, Klimpel et al., Proc. Natl. Acad. Sci. USA 89:10277–10281, 1992, Tsuneoka et al., J. Biol. Chem. 268:26461–26465, 1993, Bresnahan et al., J. Cell. Biol. 111:2851–2859, 1990, Hosaka et al., J. Biol. Chem. 266:12127–12130, 1991, Vey et al., J. Cell. Biol. 127:1829–1842, 1994).

By co-expression of the nucleic acid sequences encoding intact furin and a proprotein in eukaryotic cell cultures, an increased processing of the proproteins has been achieved in vivo. This has been demonstrated, e.g., for pro-factor IX (Wasley et al., J. Biol. Chem. 268:8458–8465, 1993) and for pro-vWF (WO 91/06314, Van de Ven et al., Mol. Bio. Rep. 14:265–275, 1990, Rehemtulla et al., Blood 79:2349–2355, 1992).

Beside the co-expression of intact furin with proproteins, there have also been attempts to express truncated furin together with proproteins. Deleted furin is enzymatically active when co-expressed in vivo and is secreted; the enzymatic activity of such deletion mutants could be detected inter alia in the processing of pro-factor IX (Wasley et al., J. Biol. Chem. 268:8458–8465, 1993) and of pro-vWF (Rehemtulla et al., Blood 79: 2349–2355, 1992). Co-expression experiments with furin deletion mutants have shown that the transmembrane and the cytoplasmatic part of the protein are not essential to the catalytic function (Rehemtulla et al., Proc. Natl. Acad. Sci. USA 89: 8235–8239, 1992).

WO 91/06314 discloses the recombinant expression of furin in prokaryotic and eukaryotic cells, the preparation of furin fusion proteins, deletion mutants and fragments, the purification of recombinantly prepared furin, as well as the possible use of purified furin for the processing of proproteins in vitro in general.

WO 92/09698 describes the expression of PACE (furin), the co-expression with inactive precursors of proteins, such as, e.g., pro-vWF, as well as the preparation of fusion proteins. To enrich PACE it has been suggested therein to isolate PACE capable of secretion, by conventional methods.

Stieneke-Gröber et al. (EMBO J. 11:2407–2414, 1992) describe the in vitro cleavage of influenza virus HA protein by means of purified furin. Decroly et al. (J. Biol. Chem.

269:12240–12247, 1994) describe the in vitro cleavage of HIV gp160 by means of furin.

In experiments with C-terminally shortened furin, the cleavage of pro-albumin and complement Pro-C3 (Oda et al., Biochem. Biophys. Res. Commun. 189:1353–1361, 1992), anthrax toxin (Klimpel et al., Proc. Nastl. Acad. Sci. USA 89:10277–10281, 1992), diphtheria toxin (Tsuneoka et al., J. Biol. Chem. 268: 26461–26465, 1993) and pro-factor IX (Wasley et al., J. Biol. Chem. 268:8458–8468, 1993, Bristol et al., Biochemistry 33:14136–14143, 1994) has been carried out successfully in vitro.

So far, it has not been possible to demonstrate in vitro processing of pro-vWF by means of furin. Rehemtulla et al. (Blood 79:2349–2355, 1992, and Proc. Natl. Acad. Sci. USA 89:8235–8239, 1992) describe that by mixing supernatants of cells transfected with pro-vWF and deleted furin ("PACE SOL"), respectively, pro-vWF is not processed to vWF. Contrary therto, both synthetic substrates (Rehemtulla et al., Proc. Natl. Acad. Sci. USA 89:8235–8239, 1992) and also pro-factor IX (Bristol et al., Biochemistry 33:14136–14143, 1994) could be cleaved in vitro by means of purified "PACE SOL". For pro-vWF it has, furthermore, repeatedly been claimed that it is not processed into its mature form in vitro by truncated furin (Rehemtulla et al., Proc. Natl. Acad. Sci. USA 89:8235–8239, 1992, and Blood 79:2349–2355, 1992), whereas factor IX is cleaved under analogous conditions (Wasley et al., 1993. J. Biol. Chem. 268:8458–8465).

To obtain high yields of completely processed proteins in the recombinant preparation of proteins from proproteins, it has been considered necessary according to the prior art to express and isolate a sufficiently large amount of furin, or to co-express proprotein and furin.

In the recombinant expression of furin alone, but also in the co-expression of furin with a proprotein on a large scale in cell cultures, however, the problem arises that a high expression of the protease is toxic to the cells (Creemers 1994), whereby only a small yield of furin and of mature protein is possible. Thus, it could be demonstrated in co-expression studies that cell clones which highly express furin and efficiently process the proprotein, grow to much lower cell densities as compared to cells which do not express furin. This results in a poorer total yield of processed protein. To obtain a high yield of mature protein, thus a very long cultivation time must be put up with; thus a large amount of cultivation vessels and apparatus is required, resulting also in possibly increased contamination problems.

Upon recombinant expression, furin or furin derivatives hitherto could only be detected immunologically in the Western blot (Molloy et al., 1994. EMBO J. 13:18–33). Attempts to highly express furin or furin derivatives have so far only been successful in the Baculovirus expression system, a 20–30 fold higher expression being claimed than in transfected mammal cells (Bravo et al., 1994, J. Biol. Chem. 269:25830–25837). Yet despite the relatively high yield of furin as compared to other cell systems, the growth of these virus infected cells was limited due to the cell lysis as a consequence of virus propagation. A good expression and the isolation and purification of furin or furin derivatives is of great importance and necessity for the ever increasing application spectrum of furin and furin derivatives, respectively, e.g. in the recombinant preparation of furin-processed proteins from proproteins.

Since an overexpression of the protease negatively affects the growth of continuously growing cell cultures, solutions have been sought to reduce the toxic influence of furin on the cells. Furthermore, there is a demand for an improved method of processing furin-activated proteins from proproteins, in particular for the large-scale preparation of recombinant blood factors, such as, e.g., pro-vWF.

The present invention thus has as its object to provide a method of preparing furin or a furin derivative from a continuously growing, recombinant cell culture while maintaining the enzymatic activity of the furin or furin derivative, without substantially damaging the cell culture by the increased proteolytic activity.

A further object of the present invention consists in providing an improved method of furin-dependently proteolytically cleaving proproteins to proteins, in particular in providing a new method of processing pro-von Willebrand factor to mature, active von Willebrand factor.

According to the invention, these objects are achieved by providing new fusion proteins comprised of a furin derivative or of a derivative of a furin analogue, fused to a heterologous sequence which enables an adsorption of the furin on a solid carrier, in which optionally the C-terminal region has been removed by deletion and replaced by a heterologous sequence.

The furin or furin analogues according to the invention comprise a heterologous sequence, such as a heterologous protein, polypeptide or a functionally active peptide, in particular an affinity peptide. According to the invention, the heterologous sequence is selected such that it has a high affinity or a specific binding property for a functional group of a carrier. Therein, the heterologous protein or polypeptide should be an immunologically well characterized protein, to which, e.g., antibodies are available for coupling to a solid carrier. According to the invention, the adsorption to the solid carrier may be effected e.g. by covalent binding or via affinity. The proteins or polypeptides may be derived from e.g. β-galactosidase, c-myc-product, glutathione S-transferase, avidin and the lysin-binding kringel domain of plasma proteins, such as, e.g., from plasminogen (Evan et al., Mol. Cell. Biol. 5: 3610–3616, 1985; Duijhoven et al., Hybridoma 11:71–86, 1992). The functionally active peptides which lie in the heterologous sequence may be comprised of a series of several equal or different amino acids.

A preferred embodiment of the present invention relates to a fusion protein whose heterologous sequence part comprises a peptide which may form a covalent bond with a solid carrier, or a poly-histidine which has a high affinity particularly to heavy metal ions or specific anti-poly-histidine antibodies.

Due to the C-terminal deletion of the cytoplasmatic and transmembrane region, soluble furin or furin analogue is expressed, which is secreted from the recombinant cells. Optionally, the furin derivative or the derivative of the analogue may have the cysteine-rich region additionally deleted. According to the invention, the enzymatic activity of the deleted protein is substantially unchanged as compared to the complete protein.

Within the scope of the present invention, a derivative of a furin analogue is understood to be any furin-like protein which has equal or similar biologic activity as furin or has a sequence homology to furin. Above all, this holds for PACE, which is identical to furin, but also PACE4, PC1/PC3, PC2 and PC4 are included in the present invention.

Yet also all further proteins or nucleic acids, respectively, which have been generated from furin or the furin analogue by insertion, deletion or exchange of amino acids or nucleotides and which have a furin-like biologic activity are to be included within the scope of the present invention.

Fusion proteins comprised of a deleted furin part and a heterologous sequence have been described in the prior art, yet these known fusion proteins are not suitable for achieving the object according to the present invention. Thus, Duijhoven et al. (Hybridoma 11:71–86, 1992) disclose N-terminal furin-deletion mutants fused to glutathione S-transferase. Likewise, the pre-pro-sequence of PACE (furin) has been fused to the N-terminus of the bovine enterokinase light chain (LaVallie et al., J. Biol. Chem. 268:23311–23317, 1993). Fusion proteins containing a so-called FLAG epitope-"tag", inserted on the N-terminal end of the catalytic center of the furin after amino acid Arg107, as well as murine furin mutants, in which the transmembrane and cytoplasmatic region has been C-terminally deleted after amino acid 704 and has been replaced by an antibody epitope of the HSV glycoprotein D have also been described (Molloy et al., EMBO J. 13:18–33, 1994; Matthews et al., Protein Science 3:1197–1205, 1994). These furin derivatives have been used for the detection of furin during its maturation and processing in the Golgi-apparatus or for the detection of furin-containing cell culture supernatants by means of immunoblot and are not suitable for biotechnological application for the purposes of the present invention, in particular for cleaving pro-vWF to vWF, in vitro. Such furin derivatives thus shall not fall within the scope of the present invention.

According to a particular aspect of the present invention, the fusion protein consists of a furin derivative whose C-terminal cytoplasmatic and transmembrane domain and, optionally, cysteine-rich region have been deleted and replaced by an affinity peptide. In doing so, a furin derivative or a derivative of a furin analogue has been fused to a functional peptide, in particular of several histidine residues, preferably of 3 to 20 histidine residues, particularly preferred of 6 to 15 consecutive histidine residues. The use of affinity peptides in the form of poly-histidine residues (socalled "His-tag") C-terminally fused to a protein, for the purification and/or for functional studies of proteins has been described (Janknecht et al., Proc. Natl. Acad. Sci. USA 88:8972–8976, 1991, Hoffmann et al., Nucleic Acids Res 19:6337–6338, 1991, EP 0 282 042).

In a preferred embodiment of the present invention, a furin derivative having a deleted cytoplasmatic and transmembrane region, has been fused to a peptide of several histidine residues. According to a particular embodiment, the furin has been modified such that the sequences encoding the transmembrane and cytoplasmatic part (amino acids 708 to 794) have been deleted (r-furinΔTM) and after amino acid 707, the encoding sequence for six histidine residues has been appended. The fusion protein thus obtained was designated r-furinΔTM-His.

A further embodiment of the invention relates to a fusion protein in which a furin derivative or a derivative of a furin analogue having a deleted transmembrane and cytoplasmatic part as well as the cysteine-rich region has been fused with an affinity peptide of several histidine residues.

In a preferred embodiment, a furin derivative in which the cysteine-rich region after amino acid 585 was deleted in addition to the transmembrane and cytoplasmatic domain, has been fused to six histidine residues. This fusion protein was designated r-furinΔCys-His.

According to the invention, the fusion of a furin derivative, or of a derivative of a furin analogue, to a heterologous sequence is to be effected such that the catalytic function of the furin or furin analogue substantially is not negatively affected.

Thus, according to a particular aspect of the present invention, a short peptide spacer is inserted between the sequence of the furin derivative or a derivative of a furin analogue and the heterologous sequence, so as not to impede sterically the catalytic center of the furin derivative.

This is particularly advantageous if a direct fusion of the cysteine-rich region of the furin derivative to a peptide negatively affects the enzymatic activity of the furin derivative, impedes the coupling to the carrier by chemical or steric interactions, or interferes with an efficient processing of the proprotein. This short peptide-spacer which preferably consists of from 5 to 15 amino acids, is especially composed of small, flexible amino acids, such as alanine or glycine. In a particular embodiment, a spacer consisting of Ala-Ala-Gly-Gly-Ala-Ala (SEQ ID NO:28) is inserted between the furin-encoding sequence and the heterologous sequence of 6 histidine residues. The fusion proteins thus formed have been designated r-furinΔTM-Spacer-His and r-furinΔCys-Spacer-His.

The fusion protein according to the invention has specific binding properties to a solid carrier via its protein, polypeptide or peptide part. Therein, carriers comprising (heavy) metal ions, such as, e.g. $Ni^{2+}$, $Co^{2+}$, $Mg^{2+}$, $Li^{2+}$ or comprising antibodies may be used as the solid carriers.

According to a particular aspect of the present invention, the fusion protein is immobilized by being bound to the solid carrier. Preferably, the fusion protein according to the invention is bound with a heterologus sequence part comprised of several histidine residues on account of its affinity to (heavy) metal ions, in particular to $Ni^{2+}$, or to specific anti-poly-histidine-antibodies.

In a particular embodiment, the constructs r-furinΔTM-His, r-furinΔCys-His, r-furinΔTM-Spacer-His and r-furinΔCys-Spacer-His are bound to the carrier via their affinity to $Ni^{2+}$ ions or to an antibody. According to the present invention, the solid carrier may be provided as matrix. Binding to the matrix there is effected via the affinity groups of the solid carrier, so that the fusion protein is freely accessible. This is particularly advantageous if the fusion protein immobilized on the carrier is used for the proteolytic cleavage of proproteins and this process occurs bound to a matrix.

Natural and synthetic matrices, such as sepharose, agarose, gelatin, acrylate etc. may be used as the matrix to which the affinity carrier adsorbs. Depending on the test, the solid matrix carries a functional group which is capable of specifically binding the carrier.

A further aspect of the present invention relates to the recombinant DNA encoding the fusion proteins according to the invention.

To construct the fusion proteins, the encoding nucleotide sequence of furin or of a furin analogue is modified such that the encoding sequence for the cytoplasmatic and transmembrane region, and optionally for the cysteine-rich region, is deleted (Van der Ven et al., 1993. Crit.Rev.Oncogen 4:115–136). This is effected by genetical engineering methods known from the prior art, such as specific restriction digestion with endonucleases, ligation or PCR. The deletion mutants thus produced are then fused with a heterologous sequence, also via known techniques.

The fusion proteins according to the invention may also be prepared by chemical synthesis.

Preferably, the fusion proteins are prepared by recombinant expression. The preparation by genetical engineering may be carried out with all the usual eukaryotic expression systems, such as, e.g., permanent cell lines or viral expression systems. The permanent cell lines are produced by stable integration of the exogenous DNA into the chromosome of the host cell, e.g. Vero, MRC5, CHO, BHK; 293, Sk-Hep1, in particular liver and kidney cells, or by an episomal vector derived, e.g., from the Papilloma virus. Viral expression systems, such as vaccinia virus, Baculovirus or retroviral systems may also be used. In general, Vero-, MRC5, CHO, BHK, 293, Sk-Hep1, gland, liver and kidney cells are used as the cell lines. As the eukaryotic expression systems, also yeasts, endogenous glands (e.g. the glands of transgenic animals) and other cell types which express endogenous furin or furin analogues, may be used. Of course, also transgenic animals can be used for the expression of furin or of derivatives thereof. For the expression of recombinant proteins, CHO-DUXS B11 cells have proved particularly suitable (Urlaub et al., proc. Natl. Acad. Sci. USA 77:4216–4220, 1980).

For the recombinant preparation of the fusion proteins according to the invention, also prokaryotic expression systems may be used. Systems which enable an expression in *E. coli* or in *B. subtilis* are particularly suitable therefor.

The fusion proteins are expressed in the respective expression systems under the control of a suitable promoter. In case of the expression in eukaryotes, all known promoters, such as SV40, CMV, RSV, HSV, EBV, β-Actin, hGH or inducible promoters, such as, e.g. hsp or metallothionein promoters are suitable therefor. Preferably, the fusion proteins are expressed in CHO-DUXS B11 cells under the control of the β-actin promoter.

According to a further aspect of the present invention, a fusion protein complex comprising a fusion protein according to the invention and a solid carrier are provided. Carriers comprising metal ions, such as, e.g., $Ni^{2+}$, $Co^{2+}$, $Mg^{2+}$, $Li^{2+}$ or comprising antibodies can be used as the solid carriers. Therein, the fusion protein forms a stable complex with the carrier, wherein, according to a further aspect of the invention, this complex can be removed from a solution by binding to a matrix. Therein, binding to the matrix is effected selectively, whereby no further components of the solution are bound to the carrier material.

In a particular embodiment, the fusion protein complex is obtained in that a fusion protein-containing solution, preferably a cell culture supernatant, is contacted with a solid carrier which optionally is bound to a matrix, whereby the fusion protein specifically adsorbs to the carrier. Thus, the fusion protein can be selectively removed from the solution, and the fusion-protein-free medium may again be returned to the cell culture. This is particularly advantageous because important growth hormones excreted by the cells during cell growth are again made available to the cell culture system and are not diluted out by an exchange of medium. Simultaneously, the fusion protein which interferes with the cell growth is selectively removed from the medium and thus can no longer negatively affect cell growth. The thus obtained fusion protein-complex can be used for the specific in vitro cleavage of proprotein to protein, or it may again be detached from the carrier and be worked up separately.

A further aspect of the present invention relates to a method of preparing proteins from proproteins, in which a proprotein is proteolytically cleaved by a fusion protein or by a fusion protein complex according to the invention.

In this connection, proproteins are intended to include all the precursors of proteins, which can be converted into functional proteins by suitable proteolytic treatment. In particular, proproteins may be pro-enzymes, pre-proenzymes or other (inactive) precursors of biochemically (physiologically or biotechnologically) usable proteins or enzymes.

The preparation of proteins from proproteins, according to the invention, may, on the one hand, be effected in a manner known per se by co-expression of the complete encoding sequences of the proprotein with the fusion protein according to the invention in one cell. Since, particularly on account of the optionally missing cytoplasmatic and transmembrane region in the furin part or its analogues, the fusion protein according to the invention is secreted from the cell as a soluble protein, upon expression it can perform its enzymatic activity both in the cell as well as in the cell supernatant. Thus it is ensured that also unprocessed proprotein possibly secreted into the supernatant is cleaved by the soluble fusion protein, and thus the proprotein is completely converted into its mature form. In this method, the proteolytic cleavage takes place both in vivo, i.e. in the cells, and in vitro. On account of the soluble properties of the fusion protein, cleavage in vitro, i.e. externally of the cells, particularly constitutes an additional process for the cleavage of unprocessed proprotein secreted into the supernatant.

According to a further aspect of the present invention, the proprotein is cleaved into the mature protein in vitro by the fusion protein according to the invention. In contrast to the previously described in vivo cleavage, in the in vitro cleavage no living cells are directly or indirectly involved any more.

According to a particular embodiment of the present invention, both reaction partners, the proprotein and the fusion protein, are present in solution. The solution may be a cell-free culture supernatant, in which the proprotein and the fusion protein are co-expressed, wherein, however, it is only in the cell supernatant that the proprotein is completely cleaved into its mature form. The solution may, however, also be a cell culture supernatant from cells, in which cells transfected with recombinant fusion protein or recombinant proprotein, respectively, are co-cultured, and the expressed proteins (after separation of the cell material, in the in vitro application) in the cell culture supernatant react with each other.

According to a further embodiment, the fusion protein and the proprotein are expressed in separate cell culture systems, optionally purified, and mixed with each other. On the one hand, this embodiment allows for a higher expression of the proprotein as compared to co-expression or co-culturing, since the negative effect of the protease during cell growth is obviated, and, on the other hand, it allows for a higher yield of the processed material after in vitro processing.

According to a particular aspect of the present invention, the fusion protein is removed from the cell culture supernatant, irrespective of whether it is prepared by co-expression or by separate expression. Since soluble furin is proteolytically active also in the cell culture supernatant (Wasley et al., 1993, J. Biol. Chem. 268:8458–8465), the presence of the protease restricts the efficient growth of continuously growing cell lines, as mentioned before. According to the invention, the inventive fusion proteins substantially have the same proteolytic activity as furin or furin analogues and thus also interfere with cell growth. According to the invention, the protease action on the cells may, however, be minimized or largely prevented by removal of the protease from the cell culture supernatant, whereby the cells can grow normally.

On account of the specific binding properties of the fusion proteins of the invention to a solid carrier, the fusion protein can be removed from the fusion-protein-containing solution by contacting with a solid carrier.

According to a particular aspect of the invention, the cell culture supernatant containing the fusion protein is pumped over a solid matrix to which the affinity carrier is specifically bound. The fusion-protein-free medium subsequently is returned to the cell culture. The fusion protein bound to the solid carrier preferably is removed from the cell culture supernatant in a continuous process. Particularly preferred is a continuous method in which the cell supernatant flows over a matrix at pre-determined intervals of time. Thereby it is ensured that, with a continuous expression, the fusion protein is bound to the solid carrier in a complex, and that the fusion protein is continuously removed from the solution. The toxic effect of the protease on cell growth is largely reduced thereby, and the cells can grow to higher density, which in turn increases the yield of expression product. Simultaneously the method described enables an enrichment of the fusion protein on a matrix, whereby also a high purity of the fusion protein is ensured. A particular advantage of this method is thus the assurance of an improved cell growth combined with an enrichment of pure fusion protein on a matrix. Preferably, the matrix is a column matrix. The column matrix thus produced may be used directly for the activation of proproteins to proteins.

In principle, the method described above can also be carried out with "shed furin" or with furin analogues, the furin or the furin analogue being bound via an antibody which does not negatively affect the proteolytic activity.

In cell culture supernatants which contain both fusion protein and completely processed protein, such as, e.g., in co-expression or co-culturing, the fusion protein may, as mentioned above, be removed from the solution by binding to a first solid carrier, and may specifically be isolated. In an additional step, the protein which has already been processed may also be isolated from the solution by adsorption on a second carrier different from the first one. The second carrier is then selected such that it has specific binding properties to the processed protein and does not bind non-processed proprotein. Carriers with antibodies, peptides and proteins with a high affinity to active protein are used as preferred carriers. According to the invention, the carrier is bound to a solid matrix, which preferably is present as a column matrix. The sequence of the carriers bound to a column matrix is variable according to the method described. Coupling of the columns preferably is effected sequentially, the sequence fusion protein-binding column→protein-binding column being particularly preferred. This method offers the advantage that during the passage of the fusion protein, proprotein and protein-containing solution, a specific binding to the respective carrier takes place, and a protein and fusion protein-free solution is returned. With this method higher cell densities can be attained also when co-expressing and co-culturing fusion-protein-expressing cells. Simultaneously, an enrichment and an isolation of two different, important proteins is achieved in a single method step. It has to be emphasized that this method is not only feasable with furin-fusion proteins, but also with wild type furin or with known furin mutants which have furin activity, in that these proteins become bound to a solid matrix.

According to a preferred embodiment of the present invention, the proteolytic cleavage in vitro of the proprotein to the protein is effected such that one of the reaction partners, either the proprotein or the fusion protein, is immobilized.

In this case, the proprotein may be immobilized on a solid carrier, and a solution containing the fusion protein may be contacted with the proprotein. According to one embodiment, solutions containing purified fusion protein are used for the method of the invention. For this, the proteins are separately expressed in transfected cells by genetical engineering methods, the proteins are purified from the supernatant, dissolved in buffer and subsequently the protein-containing buffer solutions are contacted with each other. Therein, the purification of the proteins is effected by methods generally known from the prior art, such as gel filtration, ion exchange or affinity chromatography.

According to a particularly preferred embodiment of the present invention, the fusion protein is immobilized on a solid carrier and the proprotein is present in solution. With this method, a fusion protein complex adsorbed on a column matrix, containing a fusion protein bound to a carrier, is contacted with a proprotein containing solution in vitro.

To carry out the method of the invention, all inactive precursors of a protein which is converted into its mature or active form by the activity of furin or of a furin-like protein are above all suitable. Thus, in particular inactive precursors of blood factors or of viral proteins as proproteins are particularly included in the present invention, yet the invention is not restricted to these. The plasma proteins in particular are selected from factor IX, von Willebrand factor, factor VII, factor X, factor XI, factor V, protein C, protein S and albumin or derivatives thereof. Possible viral proteins or polypeptides are those of CMV, HDV, HCV, HSV, HIV, such as gp160, or influenza virus, such as HA protein (Klenk et al., 1994, Cellular Receptors for Animal viruses. CSH Laboratory Press. 241–280). Preferably, the proteins are produced by genetical engineering methods. Each precursor of a polypeptide having at least one dibasic cleavage site is, however, a candidate for the present method.

With the method according to the invention, the in vitro contact period between proprotein and fusion protein ranges between a few seconds and several days. The optimum contact depends on the fusion protein or fusion protein derivative used and the inactive proprotein precursor. The determination of the optimum contact period in which the proprotein is completely cleaved to protein may, however, be effected by any skilled artisan by means of simple tests. The incubation is mostly effected at a temperature of between 4° C. and 42° C., preferably between 20° C. and 38° C. The reaction occurs at as pH of from 5.0 to 8.0, preferably at a pH of from 6.5 to 7.9, and more particularly at a pH of 7.1. Since the furin or furin analogue activity is dependent on $Ca^{2+}$, usually such buffers which contain $Ca^{2+}$ ions are used for carrying out the method.

If one of the reaction partners is immobilized, the reaction conditions for the activation of proprotein by the fusion protein may easily be optimized by the skilled artisan in dependence on the test and within the given overall conditions. In this connection, the flow rate of the reactant present in solution is of particular importance for the contact duration as a variable. The former should be between 0.05 ml/min and 1 ml/min. As further parameters, temperature, pH and salt concentration are important. For a complete activation of proproteins, according to the present method several columns can be connected in series, either proprotein or fusion protein being immobilized on a carrier. After each passage, the protein which has already been processed can be separated from its propeptide and further purified via selective chromatography.

The reason why carrying out the method according to the invention with a reaction partner bound to a carrier is particularly advantageous is that by using a carrier, in particular a chromatographic column, the reaction allows for an additional purification step.

The active protein processed according to the present method is purified from the reaction mixture, and its activity is determined by methods known from the prior art.

Before working up into a pharmaceutical preparation, isolated and purified, processed protein is subjected to the common quality checks and brought into a therapeutically administrable form.

Thus, the invention also relates to a pharmaceutical preparation comprising a protein prepared according to the method of the invention.

Among experts it has hitherto been considered as impossible to process pro-vWF in vitro to active vWF by means of furin (Rehemtulla et al., 1992, Blood 79:2349–2355, Rehemtulla et al., 1992, Proc. Natl. Acad. Sci., USA 89:8235–8239).

Contrary to teachings, surprisingly it has been found that pro-vWF is processed in vitro to vWF by means of furin under certain test conditions.

A particular aspect of the present invention is thus that pro-vWF as proprotein is contacted with the fusion protein of the invention, preferably with furinΔTM-Spacer-His. In one aspect, pro-vWF and fusion protein are contacted in solution. The solutions preferably are cell culture supernatants of recombinant cell lines or solutions which contain purified proteins.

According to one embodiment of the present invention, cell culture supernatants of transfected cells which express pro-vWF and the fusion protein of the invention, respectively, are mixed. The cell culture supernatants optionally may be used "crude", which means that the transfected cells are not separated from the supernatant and the respective proteins are not purified. Preferably, the cell supernatants are, however, purified such before the contacting that the cells or cell fragments, respectively, are separated from the supernatant by centrifugation and, optionally, the proteins are roughly purified and concentrated. This may be effected by methods generally known from the prior art, such as, e.g., ultrafiltration, ammonium sulfate precipitation and subsequent dialysis or filtration.

According to a further embodiment, solutions containing purified pro-vWF and fusion protein are used for the method according to the invention.

A further aspect of the method according to the inveniton is the co-culturing of cells which express pro-vWF on the one hand and fusion protein on the other hand. In this method, pro-vWF in the cell culture supernantant is cleaved in vitro into its active form by the fusion protein which is also present in the cell culture supernatant, and processed vWF and fusion protein subsequently are isolated from the reaction mixture and purified, as described above. For co-culturing, all the common expression systems can be used, and various systems for expressing pro-vWF and fusion protein may be combined with each other. Preferably, however, an expression system is used in which both pro-vWF and fusion protein are expressed in different cell lines of the same origin. Preferably, CHO cells are used therein.

According to a further aspect of the invention, one of the reaction partners, pro-vWF or fusion protein, is immobilized on a carrier.

In a preferred embodiment, pro-vWF is immobilized on a carrier and the fusion protein is present in solution. Carriers which bind pro-vWF via antibodies or via specific ligands, such as, e.g., collagen or platelet-protein-gpIb, gPIIb/IIIa complex, factor VIII fragments, heparin, ristocetin or botrocetin, are particularly suitable for pro-vWF. The antibodies used may be polyclonal or monoclonal and may be directed either against the propeptide of the vWF or against the mature form of the vWF. If the antibody is directed against the vWF-propeptide, processed vWF is eluted from the carrier after contact with the fusion protein. If the antibody is directed against mature vWF, the propeptide is cleaved off by contact with the fusion protein, and is removed from the reaction mixture. The processed vWF bound to the carrier may subsequently be eluted from the column by known methods. With this variant of the method according to the invention, an additional purification and enrichment of the vWF is achieved by the elution step.

In a further aspect of the present invention, the fusion protein is bound to a matrix on a carrier with antibodies or heavy metal ions. The antibodies may be polyclonal or monoclonal. As a rule, only such antibodies are used which do not negatively affect the proteolytic activity of the fusion protein.

In a special embodiment, the fusion protein is bound to the matrix via a carrier with metal ions. As the metal ions, $Ni^{2+}$, $Co^{2+}$, $Mg^{2+}$ or $Li^{2+}$ may, e.g., be used.

Immobilization of the pro-vWF or of the furin or of its derivatives is effected by methods common in protein chemistry.

The processed, mature vWF obtained according to the method of the invention is purified from the reaction mixture, and its activity is determined by methods known from the prior art (Baruch et al., 1989, Bailliere's Clinical Haematology 2:627–672).

Prior to working up into a pharmaceutical preparation, isolated vWF is subjected to the usual quality checks, concentrated and brought into a therapeutically administrable form.

Furthermore, the invention relates to a rvWF prepared according to the method of the invention, and to a pharmaceutical preparation containing rvWF and one or more physiologically acceptable carriers. It has been found that propeptide-free rvWF prepared according to the method of the invention is characterized by a particularly high stability and structural integrity of the rvWF multimers and does not comprise satellite bands. Thus, this rvWF is suitable for stabilizing factor VIII, recombinant factor VIII or functional deletion mutants of factor VIII both in vitro and in vivo. The pharmaceutical preparation comprising propeptide-free rvWF has a high stability as well as structural integrity of the rvWF multimers and thus is particularly suitable for the treatment of haemophelia A and various forms of the vWF-disease.

A particular advantage of the method according to the invention is that pro-vWF is almost completely cleaved into its mature form. According to the invention, in vitro-processed vWF is obtained in a purity of from 80% to 100%, preferably from 90% to 100%, most preferably 95% to 100%. A contamination of vWF by pro-vWF is, above all, to be avoided with a view to its use in therapy, since an rvWF contaminated by pro-vWF might have a slighter specific activity and an increased immunogenicity, respectively. The method according to the invention has the additional advantage that the protein-chemical separation of pro-vWF from vWF, in particular in the case of immobilization of one reaction partner on a chromatographic column, is facilitated.

In case of high amplification or an excessively high expression, the furin has a negative effect on the cell. This effect can be minimized by continuously removing from the cell supernatant the furin or fusion protein which has been produced. This may e.g. be effected by furin-specific chromatography, either in the batch or in the column method. The furin or fusion protein secreted into the supernatant is bound to a chromatographic carrier, and the carrier with immobilized furin may then optionally be directly used for proprotein cleavage.

If a large amount of secreted furin or furin derivative is to be recovered, a further possibility of minimizing the toxicity of furin on the expressing cells consists in co-expressing a natural (proprotein) or a synthetic (peptide) substrate with furin or fusion protein, or to add them to the cell culture supernatant as a supplement. A substrate may also be a peptide or protein reversibly binding to furin or to the fusion protein, which, however, cannot be cleaved therefrom, which peptide or protein reduces or inhibits the catalytic activity of the furin or of the fusion protein, as long as it interacts with furin or with the fusion protein. Due to the additional proprotein or synthetic substrate, respectively, any excessive furin or fusion protein, respectively, which is unspecifically endoproteolytically active internally or externally of the cell, can be caught, and the cells will not be damaged any further. The furin or fusion protein synthesized by the high expression is secreted into the cell supernatant with high efficiency and subsequently may be purified from the cell supernatant.

Thus it is a particular advantage of the method that on account of various, above mentioned measures the high toxicity for the cell caused by large amounts of expressed furin or fusion protein is reduced, whereby the production course in the preparation of large amounts of furin or of fusion protein and proprotein is substantially facilitated or made more efficient, respectively, since first, a higher cell density is achieved and secondly, a higher yield of secreted furin is achieved in a shorter span of time, and thirdly, a complete processing of proprotein is ensured.

In the following, carrying out the method according to the invention is described in more detail:

To carry out the experiments, CHO cells were co-transfected with a pro-vWF-encoding plasmid and with a dihydrofolate reductase (DHFR)-cDNA-encoding plasmid. The DHFR-encoding plasmid serves as the marker plasmid for the selection of positive clones (CHO-vWF). For a co-expression with furin, the clone resulting therefrom, CHO-vWF, subsequently was co-transfected with plasmids which carry the furin cDNA or the cDNA encoding the fusion proteins, respectively, and the neomycin phosphotransferase gene. The neomycin phosphotransferase gene also served as a marker gene for selecting positive clones (CHO-vWF/furin). To express furin or fusion protein alone, cells were transfected with plasmids containing complete furin-cDNA or cDNA of the fusion proteins (FurinΔTM-His-cDNA, FurinΔTM-Spacer-His-cDNA, FurinΔAys-His-cDNA, FurinΔCys-Spacer-His-cDNA).

A different route of establishing pro-vWF/furin-co-expressing cells was the simultaneous co-transfection of 3 plasmids, respectively containing pro-vWF-cDNA, DHFR-cDNA and furin- or fusion protein-cDNA. By this route, a coamplification of pro-vWF- and furin-cDNA was enabled so as to obtain as high a yield of completely processed vWF as possible under the given conditions.

For co-culturing, cells were co-transfected with plasmids which either contained the encoding sequence for pro-vWF and DHFR, or for furin or fusion protein, respectively, and DHFR. Subsequently, the differently transfected cells were co-cultured.

The method according to the invention will be further explained by way of the following examples and in the drawing figures. However, the invention shall not be restricted thereto in any manner. Example 1 describes the preparation of pro-vWF-expressing and furin-expressing vectors; Example 2 describes establishing stable cell lines and illustrates in vitro cleavage of pro-vWF by furin; Example 3 describes the cloning of furin mutants and of fusion proteins; Example 4 describes the detection of the enzymatic activity of furin and of the fusion protein r-furinΔTM-His; Example 5 describes the immobilization of a fusion protein on a carrier; and Example 6 describes the activation of pro-vWF on immobilized fusion protein.

FIG. 2 shows a Western blot analysis of processed vWF and furin in cell culture supernatants after the co-expression of pro-vWF and furin.

FIGS. 4A–4D show the nucleotide and amino acid sequence of furin.

The expression vectors were produced by means of standard cloning methods (Maniatis et al., "Molecular Cloning"—A Laboratory Manual, Cold Spring Harbor Laboratory, Cold Spring Harbor, N.Y., USA, 1983). The preparation of DNA fragments by means of polymerase chain reaction (PCR) was effected by commonly known methods (Clackson et al., 1991, PCR A practical approach. Ed. McPherson, Quirke, Taylor, p.187–214).

EXAMPLE 1

Preparation of Pro-vWF and Furin Expression Vectors

Figure 1:
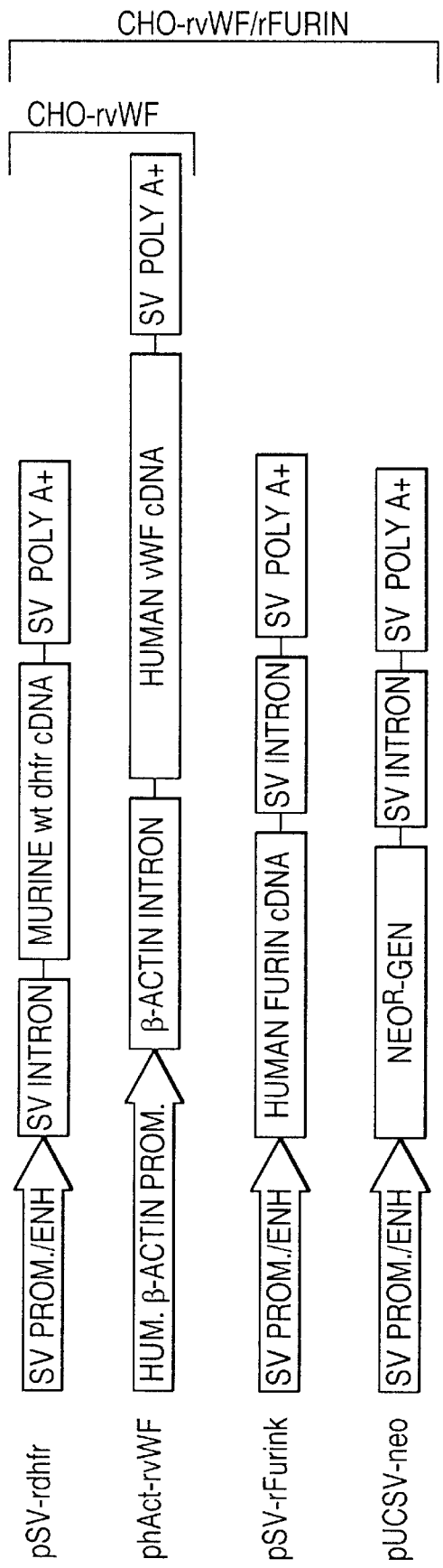
FIG. 1 is a schematical illustration of the expression cassette of pro-vWF, furin and the selection marker Dihydrofolate-reductase and neomycin-phosphotransferase that were used.

To prepare recombinant pro-vWF (rpro-vWF), plasmid phAct-vWF was constructed as described in Fischer et al., (FEBS Lett. 351: 345–348, 1994): plasmid phAct-vWF contains the complete encoding cDNA for human pro-vWF under transcriptional control of the β-actin promoter. For the selection of positive clones, plasmid pSV-rdhfr, which encodes the murine DHFR-cDNA, was used (FIG. 1).

To prepare furin-encoding vectors, the complete cDNA of human furin (FIG. 4), (Van den Ouweland et al., Nucleic Acids Res. 18:664, 1990) was isolated as the SmaI/AvrII fragment. This fragment comprises the 2.4 kb furin-encoding region as well as 0.05 kb of the 5' non-translated and 0.4 kb of the 3' non-translated region and was subsequently cloned into the SmaI and AvrII-cleaved expression vector pSV-MCS VII. The resulting plasmid was designated pSV-r-furink (FIG. 1).

Plasmid pSV-MCS VII comprises the promoter/enhancer of the "early gene" of SV40 and 50 bp of the 5'-UTR, as well as the SV40 16S/19S intron and a multiple cloning site (MCS), followed by the SV40 polyadenylating site. To prepare plasmid pSV-MCS VII, plasmid pSVβ (MacGregor et al., Nucleic Acids Res. 17: 2365, 1989) was cleaved with NotI, and the lacZ gene sequence was removed as the NotI fragment. The XbaI/HindIII fragment located 3' of the SV40 polyadenylating site was removed, the overhanging ends were filled with Klenow polymerase, and the plasmid was religated. A synthectic MCS was cloned into the singular NotI restriction cleavage site by means of NotI-compatible ends, and the NotI site was destroyed thereby. The MCS to be inserted was constituted by the two synthetic complemetary oligonucleotides #256 (5'-GGCCATCGAT TGAATTCCCC GGGGTCCTCT AGAGTCGACC TGCA- GAAGCT TAGTACTAGT AGGCCTAGGG CCCTA-3') (SEQ.ID.NO. 1) and #257 (5'-GGCCTAGGGC CTAGGC- CTA CTAGTACTAA GCTTCTGCAG GTCGACTCTA GAGGACCCCG GGGAATTCAA TCGAT-3') (SEQ.ID.NO. 2).

Plasmid pUCSV-neo was prepared by inserting the SV40-neo-expression cassette from pMAMneo (Lee et al., 1981, Nature 294:228–232) as the BamHI fragment into the BamHI restriction site of pUC19 (Yanisch-Perron et al., 1985, Gene 33:103–119).

EXAMPLE 2 a. Establishing stable rvWF and rvWF/r-furin-expressing cell lines, and expression of rvWF and r-furin The expression plasmid for rvWF, phAct-vWF (FIG. 1), was co-transfected with the selection marker plasmid pSV-rdhfr (FIG. 1) in dhfr-deficient CHO cells, the efficiently pro-rvWF-expressing clone CHO-rvWF was selected under selection conditions, and this clone was sub-cloned to stability (Fischer et al., 1994. Febs Lett. 351:345–349). For a further analysis and for rvWF expression and function studies, the cells were at first washed with PBS several times, and subsequently, unless indicated otherwise, incubated in selection medium without serum, with a regular 24 hour medium exchange.

Approximately 40% of the rvWF secreted into the cell supernatant of CHO-rvWF was unprocessed (FIG. 2 II A). To increase the efficiency of the propeptide cleavage, the r-furin expression vector pSV-r-furink in the following was co-transfected with the selection marker plasmid pUCSV-neo into the CHO-rvWF cell clone. Under selection conditions (500 µg G418/ml), clones were identified which express r-furin in addition to rvWF (CHO-rvWF/r-furin; FIGS. 2 I A, B).

The detection of rvWF in the cell culture supernatant was effected by means of Western blot analysis (FIGS. 2 I A and II A). For this, 10 µl of reduced cell culture supernatant were separated by means of SDS-PAGE (Lämmli, Nature 227:680–685, 1970), and subsequently the proteins were transferred to nitrocellulose membranes by means of the BioRad Mini Trans-Blot System (BioRad Laboratories, Richmond, Calif., USA). The Protoblot-System from Promega (Madison, Wis., USA) was used to visualize rvWF secreted into the cell culture supernatant. Rabbit anti-vWF serum (Order No. A 082) from Dakopatts (Glostrup, Denmark) was used as the antibody for vWF binding.

The detection of r-furin in the cell culture supernatant was also effected by means of Western blot analysis (FIGS. 2 I B and II B). r-Furin was visualized by using the anti-h-furin murine monoclonal antibody MON 148 (van Duijnhoven et al., Hybridoma 11: 71–86, 1992) and, as the second antibody, anti-murine IgG alkaline phosphatase conjugated goat serum (Sigma A 4656).

In 24 hour cell culture supernatants of CHO-rvWF cells there were still approximately 40% of the secreted rvWF propetide-containing pro-vWF (FIG. 2 II A), whereas, under identical conditions, in 24 hour supernatants of the CHO-rvWF/r-furin clone not any pro-vWF, but only the completely processed rvWF could be detected (FIG. 2 I A). Hence follows that in serum-free 24 hour cell culture supernatants, pro-rvWF could no longer be detected, if the cells express sufficient amounts of r-furin (FIGS. 2 I A, 1, 3, 4, 5). By additional expression of r-furin in CHO-rvWF, processing of pro-rvWF to vWF could markedly be improved (FIG. 2 I A). Hitherto, this effect has exclusively been attributed to the intra-cellular action of the r-furin prepared by co-expression (Wise et al., Proc. Natl. Acad. Sci., USA 87:9378–9382, 1990; Van de Ven et al., Mol. Bio. Rep. 14:265–275, 1990; Rehemtulla et al., Blood 79:2349–2355, 1992).

If there was a frequent medium exchange within 24 hours during the co-expression of pro-vWF and furin (every 8 hours), significant amounts of pro-rvWF could, however, also be detected in cell culture supernatants of serum-free cultured CHO-rvWF/r-furin cells (FIG. 2 I A; "8 hours"). In the supernatants of the CHO-rvWF/r-furin-cells, r-furin was detectable (FIG. 2 I B); the larger the detectable amount of r-furin in the supernatant, the smaller was the amount of pro-vWF (FIG. 2 I A).

One possible explanation—which, however, is in clear contrast to the prevailing teachings (Rehemtulla et al., 1992, Blood 79:2349–2355, Rehemtulla et al., 1992, Proc. Natl. Acad. Sci. USA 89:8235–8239)—is that r-furin which has got into the cell culture supernatant by overexpression, cleaves secreted pro-rvWF to completion only there, i.e. in vitro. The on account of the 8-hour medium exchange shorter exposition time of pro-rvWF in the supernatant to r-furin also secreted into the supernatant thus was not sufficient to process all the pro-vWF molecules present in the supernatant; on the other hand, with longer dwell times (24 hours), secreted r-furin could accumulate in the supernatent so that in the course of the r-furin accumulation more and more of the pro-rvWF molecules initially accumulated in the supernatant were processed. Subsequently, by the accumulation of ever larger amounts of r-furin, pro-rvWF that had further passed into the supernatant was immediately processed there after its secretion from the cell. While with 8 hour supernatants, the furin:pro-vWF ratio is still higher on the side of the pro-vWF, the situation has reversed with the 24 hour supernatants on account of the accumulation of r-furin.

According to the present Example, r-furin was clearly detected in the supernatant of CHO-rvWF/r-furin cells by aid of Western blot analysis and anti-h-furin monoclonal antibody (FIG. 2 I B). Therein, the processing degree of pro-rvWF was corelated to the detectable amount of r-furin in the supernatant: the more r-furin could be detected in the supernatant, the less pro-rvWF was present (compare FIGS. 2 I B with 2 I A).

b. In vitro cleavage of pro-rvWF by r-furin

To directly demonstrate the r-furin processing activity for recombinant pro-vWF in vitro, serum-free cell culture supernatants containing r-furin and pro-vWF were mixed and incubated, and respective controls were made. Since a reasonable expression yield of rwt-furin in exclusively r-furin expressing CHO cells is not possible because the increased r-furin concentration interferes with the viability of the cells, r-furin/vWF cells were resorted to as a source of r-furin. Through co-expression, detectable r-furin amounts could be achieved. CHO-rvWF, CHO-rvWF/r-furin, CHO-rvWF and CHO (at a ration of 1:1), as well as CHO-rvWF and CHO-rvWF/r-furin (at a ration of 1:1) were mixed accordingly and incubated at 37° C.

Aliquots of the reaction formulations were tested for processed vWF by means of Western blot analysis immediately before incubation and after mixing of the cell culture supernatants, respectively; further aliquots were taken at time intervals of 24 hours each and assayed.

Figure 3:
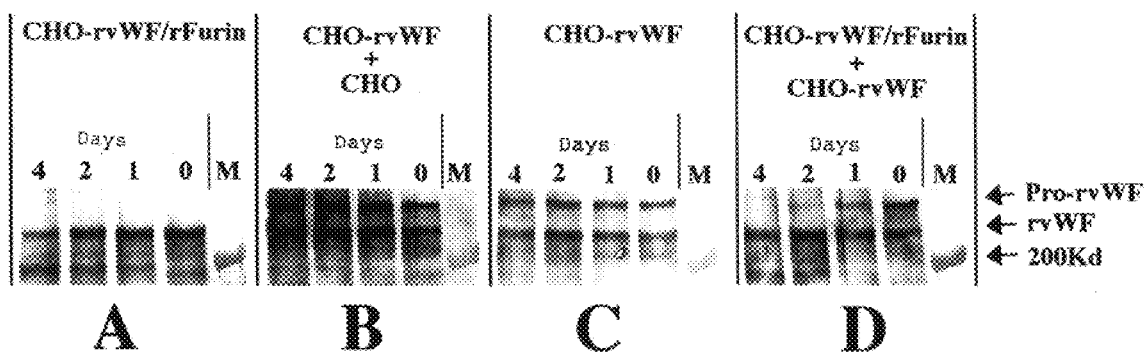
FIG. 3 shows a Western blot analysis of cell culture supernatants for rvWF, and the detection of in vitro cleavage of pro-vWF by furin.

FIG. 3 shows a complete processing of pro-rvWF only in those test formulations which had either co-expressed rvWF/r-furin or which contained CHO-rvWF/r-furin and CHO-rvWF (FIG. 3A, lanes 0–4, FIG. 3D, lanes 2 and 4. While pro-rvWF a priori was completely processed to rvWF in the 24 hour CHO rvWF/r-furin supernatant (FIG. 3A, lane 0), in CHO-rvWF cell culture supernatants there had remained 50% of unprocessed vWF in the cell culture supernatant (FIG. 3B and C). In test formulations, in which the cell culture supernatants of CHO-rvWF/r-furin and CHO-rvWF had been mixed, only a slight portion of unprocessed pro-vWF could be detected after 24 hours (FIG. 3D, lane 1). Extension of the incubation period to 48 h and 96 h (FIG. 3D, lanes 2+4) resulted in completely processed vWF. Thus it was proven that r-furin secreted into the supernatant of CHO-rvWF/r-furin cells is biologically active and completely processes pro-rvWF from CHO-rvWF supernatants in vitro.

EXAMPLE 3

Cloning and Expression of r-furin Deletion Mutants and r-furin-His-tag Fusion Proteins To prepare an r-furin capable of secretion, various C-terminal truncated furin deletion mutants were constructed and fused to additional heterologous sequences to facilitate their isolation from the culture medium later on.

All the r-furin mutants were cloned into the expression vector phAct-ΔEcoRIupstream which contains the human β-Actin promoter, and stably expressed in CHO cells, as described in Example 2.

Cloning of plasmid phAct-ΔEcoRIupstream was effected by partial EcoRI digestion of plasmid phAct (Fischer et al., FEBS. Lett. 1994, 351:345–348), filling of the overhanging ends with Klenow enzyme, and religation. Plasmid phAct-ΔEcoRIupstream differs from phAct by the lack of the EcoRI-cleavage site 5' of the promoter; however, the EcoRI cleavage site 3' of the promotor, or of the intron, respectively, is still present in the MCS.

To delete the C-terminal transmembrane domain, the r-furin cDNA downstream of position 2127 of the nucleic acid sequence (FIG. 4) and thus at amino acid 709 was deleted. With the help of the synthetic oligonucleotides #2325 (5'-GATAAGCTTG TCGACCATGG AGCTGAG-GCC CTG-3') (SEQ.ID.NO. 3) and #2819 (5'-AAGTCATGAA TTCTTAC ACCAGCCCTG CGCGCAG-3') (SEQ.ID.NO. 4), a DNA fragment was generated according to the "template" pSV-r-furink (Example 1) by means of polymerase chain reaction (PCR); this fragment contained the base pairs analogous to the first 709 amino acids of the furin, followed by a translation termination triplet. The r-furin-ΔTM fragment formed was cleaved at the flanking SalI/EcoRI-restriction sites and inserted into the SalI/EcoRI-cleaved expression vector phAct-ΔEcoRIupstream. The plasmid formed was designated pr-furin-ΔTM. The nucleotide and amino acid sequence of r-furin-ΔTM is also represented as SEQ.ID.NO. 5 and SEQ.ID.NO. 6.

To prepare furinΔTM fusion protein with a 3' fused affinity peptide, six histidine residues (His-tag) were appended to the C-terminal end of r-furinΔTM at amino acid 707 (base pair 2121):

With the help of the synthetic oligonucleotides #2325 (SEQ.ID.NO. 3) and #2823 (5'-CTAGAATTCAAT GAT-GATGATG ATGATGCCCT GCGCGCAGCC GTTGCCCC-3') (SEQ.ID.NO. 7) a DNA-fragment containing the base pairs analogous to the first 707 amino acids of the furin, followed by six histidine residues and a translation termination triplet was prepared according to the "template" pSV-r-furink (Example 1) by means of PCR. After cleavage of the flanking SalI/EcoRI restriction cleavage sites, this fragment was inserted into the SalI/EcoRI cleavage sites of the above-described vector phAct-ΔEcoRIupstream, and thus plasmid pr-furinΔTM-His was obtained. The nucleotide and amino acid sequence of r-furinΔTM-His is represented as SEQ.ID.NO. 8 and SEQ.ID.NO. 9.

Between the encoding regions of the deleted r-furinΔTM 707 and the His-tag sequence, a spacer consisting of Ala-Ala-Gly-Gly-Ala-Ala (SEQ ID NO:28) was inserted to prevent a steric impediment of the catalytic domain of the furin and to ensure a better movability and functionality of the fusion protein when coupled to a column matrix. Insertion of the spacer sequence in pr-furinΔTM-His was effected by means of PCR with the oligonucleotides #2325 (SEQ.ID.NO. 3) and #2820 (5'-CTAGAATTCAAT GAT-GATGATG ATGATGTGCAGCTCC ACCAGCTGCC CCTGCGCGCA GCCGTTGCCC C-3') (SEQ.ID.NO. 10). Analogous to the construction of pr-furinΔTM-His, this fragment was inserted into the SalI/EcoRI site of plasmid phAct-ΔEcoRIupstream. The fusion protein formed was designated prFurinΔTM-spacer-His. The nucleotide and amino acid sequence of r-furin-ΔTM-spacer-His is represented as SEQ.ID.NO. 11 and SEQ.ID.NO. 12.

Since the catalytic center of furin is localized on the N-terminal end of the molecule, an even larger region of the C-terminus, the Cys-rich region, can be deleted without significant loss of the catalytic function.

A construct was prepared in which in addition to the transmembrane domain also the Cys-rich domain is deleted. For this, a termination triplett was inserted into the furin encoding sequence after nucleotide (amino acid 585). To construct pr-furinΔCys, a DNA fragment was generated by means of PCR, with oligonucleotide #2325 (SEQ.ID.NO.3) as 5' primer and oligonucleotide #2821 (5'-CTA GAAT-TCTAA CTGCTTTCTG GAGGTACGGG CAG-3') (SEQ.ID.NO. 15) as 3' primer, and inserted in phAct-ΔEcoRIupstream analogous to the construction of furinΔTM. The nucleotide and amino acid sequence of r-furin-ΔCys is represented as SEQ.ID.NO. 13 and SEQ.ID.NO. 14.

Analogous to the furinΔTM fusion protein constructs, r-furinΔCys fusion proteins with a His-tag sequence after amino acid 585 were produced. For this, a PCR DNA fragment was generated with oligonucleotide #2325 (SEQ.ID.NO. 3) as 5' primer and oligonucleotide #2810 (5'-CTA GAATTCTTAG TGGTGATGGT GATGATGACT GCTTTCTGGA GGTACGGGCA G-3') (SEQ.ID.NO. 16) as 3' primer and inserted into plasmid pAct-ΔEcoRIupstream via the SalI/EcoRI cleavage site. The plasmid formed was designated pr-furinΔCys-His. The nucleotide and amino acid sequence of r-furin-ΔCys-His is represented as SEQ.ID.NO. 17 and SEQ.ID.NO. 18.

The construction of r-furinΔCys-spacer-His was effected by means of PCR with oligonucleotide # 2325 (SEQ.ID.NO. 3) as 5' primer and oligonucleotide # 2822 (5'-CTA GAAT-TCTTAG TGGTGATGGT GATGATGTGC AGCTC-CACCA GCTGCACTGC TTTCTGGAGG TACGGGCAG-3') (SEQ.ID.NO. 19) as 3' primer. The PCR fragment formed was inserted into plasmid pAct-ΔEcoRIupstream via the SalI/EcoRI cleavage site and desginated pr-furinΔCys-spacer-His. The nucleotide and amino acid sequence of r-furin-ΔCys-spacer-His is represented as SEQ.ID.NO. 20 and SEQ.ID.NO. 21.

Within the frame of the assays it has also been found that part of the furin molecules is endogenously cleaved a few amino acids before amino acid 707, resulting in a soluble so-called "shed" furin.

To obtain exclusively histidin-tagged r-furin molecule species in the supernatant of stable CHO cells, to increase the yield of carrier-affine r-furin, and finally, to enable a better and stronger interaction of the His-tag with the $Ni^{2+}$-NTA matrix and an improved steric freedom of movement of the r-furin derivative on the matrix, a shortened r-furin derivative was constructed, which was deleted C-terminally of the middle domain, i.e. after amino acid 576, and fused with a spacer and a 10xHis residue. For this, pr-furinΔTM-His was cleaved partially with SauI (at nucleotide position 1723–1739 in SEQ.ID.NO. 8) and completely with EcoRI, and the spacer-10xHis sequence was inserted, which was regenerated by means of the annealed synthetic oligonucleotides 5'-TGAGGGAGGT GGGGGAGGTC ATCACCACCA TCACCATCAT CATCACCATT-3' (SEQ.ID.NO. 22) and 5'-AATTAATGGTGA TGAT-GATGGT GATGGTGGTG ATGACCTCCC CCACCTCCC-3' (SEQ.ID.NO. 23). The resulting plasmid was designated pr-furinΔCys-spacer-10xHis.

Figure 5:
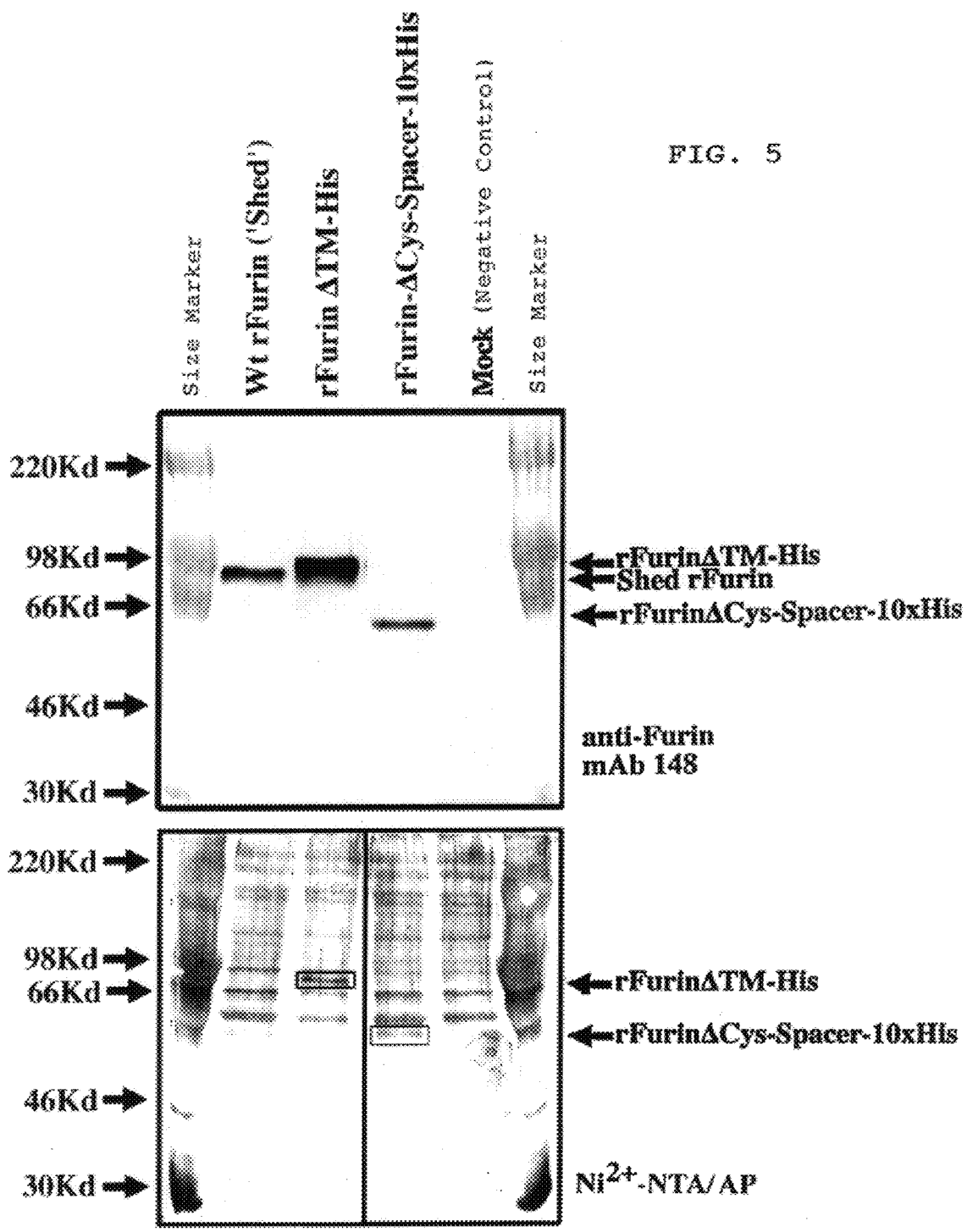
FIG. 5 shows a Western blot analysis of r-furinΔCys-Spacer-10XHis with anti-furin monoclonal antibodies.

Transient expression of r-furinΔCys-spacer-10xHis in 293 HEK cells (ATCC CRL 1573) showed that only one single protein band, reactive with anti-furin monoclonal antibody and in the expected molecule size of approximately 60 kD (taking into consideration the glycosylation) can be found. With alkaline phosphatase coupled to $Ni^{2+}$ NTA, furthermore the binding ability of the histidine-tagged molecule was demonstrated (FIG. 5).

To further shorten the C-terminal furin portion, pr-furinΔCys-spacer-10xHis at first was cleaved partially with SauI and subsequently completely with MamI. Into the cleavage site, a DNA fragment was inserted, regenerated from the annealed oligonucleotides #3787 (5'-GGACCCCTCT GGCGAGTGGG TCCTCGAGAT TGAAAACACC AGCGAAGCCA ACAACTATGG GACGCT-3') (SEQ.ID.NO. 24) and #3788 (5'-TCAAGCGTCC CATAGTTGTT GGCTTCGCTG GTGTTTTCAA TCTCGAGGAC CCACTCGCCA GAGGGGTCC-3') (SEQ. ID. NO. 25). The resulting plasmid was designated pr-furinΔΔCys-spacer-10xHis. It encodes a C-terminally deleted furin which comprises the first 563 amino acids of furin, followed by a spacer consisting of a glutamin acid residue, five glycine residues and ten histidine residues.

The supernatant transient with this construct of transfected 293 HEK cells exhibited processing activity in the fluorogenic substrate test, contrary to non-transfected cells.

EXAMPLE 4

Detection of the Enzymatic Activity of r-furinΔTM-His

The detection of the furin or fusion protein activity was effected by means of low-molecular peptide substrate Boc-Arg-Val-Arg-Arg-AMC. By the action of furin, AMC (7-amino-4-methyl coumarin) is cleaved from the substrate. Soluble AMC has fluorescent properties relative to the peptide AMC which can be used for determining the activity of furin. The fluorescent spectroscopic detection of the furin or fusion protein activity was effected at 30° C. in stirred quartz cells in a test volume of 2 ml. 1.7 ml of 100 mM HEPES buffer (pH 7.4, 1 mM $CaCl_2$ and 1 mM 2-mercaptoethanol) were mixed with 0.1 ml of a substrate solution (final substrate concentration in the test: 0.1 mM) and 0.2 ml of the sample. The fluorescence was excited at a wave length of 380 nm. After 2 hours of incubation, the fluorescent emission was measured at 438 nm (Table 1).

Table 1: Detection of the Activity of CHO-r-furinΔTM-His

The supernatants of various permanent CHO-r-furinΔTM-His cell clones and, as the controls, of CHO-rvWF/r-furin cells and CHO cells were subjected to the AMC peptide substrate test. The intensity of the fluorescent emission at 438 nm reflects the activity.

TABLE 1

| Cell clones | Intensity |
| --- | --- |
| CHO-r-furinΔTM-His | 2524 |
| CHO-rvWF/r-furin | 444 |
| CHO | 166 |

EXAMPLE 5

Immobilization of Fusion Protein r-furinΔTM-His on a Carrier

Permanent CHO cells, transfected with the expression vector pr-furinΔTM-His which had been constructed according to Example 3, were grown in medium in roller flasks. The cell culture medium was withdrawn, the cells were carefully washed with PBS and further incubated in serum-free selection medium. Subsequently, the cell culture supernatant was withdrawn every 24 hours and replaced by new medium. The supernatants were collected and combined. To adsorb secreted r-furinΔTM-His on $Ni^{2+}$-NTA agarose, 1 l of cell culture supernatant was admixed with imidazol to a final concentration of 2 mM, 1 ml of $Ni^{2+}$-NTA agarose was added, and the suspension was incubated under mild shaking at 4° C. The carrier- and matrix-bound fusion protein was separated from the supernatant by simple sedimentation or centrifugation. The column matrix with bound r-furinΔTM-His was resuspended in 10 ml of buffer A (300 mM NaCl, 10% glycerol, 1 mM β-mercaptoethanol, 2 mM imidazole, 5 mM Hepes pH 7.0, 2 mM $CaCl_2$, 2 mM $MgCl_2$), and subsequently it was centrifuged for 10 min at 600 g. The pellet was resuspended in an equal volume of buffer and a chromatography column was loaded therewith. Subsequently, the column was washed with 5 ml of buffer A containing 2 mM imidazole, washed, and equilibrated with 5 ml of serum-free selection medium.

Elution of r-furinΔTM-His was effected with buffer A containing 200 mM of imidazole. The enzymatic activity of r-furinΔTM-His was analogous to Example 4. The result is summarized in Table 2. It was shown that r-furinΔTM-His binds to the column matrix and is elutable again from the column as active molecule.

Table 2: Activity of r-furinΔTM-His before its binding to the $Ni^{2+}$-NTA matrix as well as after elution from the matrix

TABLE 2

| SUPERNATANTS | INTENSITY |
| --- | --- |
| Roller supernatant CHO-r-furinΔTM-His | 2664 |
| Equilibration | — |
| 1st washing | 340 |
| 2nd washing | 280 |

TABLE 2-continued

| SUPERNATANTS | INTENSITY |
|---|---|
| 3rd washing | 121 |
| Eluate | 2820 |

The activity of CHO-r-furinΔTM-His cells from cell culture supernatants before their binding to the column matrix, the individual washing fractions as well as the eluate were determined by means of AMC peptide substrate test.

EXAMPLE 6

Activation of pro-vWF on Immobilized Fusion Protein

The r-furinΔTM-His-$Ni^{2+}$ column prepared according to Example 5 was used to process rpro-vWF to rvWF. For this, 20 ml of serum-free cell culture supernatant of CHO-rvWF cells, adjusted to 2 mM imidazole, were passed over the column. Aliquots of the eluate were analysed via Western blot (according to Example 2). Samples of the cell culture supernatant which were not subjected to a protease treatment served as the controls. Samples of cell culture supernatants of CHO-rvWF showed about 40% of unprocessed pro-vWF, whereas in samples of the column eluate only completely processed vWF was detected.

EXAMPLE 7

Purification of His-tagged r-furin Fusion Proteins on $Ni^{2+}$-NTA-matrix

Figure 6:
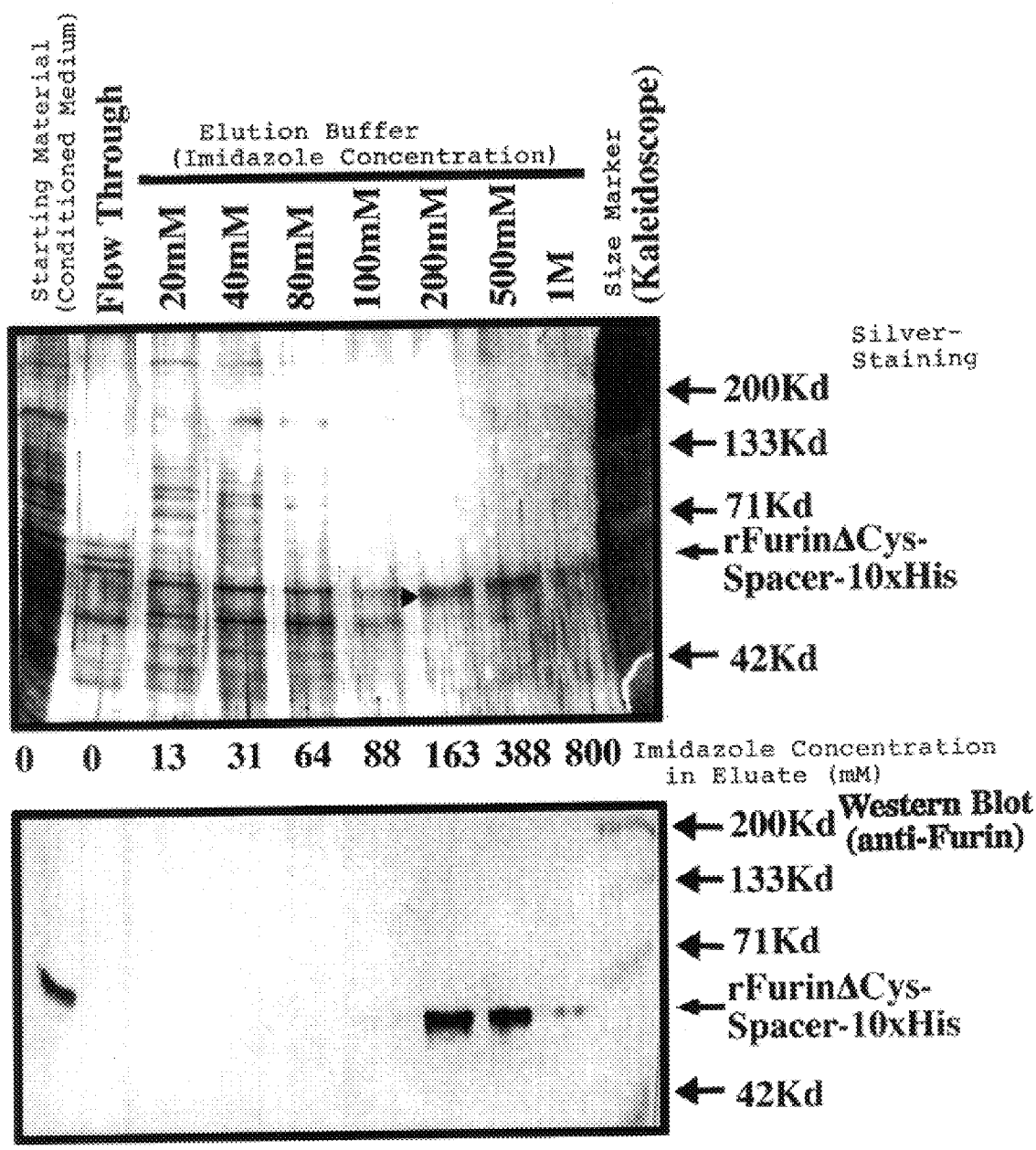
FIG. 6 shows silver staining and Western blot analysis of purified r-furin fusion protein.

Stable CHO cell clones which secrete r-furinΔCys-spacer-10xHis were prepared according to Example 2 and an $Ni^{2+}$-NTA matrix equilibrated with fresh, serum-free culture medium was loaded with conditioned medium of such clones. Adsorbed proteins were eluted from the column by means of elution buffer containing increasing concentrations of imidazole, and aliquots of the individual fractions were separated in SDS-PAGE. Subsequently, the proteins were stained with silver and detected by means of Western blot analysis, respectively (FIG. 6). Silver staining showed that a plurality of proteins contained in the conditioned medium can bind to the matrix, yet are eluted again already at a low imidazole concentration. At an imidazole concentration of up to approximately 100 mM, contaminants were eluted from the column, whereas fractions eluted at a higher imidazole concentration only contained a protein. This protein was identified as r-furinΔCys-spacer-10xHis in the Western blot with anti-furin-antibodies.

The influence of imidazole on the furin activity was determined. For this, a CHO supernatant containing r-furinΔCys-spacer-10xHis was admixed with increasing amounts of imidazole, and subsequently the samples were subjected to a fluorogenic substrate test (according to Example 4). Table 3 shows that with an increasing imidazole concentration, the ability of identical r-furin derivative amounts to react the fluorogenic substrate is successively reduced and the presence of imidazole thus inhibits the furin activity.

TABLE 3

Inhibition of the furin activity in the presence of imidazole

| r-Furin-Containing Supernatant or Medium | Imidazole-Concentration in Sample (mM) | Furin-Activity (Fluorescence-Units Measured) |
|---|---|---|
| CHO-r-furin | 0 | >1000 |
| | 50 | 818 |
| | 100 | 587 |
| | 200 | 469 |
| | 500 | 24 |
| CHO (without r-furin) | 0 | 43 |
| Medium (without CHO) | 0 | 32 |

Imidazole-containing r-furin derivative fractions thus were dialysed against 20 mM Hepes pH 7.0, 1 mM $CaCl_2$, 1 mM β-mercaptoethanol over night at 4° C. When comparing the samples before and after dialysis it was shown that after removal of the imidazole by dialysis, the activity of r-furinΔCys-spacer-10xHis could be restored from 408 to >1000 units (fraction eluted with 333 mM imidazole) and from 24 to >1000 units (fraction eluted with 780 mM imidazole).

The rapid and very clean purification of the histidine-tagged r-furin derivatives by means of the method described thus enables a large-scale process development, e.g. to process in solution purified pro-rvWF molecules (or other target proteins) by epitope-tagged r-furin derivatives. After complete processing, the two reaction partners can be selectively separated from each other by means of a $Ni^{2+}$-NTA matrix, the completely processed substrate being removed during the flow-through and the r-furin derivative being bound to the matrix. After elution from the column matrix and dialysis, the r-furin derivative is available for another processing reaction. In this manner it is possible to process a comparatively large amount of pro-rvWF with relatively little r-furin derivative in vitro by means of such repeated r-furin derivative recycling steps.

EXAMPLE 8

Detection of the Enzymatic Activity of Immobilized r-furinΔCys-spacer-10xHis Detection of the functional activity of immobilized r-furinΔCys-spacer-10xHis was effected by processing the furin-specific, fluorogenic Boc-Arg-Val-Arg-Arg-AMC (SEQ ID NO: 29) substrate (according to Example 4).

For this, 1 ml of $Ni^{2+}$-NTA matrix (Quiagen), equilibrated in serum-free cell culture medium was loaded at 4° C. with 10 ml of imidazole-free CHO-r-furinΔCys-spacer-10xHis cell culture supernatant, and, as the negative control, with conditioned medium of non-manipulated CHO cells, respectively. Then the matrix was washed three times at room temperature with serum-free cell culture medium, and subsequently the fluorogenic substrate was contacted at 30° C. with immobilized r-furinΔCys-spacer-10xHis. As the positive control, CHO-r-furinΔCys-spacer-10xHis cell culture supernatant was tested for its ability to react fluorogenic substrate in solution.

Equivalent amounts (200 μl) of the starting cell culture supernatant, the flow-through fractions and the washing steps were assayed for their r-furin derivative content by means of fluorogenic substrate test as described in Example 4. The substrate cleavage capacity values found were compared to the values of those substrate-containing solutions which had been exposed with the r-furin derivative-coupled column matrix.

It was shown that with a respective exposition, Ni²⁺-NTA-matrix-bound r-furinΔCys-spacer-10xHis reacted more than 1000 units of fluorogenic substrate and thus compared to the reaction of the fluorogenic substrate by non-immobilized r-furin derivative. Column matrix "loaded" with conditioned medium of unmanipulated CHO cells did not lead to a cleavage of the fluorogenic substrate.

This showed that r-furinΔCys-spacer-10xHis conveyes a proteolytic activity not only in solution, but also in the immobilized state. Depending on the substrate (e.g. on proproteins rFIX, rFX, rvWF, rPC, rPS, etc.) it may make sense to optimize the steric binding of the r-furin derivative to the matrix by respective variation of the spacer (e.g. lengthening the spacer and/or choosing the spacer amino acids, so as to achieve a stiff projection from the matrix or a better mobility, e.g.) and to thus still improve processing or optimize it for a given substrate. Alternatively, column matrices may be used in which the bound r-furin derivative is connected with the matrix via a longer column arm, as, e.g., in tentacle gels (cf. Example 10).

EXAMPLE 9

In Vitro-processing of Purified rvWF-precursor by Purified r-furinΔCys-spacer-10xHis Pro-rvWF-precursor protein was purified to homogeneity (with an rvWF antigen:total protein ratio of 2), and 10 μg pro-rvWF were incubated with 1340 U of purified r-furinΔCys-spacer-10xHis (cf. Example 7) in buffer (0.87 mM CaCl₂, 17 mM Hepes pH 7.0, 0.87 mM mercaptoethanol) at 37° C. The negative control, an unmanipulated CHO cell culture supernatant (without r-furinΔCys-spacer-10xHis) was processed in an analogous manner on the Ni²⁺-NTA matrix.

Aliquots of the reaction mixtures were taken at the beginning of the test as well as at various points of time and frozen. Upon finishing the incubation, these aliquots were separated in SDS-PAGE under reducing and denaturing conditions, and rvWF-reactive material was visualized in the Western blot (according to Example 1).

Figure 7:
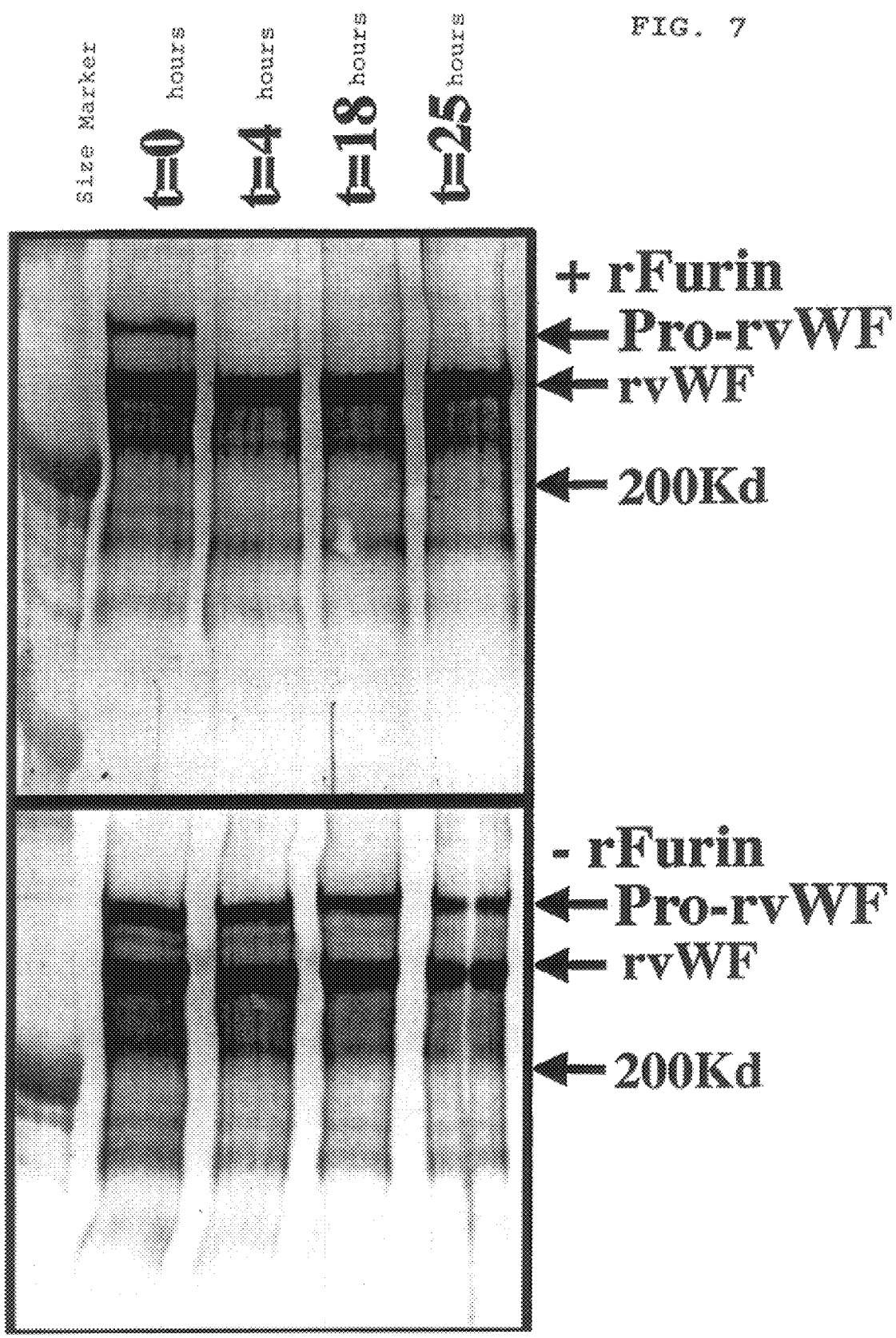
FIG. 7 shows a Western blot analysis of vWF processed by means of purified r-furin fusion protein.

FIG. 7 shows the processing of purified pro-rvWF by purified r-furinΔCys-spacer-10xHis under defined conditions. While in the presence of the r-furin derivative, pro-vWF was already completely processed after four hours (FIG. 7, top), no processing was observed in the absence of the r-furin derivative (FIG. 7, bottom). At a longer incubation with the r-furin derivative, processed rvWF molecules were not further degraded proteolytically, and the molecular integrity of the mature rvWF molecule remained stable over the entire period of the r-furin exposition (FIG. 7, top).

EXAMPLE 10

Processing of Pro-proteins by Means of r-furinΔCys-spacer-10xHis Immobilized on Chelate Tentacle Gel To possibly improve the interaction between substrate to be cleaved with column-bound r-furin derivative, it was examined whether or not Fractogel EMD®-tentacle gel (Merck) can be used in an experimental set-up as column matrix instead of Ni²⁺-NTA agarose. Since in this case the metal ions are spacially further removed from the column matrix proper, as compared to Ni²⁺-NTA agarose, an improved steric accessibility of the bound r-furin derivative could be enabled. In the present formulation, pro-protein (pro-vWF) was processed by tentacle gel-bound r-furinΔCys-spacer-10xHis:

The Fractogel EMD® tentacle gel was loaded with Ni²⁺ ions according to the manufacturer's instructions and equilibrated with fresh serum-free cell culture medium. Subsequently, the column was loaded with serum-free CHO-r-furinΔCys-spacer-10xHis supernatant. Washing steps were effected by serum-free cell culture medium, containing increasing imidazol concentrations up to 40 mM. Subsequently, the pro-protein substrate was guided over the column as serum-free CHO supernatant. By means of Western blot analysis using specific vWF antiserum, the processing of pro-protein to protein could be detected in the throughput of the column.

EXAMPLE 11

Figure 8:
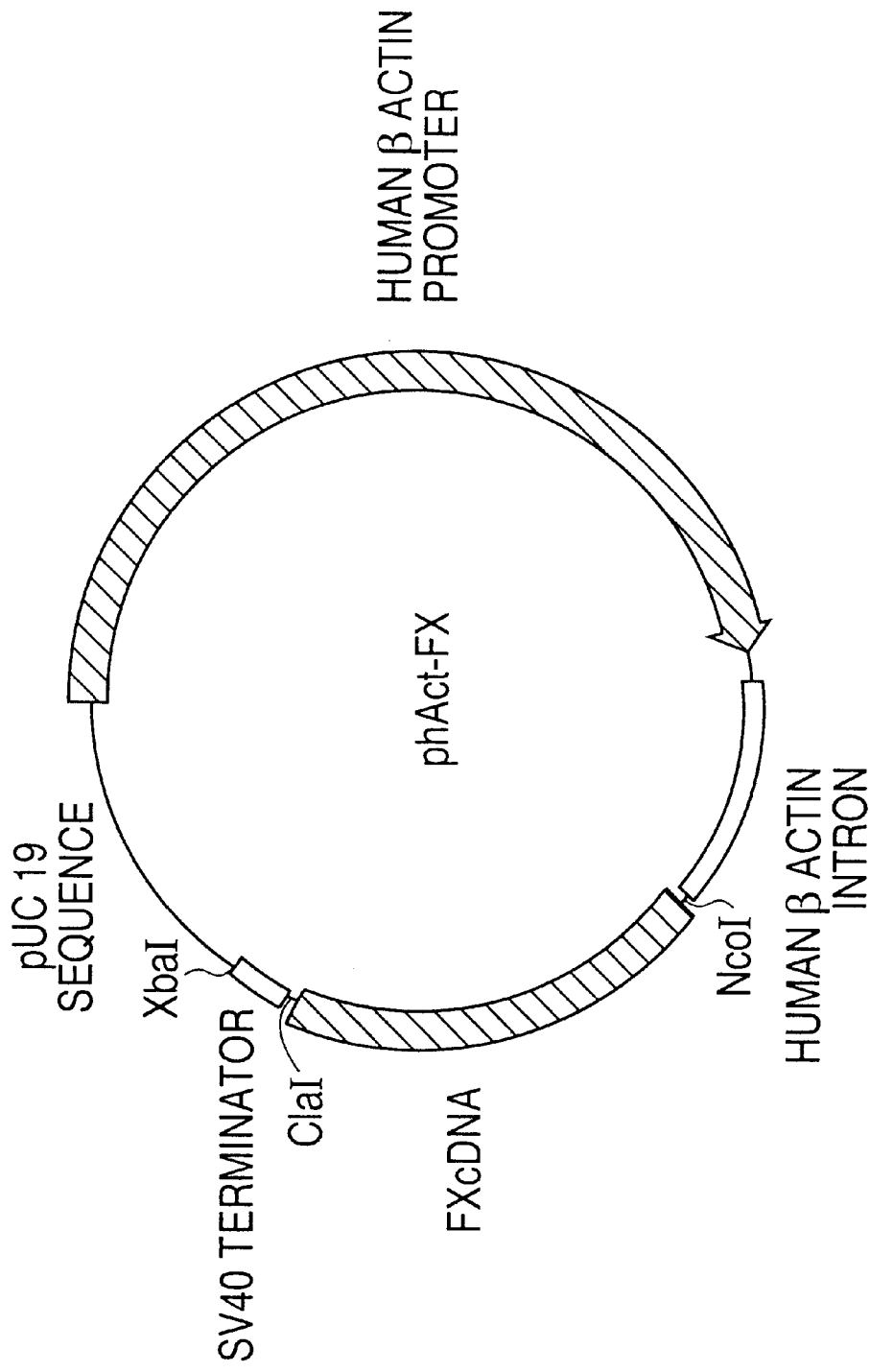
FIG. 8 is a schematical drawing of the expression vector phAct-rFX.

Processing of Single-chain rFX to rFX Light/heavy Chain by r-furinΔTM-His and r-furinΔCys-spacer-His a. Preparation of the rFX expression vector To prepare recombinant FX (rFX), the cDNA of FX was isolated from a human liver lambda-cDNA-library, as described by Messier et al. (1991, Gene 99:291–294). With oligonucleotide #2911 (5'-ATTACTCGAGAAGCTTACCATGGGGCGCCCACTG-3') (SEQ.ID.NO. 26) as 5'-primer and oligonucleotide #2912 (5'-ATTACAATTGCTGCAGGGATCCAC-3') (SEQ.ID.NO. 27) as 3'-primer, a DNA fragment was amplified from a positive clone by means of PCR, which DNA fragment contained the 1.467 kB FX-encoding sequence as well as 39 bp of the 3' non-translated region, flanked by an XhoI cleavage site at the 5' end and an MfeI cleavage site at the 3' end. In addition, the sequence ACC was incorporated upstream of the ATG of the FX by means of the primer #2911, so that an optimum Kozak transcription sequence was formed. Subsequently, this PCR product was cloned as the XhoI/MfeI fragment into the SalI and EcoRI-cleaved expression vector phAct. The resulting expression plasmid was designated phAct-rFX (FIG. 8).

The expression vector phAct comprises the human beta-Actin promoter, 78 bp 5' UTR as well as the intron, a multiple cloning cleavage site and the SV40 polyadenylating site.

b. Expression of rFX in CHO cells

Figure 9A:
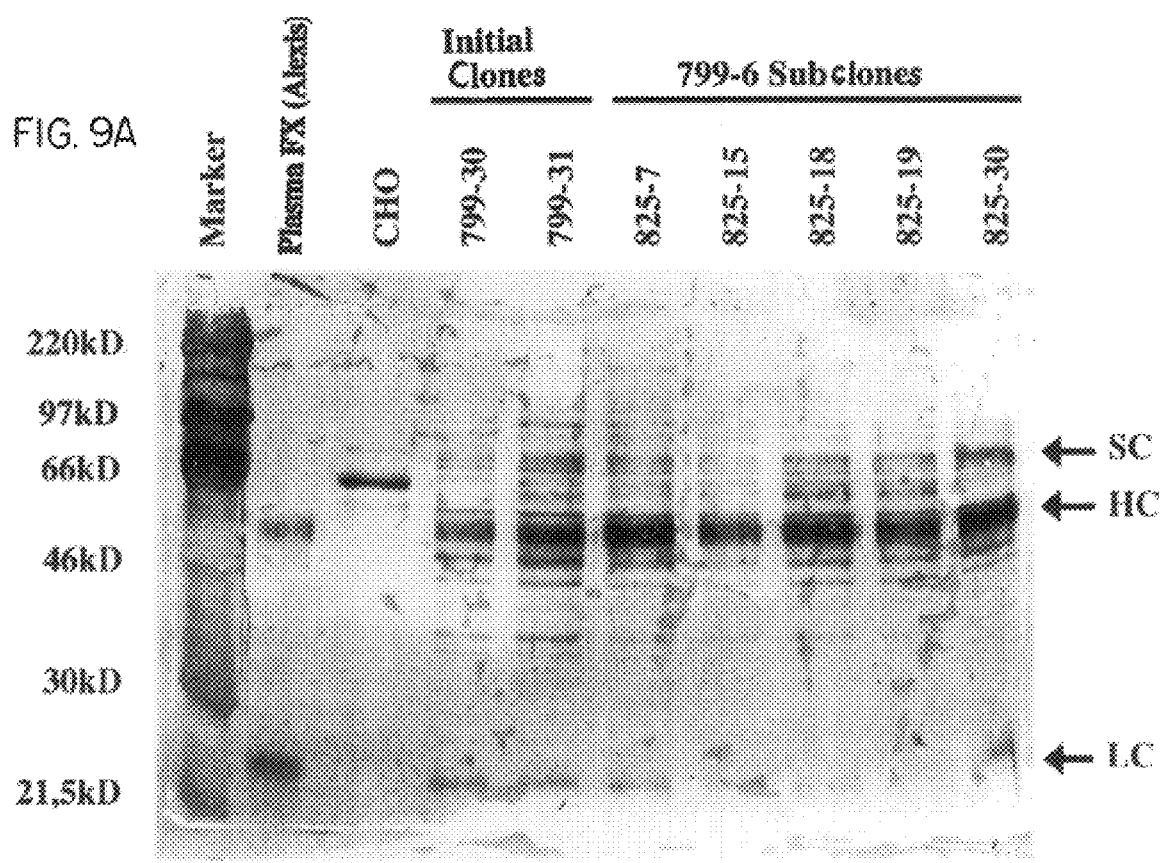
FIGS. 9A–9B show a Western blot analysis of rFactor X, expressed in CHO cells, before and after amplification with methotrexate.
Figure 9B:
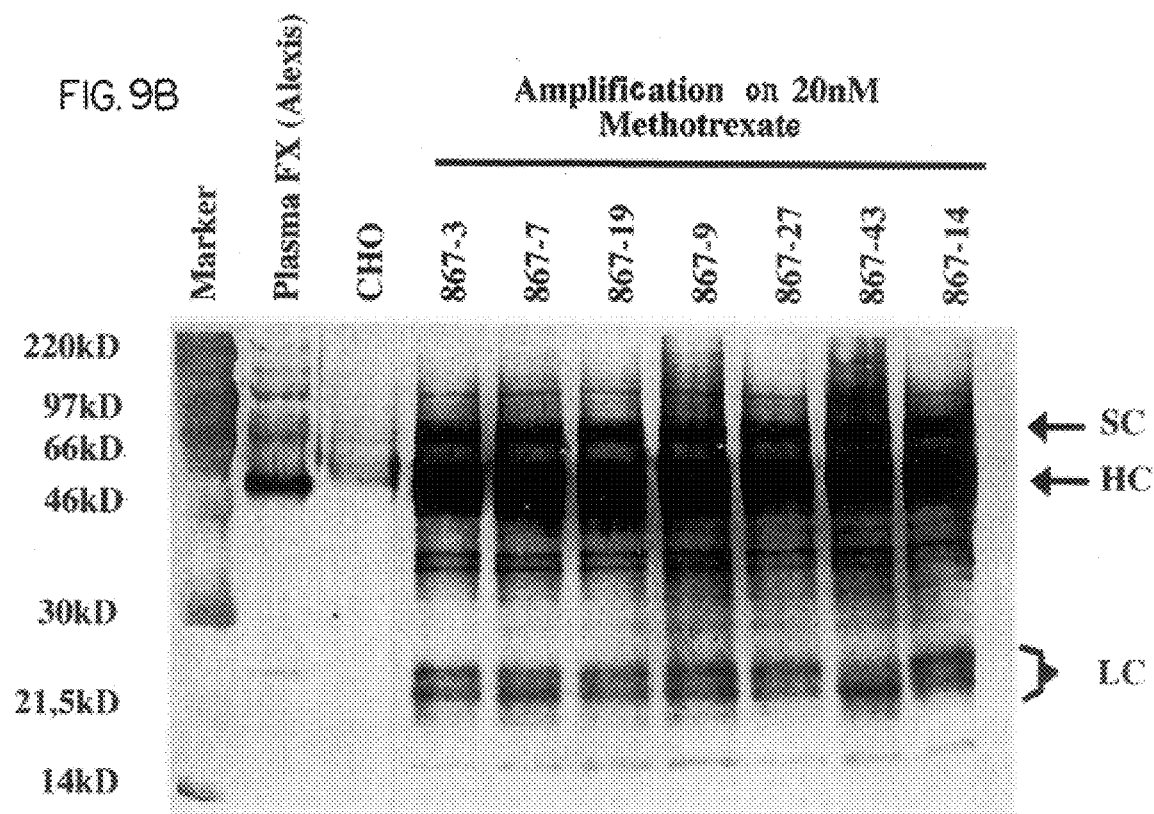

To establish a stable rFX-expressing cell line, dhfr-deficient CHO cells were co-transfected (as described in Example 2) with the expression plasmid phAct-rFX and the selection marker plasmid pSV-dhfr. For all further expression and function analyses, the cell cultures were incubated with serum-free selection medium in the presence of 10 μg/ml vitamin K for 24 hours. Expression of rFX in the resulting cell clones was detected by way of the antigen amount (ELISA), and subsequently the recombinant protein was characterised by means of SDS-PAGE (as described in Example 2) (FIGS. 9A and B). As can be recognized in the Western blot (FIG. 9A), the recombinant FX protein in the initial clones and subclones is present in the form of a light chain (LC) of 22 kD and a heavy chain (HC) of 45 kD, which are identical to the plasmatic factor X protein. In addition, a protein band can be recognized at 75 kD, which corresponds to the single chain (SC) molecule and whose presence in FX-transfected CHO cells (Wolf et al., J. Biol. Chem. 266:13726–13730, 1991) as well as in human plasma (Fair et al., Blood 64:194–204, 1984) has been described. To prepare highly expressing clones, the initial clones were amplified with increasing amounts of methotrexate and subsequently were subcloned until stabilization. Expression could be increased from approximately 200–500 ng/10E6 cells or 1 μg/ml, respectively, to 30–50 μg/10E6 cells or 100

µg/ml per 24 hours, respectively. Western blot analysis of these highly expressing cell clone supernatants (FIG. 9B and FIG. 9A, lane 2) shows an enrichment of the single-chain rFX molecule as well as the presence of additional forms of the light chain. In addition to the 22 kD form of the light chain, which corresponds to the plasmatic form (completely carboxylated without propeptide), at least two further variants of the light chain are present, with approximately 2 1kD and 20 kD. By means of N-terminal sequencing of the recombinant material, the heterogeneity of the light chain in these clones could be deduced to an incomplete cleavage of the propeptide (approximately 50% of the rFX material) as well as to undercarboxylation (approximately 50% of the rFX). The 21 kD protein is an undercarboxylated propeptide-containing form, and the 20 kD protein is an undercarboxylated propeptide-free form of the light chain.

c. In vitro cleavage of the propeptide and processing of the single-chain rFX in rFX light/heavy chain by means of r-furinΔTM-His or r-furinΔCys-spacer-His.

Figure 10A:
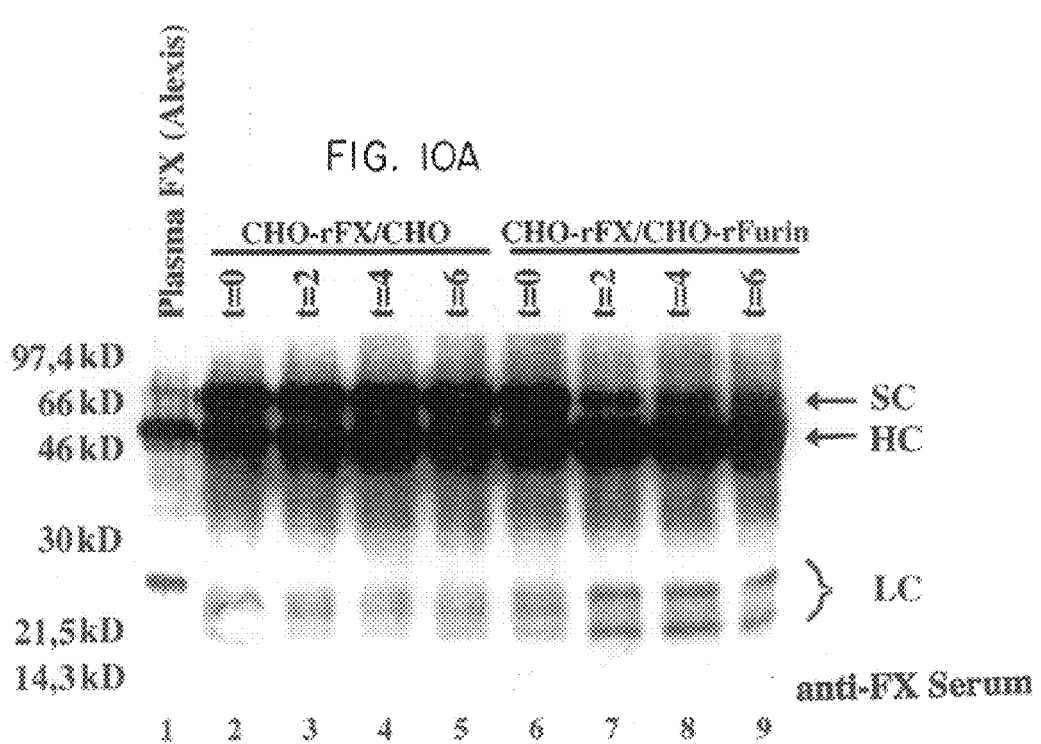
FIGS. 10A–10B show a Western blot analysis of rFactor X after in vitro-cleavage by r-furin fusion proteins.
Figure 10B:
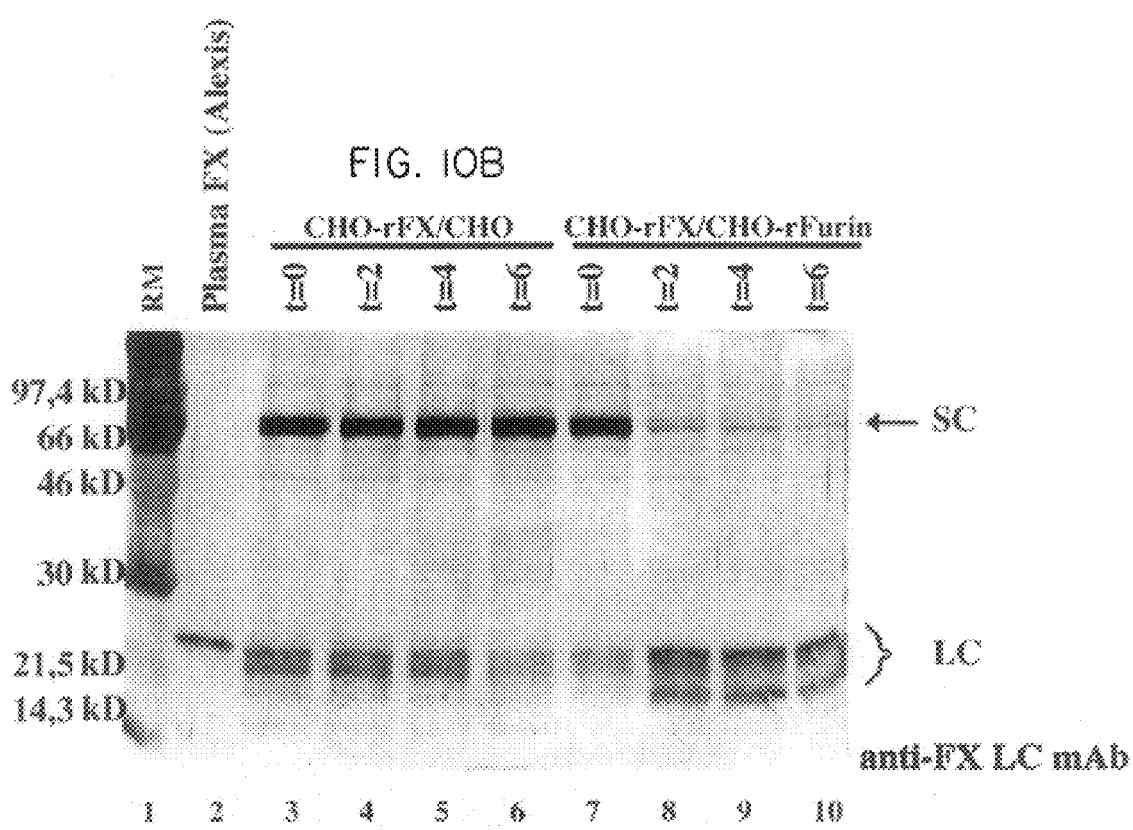

Due to the sequence homology of the cleavage sites between factor X propeptide/N-terminus of the light chain (RVTR/A) and between light/heavy chain (RRKR/S) with the consensus-furin-recognition sequence (RX$^{K/R}$R/X), it was possible to improve the processing of both single-chain and propeptide-containing rFX molecules by r-furin in vitro. Cell culture supernatants of CHO-rFX and CHO-r-furinΔTM-His (described in Example 3) as well as of CHO-rFX and CHO (as negative control) were mixed at a ration of 1:1 and incubated at 37° C. Aliquots each of the reactions were tested for processed rFX by means of Western blot analysis prior to incubation (t=0) and after various incubation periods (t=2, 4, 6 hours) (FIG. 10). The detection of rFX in the cell culture supernatants was effected by means of anti-human FX antiserum (FIG. 10A) and of a monoclonal antibody specific to the light chain of FX (FIG. 10B).

In contrast to the CHO-rFX/CHO mixture, the CHO-rFX/CHO-r-furinΔTM-His exhibits almost complete processing already after two hours of incubation at 37° C. (FIG. 10A, lane 7; FIG. 10B, lane 8). Single-chain rFX has been largely reacted to the light and heavy chain forms. In the region of the light chain, only the processed propeptide-free forms of 22 kD (carboxylated form) and 20 kD (undercarboxylated form) could be found any longer at a ratio of approximately 50:50. The correct cleavage of the pro-sequence between Arg-1 and Ala+1, and the homogeneity of the N-terminus of the light chain were determined by means of N-terminal sequencing. In the control experiment, in which CHO-rFX was mixed with CHO supernatants, also after 6 hours of incubation no change of the rFX band pattern can be recognized. Thus it has been demonstrated that r-furinΔTM-His in the supernatant of CHO cells is biologically active and can carry out both the processing of the propeptide and of the heavy/light chain of rFX. Processing of rFX has also been demonstrated with CHO-r-furinΔCys-spacer-His constructs.

d. Activity of the in vitro-processed CHO-rFX The supernatants from the experiment mentioned under c.) subsequently were tested for FX activity by means of FX-Coatest-Kit (from Chromogenix). For this, 50 µl of each supernatant were admixed with 50 µl of FX-deficient human plasma, and according to the protocol of the producer, rFX was reacted to rFXa with snake venom (RVV) in the presence of CaCl$_2$; rFXa subsequently hydrolyses the chromogenic substrate (S-2337) and leads to the liberation of the yellow-coloured paranitroaniline. Since the amount of rFXa and the colour intensity are proportional to each other, the amount of rFX activatable to rFXa/ml cell culture supernatant can be determined with the help of a calibration straight line, interpolated from values of the plasma dilution series. With these results and the known rFX antigen amount (ELISA data), the portion of the activated r-factor X in factor Xa can be calculated in %. The results are illustrated in Table 4.

TABLE 4

| Sample | OD at 405 nm | Activity mU/ml | ELISA µg/ml | % Functional FX |
|---|---|---|---|---|
| Plasma 100% | 0.829 | 991.1 | | |
| Plasma 50% | 0.434 | 515.7 | | |
| Plasma 25% | 0.217 | 254.5 | | |
| Plasma 12.5% | 0.108 | 123.3 | | |
| Plasma 6.25% | 0.054 | 58.3 | | |
| Puffer | 0.001 | 0.0 | | |
| CHO/CHO-rFurin | | | | |
| t = 0 | 0.008 | 3.0 | 0.0 | |
| t = 2 | 0.001 | 0.0 | 0.0 | |
| t = 4 | 0.010 | 5.4 | 0.0 | |
| t = 6 | 0.006 | 0.6 | 0.0 | |
| CHO-rFX/CHO | | | | |
| t = 0 | 0.170 | 197.9 | 19.9 | 24.9 |
| t = 2 | 0.131 | 151.0 | 19.9 | 19.0 |
| t = 4 | 0.153 | 177.5 | 19.9 | 22.3 |
| t = 6 | 0.163 | 189.5 | 19.9 | 23.8 |
| CHO-rFX/CHO-rFurin | | | | |
| t = 0 | 0.151 | 175.1 | 19.9 | 22.0 |
| t = 2 | 0.235 | 276.2 | 19.9 | 34.7 |
| t = 4 | 0.260 | 306.3 | 19.9 | 38.5 |
| t = 6 | 0.292 | 344.8 | 19.9 | 43.3 |

To exclude unspecific, proteolytic activity in CHO and CHO-r-furinΔTM-His supernatants, the mixture of these two cell culture supernatants was also examined. The low OD values (less than 7% of the proteolytic activity) found in these supernatants are photometric deviations and are within the standard deviation. Significant unspecific proteolytic activity in CHO supernatants, which might influence the test, thus has been excluded.

CHO-rFX, incubated with CHO supernatants (without r-furin) as control did not show any substantial rise in the rFXa activity, even after 6 hours, which activity ranged between 150–200 mU/ml due to experimental deviations and corresponded to 19–25% of functional rFX. If, in comparison thereto, CHO-rFX was incubated with CHO-r-furinΔTM-His, a significant increase in the rFX activity already formed after two hours, reaching 344 mU/ml or 43% functional portion of the CHO-rFX after 6 hours. These data correlate very well to the presence of 50% of the active or carboxylated light chain with 22 kD and 50% of the inactive or undercarboxylated light chain with 20 kD in these treated supernatants (FIG. 10).

Thus it has been proven that by in vitro-processing of CHO-rFX from highly expressing clones, the portion of rFX capable of activation to functional rFXa is substantially improved by means of an r-furin derivative.

---

What is claimed is:

1. A fusion protein comprising a (1) furin derivative with a catalytic center and a C-terminal deletion, (2) a heterologous amino acid sequence comprising an affinity peptide, and (3) a flexible peptide spacer between the furin derivative and the heterologous amino acid sequence, wherein the peptide spacer does not impede sterically the catalytic center and the affinity peptide comprises a His-tag.

2. The fusion protein according to claim 1, wherein said affinity peptide comprises several consecutive histidine residues.

3. The fusion protein according to claim 2, wherein said affinity peptide comprises 3 to 20 consecutive histidine residues.

4. The fusion protein according to claim 2, wherein said affinity peptide comprises 6 to 15 consecutive histidine residues.

5. The fusion protein according to claim 1, wherein the protein is selected from the group consisting of furinΔTM-spacer-His and furinΔCys-spacer-His.

6. The fusion protein according to claim 5, wherein the protein is selected from the group consisting of furinΔTM-spacer-His according to SEQ ID NO: 12 and furinΔCys-spacer-His according to SEQ ID NO: 21.

7. The fusion protein according to claim 1, wherein the C-terminal deletion comprises the cytoplasmic and transmembrane regions.

8. The fusion protein according to claim 1, wherein the heterologous sequence is selected from the group consisting of a protein, a polypeptide, and an affinity polypeptide.

9. The fusion protein according to claim 8, wherein the protein or polypeptide is derived from one selected from the group consisting of β-galactosidase, glutathione-S-transferase, c-myc-product, avidine, and the lysine-binding kringel domain of plasma proteins.

10. A DNA sequence encoding a fusion protein, wherein said fusion protein comprises a (1) furin derivative with a catalytic center and a C-terminal deletion, (2) a heterologous amino acid sequence comprising an affinity peptide that comprises a His-tag, and (3) a flexible peptide spacer between the furin derivative and the heterologous amino acid sequence, wherein the peptide spacer does not impede sterically the catalytic center.

11. A DNA sequence encoding a fusion protein, wherein the DNA sequence is selected from the group consisting of SEQ ID NO: 8, SEQ ID NO: 11, SEQ ID NO: 17, SEQ ID NO: 20.

12. An expression vector comprising a DNA sequence encoding a fusion protein, wherein said fusion protein comprises a (1) furin derivative with a catalytic center and a C-terminal deletion, (2) a heterologous amino acid sequence comprising an affinity peptide, and (3) a flexible peptide spacer between the furin derivative and the heterologous amino acid sequence, wherein the peptide spacer does not impede sterically the catalytic center, and the affinity peptide comprises a His-tag.

13. A transformed cell containing an expression vector comprising a DNA sequence encoding a fusion protein, wherein said fusion protein comprises a (1) furin derivative with a catalytic center and a C-terminal deletion, (2) a heterologous amino acid sequence comprising an affinity peptide, and (3) a flexible peptide spacer between the furin derivative and the heterologous amino acid sequence, wherein the peptide spacer does not impede sterically the catalytic center, and the affinity peptide comprises a His-tag.

14. A method of preparing proteins from proproteins comprising proteolytically cleaving a proprotein with a fusion protein, wherein said fusion protein comprises (1) a furin derivative having a catalytic center and a C terminal deletion, (2) a heterologous amino acid sequence comprising an affinity peptide, and (3) a flexible peptide spacer between the furin derivative and the heterologous amino acid sequence, wherein the peptide spacer does not impede sterically the catalytic center, and the affinity peptide comprises a His-tag.

15. The method according to claim 14, wherein said proprotein is cleaved in vivo by recombinant co-expression with said fusion protein.

16. The method according to claim 14, wherein said proprotein is cleaved in vitro by said fusion protein.

17. The method according to claim 16, wherein said proprotein and said fusion protein constitute two reaction partners and said two reaction partners are both present in solution.

18. The method according to claim 17, wherein said proprotein is cleaved by co-culturing recombinant cell lines, said cell lines expressing said proprotein or said fusion protein.

19. The method according to claim 17, wherein said solution is a cell culture supernatant of a recombinant cell line.

20. The method according to claim 17, wherein said solution contains purified proteins.

21. The method according to claim 14, wherein said proprotein is an inactive precursor of a plasma protein or of a viral protein.

22. The method according to claim 21, wherein said plasma protein is selected from the group consisting of factor IX, von Willebrand factor, factor VII, factor X, factor XI, factor V, protein C, protein S and albumin, and said viral protein is selected from the group consisting of HIV gp160 and influenza virus HA.

* * * * *

SEQUENCE LISTING (1) GENERAL INFORMATION:

(iii) NUMBER OF SEQUENCES: 29

(2) INFORMATION FOR SEQ ID NO:1:

(i) SEQUENCE CHARACTERISTICS:
        (A) LENGTH: 75 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:1:

GGCCATCGAT TGAATTCCCC GGGGTCCTCT AGAGTCGACC TGCAGAAGCT TAGTACTAGT      60

AGGCCTAGGG CCCTA                                                      75

(2) INFORMATION FOR SEQ ID NO:2:

(i) SEQUENCE CHARACTERISTICS:
        (A) LENGTH: 75 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:2:

GGCCTAGGGC CCTAGGCCTA CTAGTACTAA GCTTCTGCAG GTCGACTCTA GAGGACCCCG      60

GGGAATTCAA TCGAT                                                      75

(2) INFORMATION FOR SEQ ID NO:3:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:3:

GATAAGCTTG TCGACCATGG AGCTGAGGCC CTG                                   33

(2) INFORMATION FOR SEQ ID NO:4:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:4:

AAGTCATGAA TTCTTACAGC AGCCCTGCGC GCAG                                  34

(2) INFORMATION FOR SEQ ID NO:5:

(i) SEQUENCE CHARACTERISTICS:
        (A) LENGTH: 2130 base pairs
        (B) TYPE: nucleic acid
        (C) STRANDEDNESS: single
        (D) TOPOLOGY: linear

```
       (ii) MOLECULE TYPE: DNA (genomic)

(ix) FEATURE:
            (A) NAME/KEY: CDS
            (B) LOCATION: 1..2127

(ix) FEATURE:
            (A) NAME/KEY: mat_peptide
            (B) LOCATION: 1..2127

(xi) SEQUENCE DESCRIPTION: SEQ ID NO:5:

ATG GAG CTG AGG CCC TGG TTG CTA TGG GTG GTA GCA GCA ACA GGA ACC             48
Met Glu Leu Arg Pro Trp Leu Leu Trp Val Val Ala Ala Thr Gly Thr
  1               5                  10                  15

TTG GTC CTG CTA GCA GCT GAT GCT CAG GGC CAG AAG GTC TTC ACC AAC             96
Leu Val Leu Leu Ala Ala Asp Ala Gln Gly Gln Lys Val Phe Thr Asn
             20                  25                  30

ACG TGG GCT GTG CGC ATC CCT GGA GGC CCA GCG GTG GCC AAC AGT GTG            144
Thr Trp Ala Val Arg Ile Pro Gly Gly Pro Ala Val Ala Asn Ser Val
         35                  40                  45

GCA CGG AAG CAT GGG TTC CTC AAC CTG GGC CAG ATC TTC GGG GAC TAT            192
Ala Arg Lys His Gly Phe Leu Asn Leu Gly Gln Ile Phe Gly Asp Tyr
     50                  55                  60

TAC CAC TTC TGG CAT CGA GGA GTG ACG AAG CGG TCC CTG TCG CCT CAC            240
Tyr His Phe Trp His Arg Gly Val Thr Lys Arg Ser Leu Ser Pro His
 65                  70                  75                  80

CGC CCG CGG CAC AGC CGG CTG CAG AGG GAG CCT CAA GTA CAG TGG CTG            288
Arg Pro Arg His Ser Arg Leu Gln Arg Glu Pro Gln Val Gln Trp Leu
                 85                  90                  95

GAA CAG CAG GTG GCA AAG CGA CGG ACT AAA CGG GAC GTG TAC CAG GAG            336
Glu Gln Gln Val Ala Lys Arg Arg Thr Lys Arg Asp Val Tyr Gln Glu
            100                 105                 110

CCC ACA GAC CCC AAG TTT CCT CAG CAG TGG TAC CTG TCT GGT GTC ACT            384
Pro Thr Asp Pro Lys Phe Pro Gln Gln Trp Tyr Leu Ser Gly Val Thr
        115                 120                 125

CAG CGG GAC CTG AAT GTG AAG GCG GCC TGG GCG CAG GGC TAC ACA GGG            432
Gln Arg Asp Leu Asn Val Lys Ala Ala Trp Ala Gln Gly Tyr Thr Gly
    130                 135                 140

CAC GGC ATT GTG GTC TCC ATT CTG GAC GAT GGC ATC GAG AAG AAC CAC            480
His Gly Ile Val Val Ser Ile Leu Asp Asp Gly Ile Glu Lys Asn His
145                 150                 155                 160

CCG GAC TTG GCA GGC AAT TAT GAT CCT GGG GCC AGT TTT GAT GTC AAT            528
Pro Asp Leu Ala Gly Asn Tyr Asp Pro Gly Ala Ser Phe Asp Val Asn
                165                 170                 175

GAC CAG GAC CCT GAC CCC CAG CCT CGG TAC ACA CAG ATG AAT GAC AAC            576
Asp Gln Asp Pro Asp Pro Gln Pro Arg Tyr Thr Gln Met Asn Asp Asn
            180                 185                 190

AGG CAC GGC ACA CGG TGT GCG GGG GAA GTG GCT GCG GTG GCC AAC AAC            624
Arg His Gly Thr Arg Cys Ala Gly Glu Val Ala Ala Val Ala Asn Asn
        195                 200                 205

GGT GTC TGT GGT GTA GGT GTG GCC TAC AAC GCC CGC ATT GGA GGG GTG            672
Gly Val Cys Gly Val Gly Val Ala Tyr Asn Ala Arg Ile Gly Gly Val
    210                 215                 220

CGC ATG CTG GAT GGC GAG GTG ACA GAT GCA GTG GAG GCA CGC TCG CTG            720
Arg Met Leu Asp Gly Glu Val Thr Asp Ala Val Glu Ala Arg Ser Leu
225                 230                 235                 240

GGC CTG AAC CCC AAC CAC ATC CAC ATC TAC AGT GCC AGC TGG GGC CCC            768
Gly Leu Asn Pro Asn His Ile His Ile Tyr Ser Ala Ser Trp Gly Pro
                245                 250                 255

GAG GAT GAC GGC AAG ACA GTG GAT GGG CCA GCC CGC CTC GCC GAG GAG            816
Glu Asp Asp Gly Lys Thr Val Asp Gly Pro Ala Arg Leu Ala Glu Glu
```

```
                      260                     265                     270
GCC TTC TTC CGT GGG GTT AGC CAG GGC CGA GGG GGG CTG GGC TCC ATC        864
Ala Phe Phe Arg Gly Val Ser Gln Gly Arg Gly Gly Leu Gly Ser Ile
        275                     280                     285

TTT GTC TGG GCC TCG GGG AAC GGG GGC CGG GAA CAT GAC AGC TGC AAC        912
Phe Val Trp Ala Ser Gly Asn Gly Gly Arg Glu His Asp Ser Cys Asn
        290                     295                     300

TGC GAC GGC TAC ACC AAC AGT ATC TAC ACG CTG TCC ATC AGC AGC GCC        960
Cys Asp Gly Tyr Thr Asn Ser Ile Tyr Thr Leu Ser Ile Ser Ser Ala
305                     310                     315                     320

ACG CAG TTT GGC AAC GTG CCG TGG TAC AGC GAG GCC TGC TCG TCC ACA       1008
Thr Gln Phe Gly Asn Val Pro Trp Tyr Ser Glu Ala Cys Ser Ser Thr
                325                     330                     335

CTG GCC ACG ACC TAC AGC AGT GGC AAC CAG AAT GAG AAG CAG ATC GTG       1056
Leu Ala Thr Thr Tyr Ser Ser Gly Asn Gln Asn Glu Lys Gln Ile Val
        340                     345                     350

ACG ACT GAC TTG CGG CAG AAG TGC ACG GAG TCT CAC ACG GGC ACC TCA       1104
Thr Thr Asp Leu Arg Gln Lys Cys Thr Glu Ser His Thr Gly Thr Ser
        355                     360                     365

GCC TCT GCC CCC TTA GCA GCC GGC ATC ATT GCT CTC ACC CTG GAG GCC       1152
Ala Ser Ala Pro Leu Ala Ala Gly Ile Ile Ala Leu Thr Leu Glu Ala
        370                     375                     380

AAT AAG AAC CTC ACA TGG CGG GAC ATG CAA CAC CTG GTG GTA CAG ACC       1200
Asn Lys Asn Leu Thr Trp Arg Asp Met Gln His Leu Val Val Gln Thr
385                     390                     395                     400

TCG AAG CCA GCC CAC CTC AAT GCC AAC GAC TGG GCC ACC AAT GGT GTG       1248
Ser Lys Pro Ala His Leu Asn Ala Asn Asp Trp Ala Thr Asn Gly Val
                405                     410                     415

GGC CGG AAA GTG AGC CAC TCA TAT GGC TAC GGG CTT TTG GAC GCA GGC       1296
Gly Arg Lys Val Ser His Ser Tyr Gly Tyr Gly Leu Leu Asp Ala Gly
        420                     425                     430

GCC ATG GTG GCC CTG GCC CAG AAT TGG ACC ACA GTG GCC CCC CAG CGG       1344
Ala Met Val Ala Leu Ala Gln Asn Trp Thr Thr Val Ala Pro Gln Arg
        435                     440                     445

AAG TGC ATC ATC GAC ATC CTC ACC GAG CCC AAA GAC ATC GGG AAA CGG       1392
Lys Cys Ile Ile Asp Ile Leu Thr Glu Pro Lys Asp Ile Gly Lys Arg
        450                     455                     460

CTC GAG GTG CGG AAG ACC GTG ACC GCG TGC CTG GGC GAG CCC AAC CAC       1440
Leu Glu Val Arg Lys Thr Val Thr Ala Cys Leu Gly Glu Pro Asn His
465                     470                     475                     480

ATC ACT CGG CTG GAG CAC GCT CAG GCG CGG CTC ACC CTG TCC TAT AAT       1488
Ile Thr Arg Leu Glu His Ala Gln Ala Arg Leu Thr Leu Ser Tyr Asn
                485                     490                     495

CGC CGT GGC GAC CTG GCC ATC CAC CTG GTC AGC CCC ATG GGC ACC CGC       1536
Arg Arg Gly Asp Leu Ala Ile His Leu Val Ser Pro Met Gly Thr Arg
                500                     505                     510

TCC ACC CTG CTG GCA GCC AGG CCA CAT GAC TAC TCC GCA GAT GGG TTT       1584
Ser Thr Leu Leu Ala Ala Arg Pro His Asp Tyr Ser Ala Asp Gly Phe
        515                     520                     525

AAT GAC TGG GCC TTC ATG ACA ACT CAT TCC TGG GAT GAG GAT CCC TCT       1632
Asn Asp Trp Ala Phe Met Thr Thr His Ser Trp Asp Glu Asp Pro Ser
        530                     535                     540

GGC GAG TGG GTC CTA GAG ATT GAA AAC ACC AGC GAA GCC AAC AAC TAT       1680
Gly Glu Trp Val Leu Glu Ile Glu Asn Thr Ser Glu Ala Asn Asn Tyr
545                     550                     555                     560

GGG ACG CTG ACC AAG TTC ACC CTC GTA CTC TAT GGC ACC GCC CCT GAG       1728
Gly Thr Leu Thr Lys Phe Thr Leu Val Leu Tyr Gly Thr Ala Pro Glu
                565                     570                     575

GGG CTG CCC GTA CCT CCA GAA AGC AGT GGC TGC AAG ACC CTC ACG TCC       1776
```

```
Gly Leu Pro Val Pro Pro Glu Ser Ser Gly Cys Lys Thr Leu Thr Ser
            580                 585                 590

AGT CAG GCC TGT GTG GTG TGC GAG GAA GGC TTC TCC CTG CAC CAG AAG   1824
Ser Gln Ala Cys Val Val Cys Glu Glu Gly Phe Ser Leu His Gln Lys
        595                 600                 605

AGC TGT GTC CAG CAC TGC CCT CCA GGC TTC GCC CCC CAA GTC CTC GAT   1872
Ser Cys Val Gln His Cys Pro Pro Gly Phe Ala Pro Gln Val Leu Asp
    610                 615                 620

ACG CAC TAT AGC ACC GAG AAT GAC GTG GAG ACC ATC CGG GCC AGC GTC   1920
Thr His Tyr Ser Thr Glu Asn Asp Val Glu Thr Ile Arg Ala Ser Val
625                 630                 635                 640

TGC GCC CCC TGC CAC GCC TCA TGT GCC ACA TGC CAG GGG CCG GCC CTG   1968
Cys Ala Pro Cys His Ala Ser Cys Ala Thr Cys Gln Gly Pro Ala Leu
                645                 650                 655

ACA GAC TGC CTC AGC TGC CCC AGC CAC GCC TCC TTG GAC CCT GTG GAG   2016
Thr Asp Cys Leu Ser Cys Pro Ser His Ala Ser Leu Asp Pro Val Glu
            660                 665                 670

CAG ACT TGC TCC CGG CAA AGC CAG AGC AGC CGA GAG TCC CCG CCA CAG   2064
Gln Thr Cys Ser Arg Gln Ser Gln Ser Ser Arg Glu Ser Pro Pro Gln
        675                 680                 685

CAG CAG CCA CCT CGG CTG CCC CCG GAG GTG GAG GCG GGG CAA CGG CTG   2112
Gln Gln Pro Pro Arg Leu Pro Pro Glu Val Glu Ala Gly Gln Arg Leu
    690                 695                 700

CGC GCA GGG CTG CTG TAA                                           2130
Arg Ala Gly Leu Leu
705

(2) INFORMATION FOR SEQ ID NO:6:

(i) SEQUENCE CHARACTERISTICS:
        (A) LENGTH: 709 amino acids
        (B) TYPE: amino acid
        (D) TOPOLOGY: linear (ii) MOLECULE TYPE: protein (xi) SEQUENCE DESCRIPTION: SEQ ID NO:6:

Met Glu Leu Arg Pro Trp Leu Leu Trp Val Val Ala Ala Thr Gly Thr
1               5                   10                  15

Leu Val Leu Leu Ala Ala Asp Ala Gln Gly Gln Lys Val Phe Thr Asn
            20                  25                  30

Thr Trp Ala Val Arg Ile Pro Gly Gly Pro Ala Val Ala Asn Ser Val
        35                  40                  45

Ala Arg Lys His Gly Phe Leu Asn Leu Gly Gln Ile Phe Gly Asp Tyr
    50                  55                  60

Tyr His Phe Trp His Arg Gly Val Thr Lys Arg Ser Leu Ser Pro His
65                  70                  75                  80

Arg Pro Arg His Ser Arg Leu Gln Arg Glu Pro Gln Val Gln Trp Leu
                85                  90                  95

Glu Gln Gln Val Ala Lys Arg Arg Thr Lys Arg Asp Val Tyr Gln Glu
            100                 105                 110

Pro Thr Asp Pro Lys Phe Pro Gln Gln Trp Tyr Leu Ser Gly Val Thr
        115                 120                 125

Gln Arg Asp Leu Asn Val Lys Ala Ala Trp Ala Gln Gly Tyr Thr Gly
    130                 135                 140

His Gly Ile Val Val Ser Ile Leu Asp Asp Gly Ile Glu Lys Asn His
145                 150                 155                 160

Pro Asp Leu Ala Gly Asn Tyr Asp Pro Gly Ala Ser Phe Asp Val Asn
                165                 170                 175
```

```
Asp Gln Asp Pro Asp Pro Gln Pro Arg Tyr Thr Gln Met Asn Asp Asn
            180                 185                 190
Arg His Gly Thr Arg Cys Ala Gly Glu Val Ala Val Ala Asn Asn
        195                 200                 205
Gly Val Cys Gly Val Gly Val Ala Tyr Asn Ala Arg Ile Gly Gly Val
    210                 215                 220
Arg Met Leu Asp Gly Glu Val Thr Asp Ala Val Glu Ala Arg Ser Leu
225                 230                 235                 240
Gly Leu Asn Pro Asn His Ile His Ile Tyr Ser Ala Ser Trp Gly Pro
                245                 250                 255
Glu Asp Asp Gly Lys Thr Val Asp Gly Pro Ala Arg Leu Ala Glu Glu
            260                 265                 270
Ala Phe Phe Arg Gly Val Ser Gln Gly Arg Gly Gly Leu Gly Ser Ile
        275                 280                 285
Phe Val Trp Ala Ser Gly Asn Gly Gly Arg Glu His Asp Ser Cys Asn
    290                 295                 300
Cys Asp Gly Tyr Thr Asn Ser Ile Tyr Thr Leu Ser Ile Ser Ser Ala
305                 310                 315                 320
Thr Gln Phe Gly Asn Val Pro Trp Tyr Ser Glu Ala Cys Ser Ser Thr
                325                 330                 335
Leu Ala Thr Thr Tyr Ser Ser Gly Asn Gln Asn Glu Lys Gln Ile Val
            340                 345                 350
Thr Thr Asp Leu Arg Gln Lys Cys Thr Glu Ser His Thr Gly Thr Ser
        355                 360                 365
Ala Ser Ala Pro Leu Ala Ala Gly Ile Ile Ala Leu Thr Leu Glu Ala
    370                 375                 380
Asn Lys Asn Leu Thr Trp Arg Asp Met Gln His Leu Val Val Gln Thr
385                 390                 395                 400
Ser Lys Pro Ala His Leu Asn Ala Asn Asp Trp Ala Thr Asn Gly Val
                405                 410                 415
Gly Arg Lys Val Ser His Ser Tyr Gly Tyr Gly Leu Leu Asp Ala Gly
            420                 425                 430
Ala Met Val Ala Leu Ala Gln Asn Trp Thr Thr Val Ala Pro Gln Arg
        435                 440                 445
Lys Cys Ile Ile Asp Ile Leu Thr Glu Pro Lys Asp Ile Gly Lys Arg
    450                 455                 460
Leu Glu Val Arg Lys Thr Val Thr Ala Cys Leu Gly Glu Pro Asn His
465                 470                 475                 480
Ile Thr Arg Leu Glu His Ala Gln Ala Arg Leu Thr Leu Ser Tyr Asn
                485                 490                 495
Arg Arg Gly Asp Leu Ala Ile His Leu Val Ser Pro Met Gly Thr Arg
            500                 505                 510
Ser Thr Leu Leu Ala Ala Arg Pro His Asp Tyr Ser Ala Asp Gly Phe
        515                 520                 525
Asn Asp Trp Ala Phe Met Thr Thr His Ser Trp Asp Glu Asp Pro Ser
    530                 535                 540
Gly Glu Trp Val Leu Glu Ile Glu Asn Thr Ser Glu Ala Asn Asn Tyr
545                 550                 555                 560
Gly Thr Leu Thr Lys Phe Thr Leu Val Leu Tyr Gly Thr Ala Pro Glu
                565                 570                 575
Gly Leu Pro Val Pro Pro Glu Ser Ser Gly Cys Lys Thr Leu Thr Ser
            580                 585                 590
```

```
Ser Gln Ala Cys Val Val Cys Glu Glu Gly Phe Ser Leu His Gln Lys
        595                 600                 605

Ser Cys Val Gln His Cys Pro Pro Gly Phe Ala Pro Gln Val Leu Asp
    610                 615                 620

Thr His Tyr Ser Thr Glu Asn Asp Val Glu Thr Ile Arg Ala Ser Val
625                 630                 635                 640

Cys Ala Pro Cys His Ala Ser Cys Ala Thr Cys Gln Gly Pro Ala Leu
                645                 650                 655

Thr Asp Cys Leu Ser Cys Pro Ser His Ala Ser Leu Asp Pro Val Glu
            660                 665                 670

Gln Thr Cys Ser Arg Gln Ser Gln Ser Ser Arg Glu Ser Pro Pro Gln
        675                 680                 685

Gln Gln Pro Pro Arg Leu Pro Pro Glu Val Glu Ala Gly Gln Arg Leu
    690                 695                 700

Arg Ala Gly Leu Leu
705
```

(2) INFORMATION FOR SEQ ID NO:7:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

```
CTAGAATTCA ATGATGATGA TGATGATGCC CTGCGCGCAG CCGTTGCCCC            50
```

(2) INFORMATION FOR SEQ ID NO:8:

(i) SEQUENCE CHARACTERISTICS:
        (A) LENGTH: 2142 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..2139

(ix) FEATURE:
        (A) NAME/KEY: mat_peptide
        (B) LOCATION: 1..2139

(xi) SEQUENCE DESCRIPTION: SEQ ID NO:8:

```
ATG GAG CTG AGG CCC TGG TTG CTA TGG GTG GTA GCA GCA ACA GGA ACC    48
Met Glu Leu Arg Pro Trp Leu Leu Trp Val Val Ala Ala Thr Gly Thr
 1               5                  10                  15

TTG GTC CTG CTA GCA GCT GAT GCT CAG GGC CAG AAG GTC TTC ACC AAC    96
Leu Val Leu Leu Ala Ala Asp Ala Gln Gly Gln Lys Val Phe Thr Asn
                20                  25                  30

ACG TGG GCT GTG CGC ATC CCT GGA GGC CCA GCG GTG GCC AAC AGT GTG   144
Thr Trp Ala Val Arg Ile Pro Gly Gly Pro Ala Val Ala Asn Ser Val
            35                  40                  45

GCA CGG AAG CAT GGG TTC CTC AAC CTG GGC CAG ATC TTC GGG GAC TAT   192
Ala Arg Lys His Gly Phe Leu Asn Leu Gly Gln Ile Phe Gly Asp Tyr
        50                  55                  60

TAC CAC TTC TGG CAT CGA GGA GTG ACG AAG CGG TCC CTG TCG CCT CAC   240
Tyr His Phe Trp His Arg Gly Val Thr Lys Arg Ser Leu Ser Pro His
 65                  70                  75                  80
```

```
CGC CCG CGG CAC AGC CGG CTG CAG AGG GAG CCT CAA GTA CAG TGG CTG    288
Arg Pro Arg His Ser Arg Leu Gln Arg Glu Pro Gln Val Gln Trp Leu
                85                  90                  95

GAA CAG CAG GTG GCA AAG CGA CGG ACT AAA CGG GAC GTG TAC CAG GAG    336
Glu Gln Gln Val Ala Lys Arg Arg Thr Lys Arg Asp Val Tyr Gln Glu
            100                 105                 110

CCC ACA GAC CCC AAG TTT CCT CAG CAG TGG TAC CTG TCT GGT GTC ACT    384
Pro Thr Asp Pro Lys Phe Pro Gln Gln Trp Tyr Leu Ser Gly Val Thr
            115                 120                 125

CAG CGG GAC CTG AAT GTG AAG GCG GCC TGG GCG CAG GGC TAC ACA GGG    432
Gln Arg Asp Leu Asn Val Lys Ala Ala Trp Ala Gln Gly Tyr Thr Gly
        130                 135                 140

CAC GGC ATT GTG GTC TCC ATT CTG GAC GAT GGC ATC GAG AAG AAC CAC    480
His Gly Ile Val Val Ser Ile Leu Asp Asp Gly Ile Glu Lys Asn His
145                 150                 155                 160

CCG GAC TTG GCA GGC AAT TAT GAT CCT GGG GCC AGT TTT GAT GTC AAT    528
Pro Asp Leu Ala Gly Asn Tyr Asp Pro Gly Ala Ser Phe Asp Val Asn
                165                 170                 175

GAC CAG GAC CCT GAC CCC CAG CCT CGG TAC ACA CAG ATG AAT GAC AAC    576
Asp Gln Asp Pro Asp Pro Gln Pro Arg Tyr Thr Gln Met Asn Asp Asn
            180                 185                 190

AGG CAC GGC ACA CGG TGT GCG GGG GAA GTG GCT GCG GTG GCC AAC AAC    624
Arg His Gly Thr Arg Cys Ala Gly Glu Val Ala Ala Val Ala Asn Asn
            195                 200                 205

GGT GTC TGT GGT GTA GGT GTG GCC TAC AAC GCC CGC ATT GGA GGG GTG    672
Gly Val Cys Gly Val Gly Val Ala Tyr Asn Ala Arg Ile Gly Gly Val
        210                 215                 220

CGC ATG CTG GAT GGC GAG GTG ACA GAT GCA GTG GAG GCA CGC TCG CTG    720
Arg Met Leu Asp Gly Glu Val Thr Asp Ala Val Glu Ala Arg Ser Leu
225                 230                 235                 240

GGC CTG AAC CCC AAC CAC ATC CAC ATC TAC AGT GCC AGC TGG GGC CCC    768
Gly Leu Asn Pro Asn His Ile His Ile Tyr Ser Ala Ser Trp Gly Pro
                245                 250                 255

GAG GAT GAC GGC AAG ACA GTG GAT GGG CCA GCC CGC CTC GCC GAG GAG    816
Glu Asp Asp Gly Lys Thr Val Asp Gly Pro Ala Arg Leu Ala Glu Glu
            260                 265                 270

GCC TTC TTC CGT GGG GTT AGC CAG GGC CGA GGG GGG CTG GGC TCC ATC    864
Ala Phe Phe Arg Gly Val Ser Gln Gly Arg Gly Gly Leu Gly Ser Ile
            275                 280                 285

TTT GTC TGG GCC TCG GGG AAC GGG GGC CGG GAA CAT GAC AGC TGC AAC    912
Phe Val Trp Ala Ser Gly Asn Gly Gly Arg Glu His Asp Ser Cys Asn
        290                 295                 300

TGC GAC GGC TAC ACC AAC AGT ATC TAC ACG CTG TCC ATC AGC AGC GCC    960
Cys Asp Gly Tyr Thr Asn Ser Ile Tyr Thr Leu Ser Ile Ser Ser Ala
305                 310                 315                 320

ACG CAG TTT GGC AAC GTG CCG TGG TAC AGC GAG GCC TGC TCG TCC ACA    1008
Thr Gln Phe Gly Asn Val Pro Trp Tyr Ser Glu Ala Cys Ser Ser Thr
                325                 330                 335

CTG GCC ACG ACC TAC AGC AGT GGC AAC CAG AAT GAG AAG CAG ATC GTG    1056
Leu Ala Thr Thr Tyr Ser Ser Gly Asn Gln Asn Glu Lys Gln Ile Val
            340                 345                 350

ACG ACT GAC TTG CGG CAG AAG TGC ACG GAG TCT CAC ACG GGC ACC TCA    1104
Thr Thr Asp Leu Arg Gln Lys Cys Thr Glu Ser His Thr Gly Thr Ser
            355                 360                 365

GCC TCT GCC CCC TTA GCA GCC GGC ATC ATT GCT CTC ACC CTG GAG GCC    1152
Ala Ser Ala Pro Leu Ala Ala Gly Ile Ile Ala Leu Thr Leu Glu Ala
        370                 375                 380

AAT AAG AAC CTC ACA TGG CGG GAC ATG CAA CAC CTG GTG GTA CAG ACC    1200
Asn Lys Asn Leu Thr Trp Arg Asp Met Gln His Leu Val Val Gln Thr
```

```
                385                   390                   395                   400
TCG AAG CCA GCC CAC CTC AAT GCC AAC GAC TGG GCC ACC AAT GGT GTG                    1248
Ser Lys Pro Ala His Leu Asn Ala Asn Asp Trp Ala Thr Asn Gly Val
                        405                   410                   415

GGC CGG AAA GTG AGC CAC TCA TAT GGC TAC GGG CTT TTG GAC GCA GGC                    1296
Gly Arg Lys Val Ser His Ser Tyr Gly Tyr Gly Leu Leu Asp Ala Gly
            420                   425                   430

GCC ATG GTG GCC CTG GCC CAG AAT TGG ACC ACA GTG GCC CCC CAG CGG                    1344
Ala Met Val Ala Leu Ala Gln Asn Trp Thr Thr Val Ala Pro Gln Arg
        435                   440                   445

AAG TGC ATC ATC GAC ATC CTC ACC GAG CCC AAA GAC ATC GGG AAA CGG                    1392
Lys Cys Ile Ile Asp Ile Leu Thr Glu Pro Lys Asp Ile Gly Lys Arg
    450                   455                   460

CTC GAG GTG CGG AAG ACC GTG ACC GCG TGC CTG GGC GAG CCC AAC CAC                    1440
Leu Glu Val Arg Lys Thr Val Thr Ala Cys Leu Gly Glu Pro Asn His
465                   470                   475                   480

ATC ACT CGG CTG GAG CAC GCT CAG GCG CGG CTC ACC CTG TCC TAT AAT                    1488
Ile Thr Arg Leu Glu His Ala Gln Ala Arg Leu Thr Leu Ser Tyr Asn
                485                   490                   495

CGC CGT GGC GAC CTG GCC ATC CAC CTG GTC AGC CCC ATG GGC ACC CGC                    1536
Arg Arg Gly Asp Leu Ala Ile His Leu Val Ser Pro Met Gly Thr Arg
            500                   505                   510

TCC ACC CTG CTG GCA GCC AGG CCA CAT GAC TAC TCC GCA GAT GGG TTT                    1584
Ser Thr Leu Leu Ala Ala Arg Pro His Asp Tyr Ser Ala Asp Gly Phe
        515                   520                   525

AAT GAC TGG GCC TTC ATG ACA ACT CAT TCC TGG GAT GAG GAT CCC TCT                    1632
Asn Asp Trp Ala Phe Met Thr Thr His Ser Trp Asp Glu Asp Pro Ser
    530                   535                   540

GGC GAG TGG GTC CTA GAG ATT GAA AAC ACC AGC GAA GCC AAC AAC TAT                    1680
Gly Glu Trp Val Leu Glu Ile Glu Asn Thr Ser Glu Ala Asn Asn Tyr
545                   550                   555                   560

GGG ACG CTG ACC AAG TTC ACC CTC GTA CTC TAT GGC ACC GCC CCT GAG                    1728
Gly Thr Leu Thr Lys Phe Thr Leu Val Leu Tyr Gly Thr Ala Pro Glu
                565                   570                   575

GGG CTG CCC GTA CCT CCA GAA AGC AGT GGC TGC AAG ACC CTC ACG TCC                    1776
Gly Leu Pro Val Pro Pro Glu Ser Ser Gly Cys Lys Thr Leu Thr Ser
            580                   585                   590

AGT CAG GCC TGT GTG GTG TGC GAG GAA GGC TTC TCC CTG CAC CAG AAG                    1824
Ser Gln Ala Cys Val Val Cys Glu Glu Gly Phe Ser Leu His Gln Lys
        595                   600                   605

AGC TGT GTC CAG CAC TGC CCT CCA GGC TTC GCC CCC CAA GTC CTC GAT                    1872
Ser Cys Val Gln His Cys Pro Pro Gly Phe Ala Pro Gln Val Leu Asp
    610                   615                   620

ACG CAC TAT AGC ACC GAG AAT GAC GTG GAG ACC ATC CGG GCC AGC GTC                    1920
Thr His Tyr Ser Thr Glu Asn Asp Val Glu Thr Ile Arg Ala Ser Val
625                   630                   635                   640

TGC GCC CCC TGC CAC GCC TCA TGT GCC ACA TGC CAG GGG CCG GCC CTG                    1968
Cys Ala Pro Cys His Ala Ser Cys Ala Thr Cys Gln Gly Pro Ala Leu
                645                   650                   655

ACA GAC TGC CTC AGC TGC CCC AGC CAC GCC TCC TTG GAC CCT GTG GAG                    2016
Thr Asp Cys Leu Ser Cys Pro Ser His Ala Ser Leu Asp Pro Val Glu
            660                   665                   670

CAG ACT TGC TCC CGG CAA AGC CAG AGC AGC CGA GAG TCC CCG CCA CAG                    2064
Gln Thr Cys Ser Arg Gln Ser Gln Ser Ser Arg Glu Ser Pro Pro Gln
        675                   680                   685

CAG CAG CCA CCT CGG CTG CCC CCG GAG GTG GAG GCG GGC CAA CGG CTG                    2112
Gln Gln Pro Pro Arg Leu Pro Pro Glu Val Glu Ala Gly Gln Arg Leu
    690                   695                   700

CGC GCA GGG CAT CAT CAT CAT CAT CAT TGA                                            2142
```

-continued

```
Arg Ala Gly His His His His His
705                 710

(2) INFORMATION FOR SEQ ID NO:9:

(i) SEQUENCE CHARACTERISTICS:
        (A) LENGTH: 713 amino acids
        (B) TYPE: amino acid
        (D) TOPOLOGY: linear (ii) MOLECULE TYPE: protein (xi) SEQUENCE DESCRIPTION: SEQ ID NO:9:

Met Glu Leu Arg Pro Trp Leu Trp Val Val Ala Ala Thr Gly Thr
 1               5                  10                  15

Leu Val Leu Leu Ala Ala Asp Ala Gln Gly Gln Lys Val Phe Thr Asn
                20                  25                  30

Thr Trp Ala Val Arg Ile Pro Gly Gly Pro Ala Val Ala Asn Ser Val
             35                  40                  45

Ala Arg Lys His Gly Phe Leu Asn Leu Gly Gln Ile Phe Gly Asp Tyr
         50                  55                  60

Tyr His Phe Trp His Arg Gly Val Thr Lys Arg Ser Leu Ser Pro His
 65                  70                  75                  80

Arg Pro Arg His Ser Arg Leu Gln Arg Glu Pro Gln Val Gln Trp Leu
                 85                  90                  95

Glu Gln Gln Val Ala Lys Arg Arg Thr Lys Arg Asp Val Tyr Gln Glu
                100                 105                 110

Pro Thr Asp Pro Lys Phe Pro Gln Gln Trp Tyr Leu Ser Gly Val Thr
            115                 120                 125

Gln Arg Asp Leu Asn Val Lys Ala Ala Trp Ala Gln Gly Tyr Thr Gly
        130                 135                 140

His Gly Ile Val Val Ser Ile Leu Asp Asp Gly Ile Glu Lys Asn His
145                 150                 155                 160

Pro Asp Leu Ala Gly Asn Tyr Asp Pro Gly Ala Ser Phe Asp Val Asn
                165                 170                 175

Asp Gln Asp Pro Asp Pro Gln Pro Arg Tyr Thr Gln Met Asn Asp Asn
            180                 185                 190

Arg His Gly Thr Arg Cys Ala Gly Glu Val Ala Ala Val Ala Asn Asn
        195                 200                 205

Gly Val Cys Gly Val Gly Val Ala Tyr Asn Ala Arg Ile Gly Gly Val
210                 215                 220

Arg Met Leu Asp Gly Glu Val Thr Asp Ala Val Glu Ala Arg Ser Leu
225                 230                 235                 240

Gly Leu Asn Pro Asn His Ile His Ile Tyr Ser Ala Ser Trp Gly Pro
                245                 250                 255

Glu Asp Asp Gly Lys Thr Val Asp Gly Pro Ala Arg Leu Ala Glu Glu
            260                 265                 270

Ala Phe Phe Arg Gly Val Ser Gln Gly Arg Gly Gly Leu Gly Ser Ile
        275                 280                 285

Phe Val Trp Ala Ser Gly Asn Gly Gly Arg Glu His Asp Ser Cys Asn
    290                 295                 300

Cys Asp Gly Tyr Thr Asn Ser Ile Tyr Thr Leu Ser Ile Ser Ser Ala
305                 310                 315                 320

Thr Gln Phe Gly Asn Val Pro Trp Tyr Ser Glu Ala Cys Ser Ser Thr
                325                 330                 335

Leu Ala Thr Thr Tyr Ser Ser Gly Asn Gln Asn Glu Lys Gln Ile Val
```

```
                340            345            350
Thr Thr Asp Leu Arg Gln Lys Cys Thr Glu Ser His Thr Gly Thr Ser
        355                355            365

Ala Ser Ala Pro Leu Ala Ala Gly Ile Ile Ala Leu Thr Leu Glu Ala
370                375                380

Asn Lys Asn Leu Thr Trp Arg Asp Met Gln His Leu Val Val Gln Thr
385                390                395                400

Ser Lys Pro Ala His Leu Asn Ala Asn Asp Trp Ala Thr Asn Gly Val
                405                410                415

Gly Arg Lys Val Ser His Ser Tyr Gly Tyr Gly Leu Leu Asp Ala Gly
                420                425                430

Ala Met Val Ala Leu Ala Gln Asn Trp Thr Thr Val Ala Pro Gln Arg
                435                440                445

Lys Cys Ile Ile Asp Ile Leu Thr Glu Pro Lys Asp Ile Gly Lys Arg
450                455                460

Leu Glu Val Arg Lys Thr Val Thr Ala Cys Leu Gly Glu Pro Asn His
465                470                475                480

Ile Thr Arg Leu Glu His Ala Gln Ala Arg Leu Thr Leu Ser Tyr Asn
                485                490                495

Arg Arg Gly Asp Leu Ala Ile His Leu Val Ser Pro Met Gly Thr Arg
                500                505                510

Ser Thr Leu Leu Ala Ala Arg Pro His Asp Tyr Ser Ala Asp Gly Phe
        515                520                525

Asn Asp Trp Ala Phe Met Thr Thr His Ser Trp Asp Glu Asp Pro Ser
530                535                540

Gly Glu Trp Val Leu Glu Ile Glu Asn Thr Ser Glu Ala Asn Asn Tyr
545                550                555                560

Gly Thr Leu Thr Lys Phe Thr Leu Val Leu Tyr Gly Thr Ala Pro Glu
                565                570                575

Gly Leu Pro Val Pro Pro Glu Ser Ser Gly Cys Lys Thr Leu Thr Ser
                580                585                590

Ser Gln Ala Cys Val Val Cys Glu Gly Phe Ser Leu His Gln Lys
        595                600                605

Ser Cys Val Gln His Cys Pro Pro Gly Phe Ala Pro Gln Val Leu Asp
        610                615                620

Thr His Tyr Ser Thr Glu Asn Asp Val Glu Thr Ile Arg Ala Ser Val
625                630                635                640

Cys Ala Pro Cys His Ala Ser Cys Ala Thr Cys Gln Gly Pro Ala Leu
                645                650                655

Thr Asp Cys Leu Ser Cys Pro Ser His Ala Ser Leu Asp Pro Val Glu
                660                665                670

Gln Thr Cys Ser Arg Gln Ser Gln Ser Ser Arg Glu Ser Pro Gln
        675                680                685

Gln Gln Pro Pro Arg Leu Pro Pro Glu Val Glu Ala Gly Gln Arg Leu
690                695                700

Arg Ala Gly His His His His His His
705                710
```

(2) INFORMATION FOR SEQ ID NO:10:

(i) SEQUENCE CHARACTERISTICS:
        (A) LENGTH: 68 base pairs
        (B) TYPE: nucleic acid
        (C) STRANDEDNESS: single
        (D) TOPOLOGY: linear -continued

```
    (ii) MOLECULE TYPE: DNA (genomic)

(xi) SEQUENCE DESCRIPTION: SEQ ID NO:10:

CTAGAATTCA ATGATGATGA TGATGATGTG CAGCTCCACC AGCTGCCCCT GCGCGCAGCC    60

GTTGCCCC                                                              68

(2) INFORMATION FOR SEQ ID NO:11:

(i) SEQUENCE CHARACTERISTICS:
         (A) LENGTH: 2160 base pairs
         (B) TYPE: nucleic acid
         (C) STRANDEDNESS: single
         (D) TOPOLOGY: linear (ii) MOLECULE TYPE: DNA (genomic)

(ix) FEATURE:
         (A) NAME/KEY: CDS
         (B) LOCATION: 1..2157

(ix) FEATURE:
         (A) NAME/KEY: mat_peptide
         (B) LOCATION: 1..2157

(xi) SEQUENCE DESCRIPTION: SEQ ID NO:11:
```

```
ATG GAG CTG AGG CCC TGG TTG CTA TGG GTG GTA GCA GCA ACA GGA ACC      48
Met Glu Leu Arg Pro Trp Leu Leu Trp Val Val Ala Ala Thr Gly Thr
 1               5                  10                  15

TTG GTC CTG CTA GCA GCT GAT GCT CAG GGC CAG AAG GTC TTC ACC AAC      96
Leu Val Leu Leu Ala Ala Asp Ala Gln Gly Gln Lys Val Phe Thr Asn
             20                  25                  30

ACG TGG GCT GTG CGC ATC CCT GGA GGC CCA GCG GTG GCC AAC AGT GTG     144
Thr Trp Ala Val Arg Ile Pro Gly Gly Pro Ala Val Ala Asn Ser Val
         35                  40                  45

GCA CGG AAG CAT GGG TTC CTC AAC CTG GGC CAG ATC TTC GGG GAC TAT     192
Ala Arg Lys His Gly Phe Leu Asn Leu Gly Gln Ile Phe Gly Asp Tyr
     50                  55                  60

TAC CAC TTC TGG CAT CGA GGA GTG ACG AAG CGG TCC CTG TCG CCT CAC     240
Tyr His Phe Trp His Arg Gly Val Thr Lys Arg Ser Leu Ser Pro His
 65                  70                  75                  80

CGC CCG CGG CAC AGC CGG CTG CAG AGG GAG CCT CAA GTA CAG TGG CTG     288
Arg Pro Arg His Ser Arg Leu Gln Arg Glu Pro Gln Val Gln Trp Leu
                 85                  90                  95

GAA CAG CAG GTG GCA AAG CGA CGG ACT AAA CGG GAC GTG TAC CAG GAG     336
Glu Gln Gln Val Ala Lys Arg Arg Thr Lys Arg Asp Val Tyr Gln Glu
            100                 105                 110

CCC ACA GAC CCC AAG TTT CCT CAG CAG TGG TAC CTG TCT GGT GTC ACT     384
Pro Thr Asp Pro Lys Phe Pro Gln Gln Trp Tyr Leu Ser Gly Val Thr
        115                 120                 125

CAG CGG GAC CTG AAT GTG AAG GCG GCC TGG GCG CAG GGC TAC ACA GGG     432
Gln Arg Asp Leu Asn Val Lys Ala Ala Trp Ala Gln Gly Tyr Thr Gly
    130                 135                 140

CAC GGC ATT GTG GTC TCC ATT CTG GAC GAT GGC ATC GAG AAG AAC CAC     480
His Gly Ile Val Val Ser Ile Leu Asp Asp Gly Ile Glu Lys Asn His
145                 150                 155                 160

CCG GAC TTG GCA GGC AAT TAT GAT CCT GGG GCC AGT TTT GAT GTC AAT     528
Pro Asp Leu Ala Gly Asn Tyr Asp Pro Gly Ala Ser Phe Asp Val Asn
                165                 170                 175

GAC CAG GAC CCT GAC CCC CAG CCT CGG TAC ACA CAG ATG AAT GAC AAC     576
Asp Gln Asp Pro Asp Pro Gln Pro Arg Tyr Thr Gln Met Asn Asp Asn
            180                 185                 190

AGG CAC GGC ACA CGG TGT GCG GGG GAA GTG GCT GCG GTG GCC AAC AAC     624
```

```
                Arg His Gly Thr Arg Cys Ala Gly Glu Val Ala Val Ala Asn Asn
                            195                 200                 205

GGT GTC TGT GGT GTA GGT GTG GCC TAC AAC GCC CGC ATT GGA GGG GTG              672
Gly Val Cys Gly Val Gly Val Ala Tyr Asn Ala Arg Ile Gly Gly Val
            210                 215                 220

CGC ATG CTG GAT GGC GAG GTG ACA GAT GCA GTG GAG GCA CGC TCG CTG              720
Arg Met Leu Asp Gly Glu Val Thr Asp Ala Val Glu Ala Arg Ser Leu
225                 230                 235                 240

GGC CTG AAC CCC AAC CAC ATC CAC ATC TAC AGT GCC AGC TGG GGC CCC              768
Gly Leu Asn Pro Asn His Ile His Ile Tyr Ser Ala Ser Trp Gly Pro
                245                 250                 255

GAG GAT GAC GGC AAG ACA GTG GAT GGG CCA GCC CGC CTC GCC GAG GAG              816
Glu Asp Asp Gly Lys Thr Val Asp Gly Pro Ala Arg Leu Ala Glu Glu
            260                 265                 270

GCC TTC TTC CGT GGG GTT AGC CAG GGC CGA GGG GGG CTG GGC TCC ATC              864
Ala Phe Phe Arg Gly Val Ser Gln Gly Arg Gly Gly Leu Gly Ser Ile
                275                 280                 285

TTT GTC TGG GCC TCG GGG AAC GGG GGC CGG GAA CAT GAC AGC TGC AAC              912
Phe Val Trp Ala Ser Gly Asn Gly Gly Arg Glu His Asp Ser Cys Asn
            290                 295                 300

TGC GAC GGC TAC ACC AAC AGT ATC TAC ACG CTG TCC ATC AGC AGC GCC              960
Cys Asp Gly Tyr Thr Asn Ser Ile Tyr Thr Leu Ser Ile Ser Ser Ala
305                 310                 315                 320

ACG CAG TTT GGC AAC GTG CCG TGG TAC AGC GAG GCC TGC TCG TCC ACA             1008
Thr Gln Phe Gly Asn Val Pro Trp Tyr Ser Glu Ala Cys Ser Ser Thr
                325                 330                 335

CTG GCC ACG ACC TAC AGC AGT GGC AAC CAG AAT GAG AAG CAG ATC GTG             1056
Leu Ala Thr Thr Tyr Ser Ser Gly Asn Gln Asn Glu Lys Gln Ile Val
            340                 345                 350

ACG ACT GAC TTG CGG CAG AAG TGC ACG GAG TCT CAC ACG GGC ACC TCA             1104
Thr Thr Asp Leu Arg Gln Lys Cys Thr Glu Ser His Thr Gly Thr Ser
                355                 360                 365

GCC TCT GCC CCC TTA GCA GCC GGC ATC ATT GCT CTC ACC CTG GAG GCC             1152
Ala Ser Ala Pro Leu Ala Ala Gly Ile Ile Ala Leu Thr Leu Glu Ala
370                 375                 380

AAT AAG AAC CTC ACA TGG CGG GAC ATG CAA CAC CTG GTG GTA CAG ACC             1200
Asn Lys Asn Leu Thr Trp Arg Asp Met Gln His Leu Val Val Gln Thr
385                 390                 395                 400

TCG AAG CCA GCC CAC CTC AAT GCC AAC GAC TGG GCC ACC AAT GGT GTG             1248
Ser Lys Pro Ala His Leu Asn Ala Asn Asp Trp Ala Thr Asn Gly Val
                405                 410                 415

GGC CGG AAA GTG AGC CAC TCA TAT GGC TAC GGG CTT TTG GAC GCA GGC             1296
Gly Arg Lys Val Ser His Ser Tyr Gly Tyr Gly Leu Leu Asp Ala Gly
            420                 425                 430

GCC ATG GTG GCC CTG GCC CAG AAT TGG ACC ACA GTG GCC CCC CAG CGG             1344
Ala Met Val Ala Leu Ala Gln Asn Trp Thr Thr Val Ala Pro Gln Arg
                435                 440                 445

AAG TGC ATC ATC GAC ATC CTC ACC GAG CCC AAA GAC ATC GGG AAA CGG             1392
Lys Cys Ile Ile Asp Ile Leu Thr Glu Pro Lys Asp Ile Gly Lys Arg
450                 455                 460

CTC GAG GTG CGG AAG ACC GTG ACC GCG TGC CTG GGC GAG CCC AAC CAC             1440
Leu Glu Val Arg Lys Thr Val Thr Ala Cys Leu Gly Glu Pro Asn His
465                 470                 475                 480

ATC ACT CGG CTG GAG CAC GCT CAG GCG CGG CTC ACC CTG TCC TAT AAT             1488
Ile Thr Arg Leu Glu His Ala Gln Ala Arg Leu Thr Leu Ser Tyr Asn
                485                 490                 495

CGC CGT GGC GAC CTG GCC ATC CAC CTG GTC AGC CCC ATG GGC ACC CGC             1536
Arg Arg Gly Asp Leu Ala Ile His Leu Val Ser Pro Met Gly Thr Arg
                500                 505                 510
```

```
TCC ACC CTG CTG GCA GCC AGG CCA CAT GAC TAC TCC GCA GAT GGG TTT          1584
Ser Thr Leu Leu Ala Ala Arg Pro His Asp Tyr Ser Ala Asp Gly Phe
            515                 520                 525

AAT GAC TGG GCC TTC ATG ACA ACT CAT TCC TGG GAT GAG GAT CCC TCT          1632
Asn Asp Trp Ala Phe Met Thr Thr His Ser Trp Asp Glu Asp Pro Ser
530                 535                 540

GGC GAG TGG GTC CTA GAG ATT GAA AAC ACC AGC GAA GCC AAC AAC TAT          1680
Gly Glu Trp Val Leu Glu Ile Glu Asn Thr Ser Glu Ala Asn Asn Tyr
545                 550                 555                 560

GGG ACG CTG ACC AAG TTC ACC CTC GTA CTC TAT GGC ACC GCC CCT GAG          1728
Gly Thr Leu Thr Lys Phe Thr Leu Val Leu Tyr Gly Thr Ala Pro Glu
                565                 570                 575

GGG CTG CCC GTA CCT CCA GAA AGC AGT GGC TGC AAG ACC CTC ACG TCC          1776
Gly Leu Pro Val Pro Pro Glu Ser Ser Gly Cys Lys Thr Leu Thr Ser
            580                 585                 590

AGT CAG GCC TGT GTG GTG TGC GAG GAA GGC TTC TCC CTG CAC CAG AAG          1824
Ser Gln Ala Cys Val Val Cys Glu Glu Gly Phe Ser Leu His Gln Lys
            595                 600                 605

AGC TGT GTC CAG CAC TGC CCT CCA GGC TTC GCC CCC CAA GTC CTC GAT          1872
Ser Cys Val Gln His Cys Pro Pro Gly Phe Ala Pro Gln Val Leu Asp
610                 615                 620

ACG CAC TAT AGC ACC GAG AAT GAC GTG GAG ACC ATC CGG GCC AGC GTC          1920
Thr His Tyr Ser Thr Glu Asn Asp Val Glu Thr Ile Arg Ala Ser Val
625                 630                 635                 640

TGC GCC CCC TGC CAC GCC TCA TGT GCC ACA TGC CAG GGG CCG GCC CTG          1968
Cys Ala Pro Cys His Ala Ser Cys Ala Thr Cys Gln Gly Pro Ala Leu
                645                 650                 655

ACA GAC TGC CTC AGC TGC CCC AGC CAC GCC TCC TTG GAC CCT GTG GAG          2016
Thr Asp Cys Leu Ser Cys Pro Ser His Ala Ser Leu Asp Pro Val Glu
            660                 665                 670

CAG ACT TGC TCC CGG CAA AGC CAG AGC AGC CGA GAG TCC CCG CCA CAG          2064
Gln Thr Cys Ser Arg Gln Ser Gln Ser Ser Arg Glu Ser Pro Pro Gln
            675                 680                 685

CAG CAG CCA CCT CGG CTG CCC CCG GAG GTG GAG GCG GGG CAA CGG CTG          2112
Gln Gln Pro Pro Arg Leu Pro Pro Glu Val Glu Ala Gly Gln Arg Leu
690                 695                 700

CGC GCA GGG GCA GCT GGT GGA GCT GCA CAT CAT CAT CAT CAT CAT              2157
Arg Ala Gly Ala Ala Gly Gly Ala Ala His His His His His His
705                 710                 715

TGA                                                                      2160
```

(2) INFORMATION FOR SEQ ID NO:12:

(i) SEQUENCE CHARACTERISTICS:
        (A) LENGTH: 719 amino acids
        (B) TYPE: amino acid
        (D) TOPOLOGY: linear (ii) MOLECULE TYPE: protein (xi) SEQUENCE DESCRIPTION: SEQ ID NO:12:

```
Met Glu Leu Arg Pro Trp Leu Leu Trp Val Val Ala Ala Thr Gly Thr
1               5                   10                  15

Leu Val Leu Leu Ala Ala Asp Ala Gln Gly Gln Lys Val Phe Thr Asn
                20                  25                  30

Thr Trp Ala Val Arg Ile Pro Gly Gly Pro Ala Val Ala Asn Ser Val
            35                  40                  45

Ala Arg Lys His Gly Phe Leu Asn Leu Gly Gln Ile Phe Gly Asp Tyr
        50                  55                  60

Tyr His Phe Trp His Arg Gly Val Thr Lys Arg Ser Leu Ser Pro His
```

```
            65                  70                  75                  80
Arg Pro Arg His Ser Arg Leu Gln Arg Glu Pro Gln Val Gln Trp Leu
                    85                  90                  95
Glu Gln Gln Val Ala Lys Arg Arg Thr Lys Arg Asp Val Tyr Gln Glu
                100                 105                 110
Pro Thr Asp Pro Lys Phe Pro Gln Gln Trp Tyr Leu Ser Gly Val Thr
                115                 120                 125
Gln Arg Asp Leu Asn Val Lys Ala Ala Trp Ala Gln Gly Tyr Thr Gly
        130                 135                 140
His Gly Ile Val Val Ser Ile Leu Asp Asp Gly Ile Glu Lys Asn His
145                 150                 155                 160
Pro Asp Leu Ala Gly Asn Tyr Asp Pro Gly Ala Ser Phe Asp Val Asn
                165                 170                 175
Asp Gln Asp Pro Asp Pro Gln Pro Arg Tyr Thr Gln Met Asn Asp Asn
                180                 185                 190
Arg His Gly Thr Arg Cys Ala Gly Glu Val Ala Ala Val Ala Asn Asn
        195                 200                 205
Gly Val Cys Gly Val Gly Val Ala Tyr Asn Ala Arg Ile Gly Gly Val
        210                 215                 220
Arg Met Leu Asp Gly Glu Val Thr Asp Ala Val Glu Ala Arg Ser Leu
225                 230                 235                 240
Gly Leu Asn Pro Asn His Ile His Ile Tyr Ser Ala Ser Trp Gly Pro
                245                 250                 255
Glu Asp Asp Gly Lys Thr Val Asp Gly Pro Ala Arg Leu Ala Glu Glu
                260                 265                 270
Ala Phe Phe Arg Gly Val Ser Gln Gly Arg Gly Gly Leu Gly Ser Ile
        275                 280                 285
Phe Val Trp Ala Ser Gly Asn Gly Gly Arg Glu His Asp Ser Cys Asn
        290                 295                 300
Cys Asp Gly Tyr Thr Asn Ser Ile Tyr Thr Leu Ser Ile Ser Ser Ala
305                 310                 315                 320
Thr Gln Phe Gly Asn Val Pro Trp Tyr Ser Glu Ala Cys Ser Ser Thr
                325                 330                 335
Leu Ala Thr Thr Tyr Ser Ser Gly Asn Gln Asn Glu Lys Gln Ile Val
                340                 345                 350
Thr Thr Asp Leu Arg Gln Lys Cys Thr Glu Ser His Thr Gly Thr Ser
                355                 360                 365
Ala Ser Ala Pro Leu Ala Ala Gly Ile Ile Ala Leu Thr Leu Glu Ala
        370                 375                 380
Asn Lys Asn Leu Thr Trp Arg Asp Met Gln His Leu Val Val Gln Thr
385                 390                 395                 400
Ser Lys Pro Ala His Leu Asn Ala Asn Asp Trp Ala Thr Asn Gly Val
                405                 410                 415
Gly Arg Lys Val Ser His Ser Tyr Gly Tyr Gly Leu Leu Asp Ala Gly
                420                 425                 430
Ala Met Val Ala Leu Ala Gln Asn Trp Thr Thr Val Ala Pro Gln Arg
        435                 440                 445
Lys Cys Ile Ile Asp Ile Leu Thr Glu Pro Lys Asp Ile Gly Lys Arg
        450                 455                 460
Leu Glu Val Arg Lys Thr Val Thr Ala Cys Leu Gly Glu Pro Asn His
465                 470                 475                 480
Ile Thr Arg Leu Glu His Ala Gln Ala Arg Leu Thr Leu Ser Tyr Asn
                485                 490                 495
```

```
Arg Arg Gly Asp Leu Ala Ile His Leu Val Ser Pro Met Gly Thr Arg
            500                 505                 510

Ser Thr Leu Leu Ala Ala Arg Pro His Asp Tyr Ser Ala Asp Gly Phe
            515                 520                 525

Asn Asp Trp Ala Phe Met Thr Thr His Ser Trp Asp Glu Asp Pro Ser
            530                 535                 540

Gly Glu Trp Val Leu Glu Ile Glu Asn Thr Ser Glu Ala Asn Asn Tyr
545                 550                 555                 560

Gly Thr Leu Thr Lys Phe Thr Leu Val Leu Tyr Gly Thr Ala Pro Glu
            565                 570                 575

Gly Leu Pro Val Pro Pro Glu Ser Ser Gly Cys Lys Thr Leu Thr Ser
            580                 585                 590

Ser Gln Ala Cys Val Val Cys Glu Glu Gly Phe Ser Leu His Gln Lys
            595                 600                 605

Ser Cys Val Gln His Cys Pro Pro Gly Phe Ala Pro Gln Val Leu Asp
            610                 615                 620

Thr His Tyr Ser Thr Glu Asn Asp Val Glu Thr Ile Arg Ala Ser Val
625                 630                 635                 640

Cys Ala Pro Cys His Ala Ser Cys Ala Thr Cys Gln Gly Pro Ala Leu
            645                 650                 655

Thr Asp Cys Leu Ser Cys Pro Ser His Ala Ser Leu Asp Pro Val Glu
            660                 665                 670

Gln Thr Cys Ser Arg Gln Ser Gln Ser Ser Arg Glu Ser Pro Pro Gln
            675                 680                 685

Gln Gln Pro Pro Arg Leu Pro Pro Glu Val Glu Ala Gly Gln Arg Leu
690                 695                 700

Arg Ala Gly Ala Ala Gly Gly Ala Ala His His His His His His
705                 710                 715

(2) INFORMATION FOR SEQ ID NO:13:

(i) SEQUENCE CHARACTERISTICS:
        (A) LENGTH: 1758 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..1755

(ix) FEATURE:
        (A) NAME/KEY: mat_peptide
        (B) LOCATION: 1..1755

(xi) SEQUENCE DESCRIPTION: SEQ ID NO:13:

ATG GAG CTG AGG CCC TGG TTG CTA TGG GTG GTA GCA GCA ACA GGA ACC      48
Met Glu Leu Arg Pro Trp Leu Leu Trp Val Val Ala Ala Thr Gly Thr
 1               5                  10                  15

TTG GTC CTG CTA GCA GCT GAT GCT CAG GGC CAG AAG GTC TTC ACC AAC      96
Leu Val Leu Leu Ala Ala Asp Ala Gln Gly Gln Lys Val Phe Thr Asn
                20                  25                  30

ACG TGG GCT GTG CGC ATC CCT GGA GGC CCA GCG GTG GCC AAC AGT GTG     144
Thr Trp Ala Val Arg Ile Pro Gly Gly Pro Ala Val Ala Asn Ser Val
            35                  40                  45

GCA CGG AAG CAT GGG TTC CTC AAC CTG GGC CAG ATC TTC GGG GAC TAT     192
Ala Arg Lys His Gly Phe Leu Asn Leu Gly Gln Ile Phe Gly Asp Tyr
        50                  55                  60
```

```
TAC CAC TTC TGG CAT CGA GGA GTG ACG AAG CGG TCC CTG TCG CCT CAC    240
Tyr His Phe Trp His Arg Gly Val Thr Lys Arg Ser Leu Ser Pro His
 65          70                      75                      80

CGC CCG CGG CAC AGC CGG CTG CAG AGG GAG CCT CAA GTA CAG TGG CTG    288
Arg Pro Arg His Ser Arg Leu Gln Arg Glu Pro Gln Val Gln Trp Leu
                 85                      90                  95

GAA CAG CAG GTG GCA AAG CGA CGG ACT AAA CGG GAC GTG TAC CAG GAG    336
Glu Gln Gln Val Ala Lys Arg Arg Thr Lys Arg Asp Val Tyr Gln Glu
            100                     105                 110

CCC ACA GAC CCC AAG TTT CCT CAG CAG TGG TAC CTG TCT GGT GTC ACT    384
Pro Thr Asp Pro Lys Phe Pro Gln Gln Trp Tyr Leu Ser Gly Val Thr
        115                     120                 125

CAG CGG GAC CTG AAT GTG AAG GCG GCC TGG GCG CAG GGC TAC ACA GGG    432
Gln Arg Asp Leu Asn Val Lys Ala Ala Trp Ala Gln Gly Tyr Thr Gly
    130                     135                 140

CAC GGC ATT GTG GTC TCC ATT CTG GAC GAT GGC ATC GAG AAG AAC CAC    480
His Gly Ile Val Val Ser Ile Leu Asp Asp Gly Ile Glu Lys Asn His
145                     150                 155                 160

CCG GAC TTG GCA GGC AAT TAT GAT CCT GGG GCC AGT TTT GAT GTC AAT    528
Pro Asp Leu Ala Gly Asn Tyr Asp Pro Gly Ala Ser Phe Asp Val Asn
                165                 170                 175

GAC CAG GAC CCT GAC CCC CAG CCT CGG TAC ACA CAG ATG AAT GAC AAC    576
Asp Gln Asp Pro Asp Pro Gln Pro Arg Tyr Thr Gln Met Asn Asp Asn
            180                 185                 190

AGG CAC GGC ACA CGG TGT GCG GGG GAA GTG GCT GCG GTG GCC AAC AAC    624
Arg His Gly Thr Arg Cys Ala Gly Glu Val Ala Ala Val Ala Asn Asn
        195                 200                 205

GGT GTC TGT GGT GTA GGT GTG GCC TAC AAC GCC CGC ATT GGA GGG GTG    672
Gly Val Cys Gly Val Gly Val Ala Tyr Asn Ala Arg Ile Gly Gly Val
    210                 215                 220

CGC ATG CTG GAT GGC GAG GTG ACA GAT GCA GTG GAG GCA CGC TCG CTG    720
Arg Met Leu Asp Gly Glu Val Thr Asp Ala Val Glu Ala Arg Ser Leu
225                 230                 235                 240

GGC CTG AAC CCC AAC CAC ATC CAC ATC TAC AGT GCC AGC TGG GGC CCC    768
Gly Leu Asn Pro Asn His Ile His Ile Tyr Ser Ala Ser Trp Gly Pro
                245                 250                 255

GAG GAT GAC GGC AAG ACA GTG GAT GGG CCA GCC CGC CTC GCC GAG GAG    816
Glu Asp Asp Gly Lys Thr Val Asp Gly Pro Ala Arg Leu Ala Glu Glu
            260                 265                 270

GCC TTC TTC CGT GGG GTT AGC CAG GGC CGA GGG GGG CTG GGC TCC ATC    864
Ala Phe Phe Arg Gly Val Ser Gln Gly Arg Gly Gly Leu Gly Ser Ile
        275                 280                 285

TTT GTC TGG GCC TCG GGG AAC GGG GGC CGG GAA CAT GAC AGC TGC AAC    912
Phe Val Trp Ala Ser Gly Asn Gly Gly Arg Glu His Asp Ser Cys Asn
    290                 295                 300

TGC GAC GGC TAC ACC AAC AGT ATC TAC ACG CTG TCC ATC AGC AGC GCC    960
Cys Asp Gly Tyr Thr Asn Ser Ile Tyr Thr Leu Ser Ile Ser Ser Ala
305                 310                 315                 320

ACG CAG TTT GGC AAC GTG CCG TGG TAC AGC GAG GCC TGC TCG TCC ACA   1008
Thr Gln Phe Gly Asn Val Pro Trp Tyr Ser Glu Ala Cys Ser Ser Thr
                325                 330                 335

CTG GCC ACG ACC TAC AGC AGT GGC AAC CAG AAT GAG AAG CAG ATC GTG   1056
Leu Ala Thr Thr Tyr Ser Ser Gly Asn Gln Asn Glu Lys Gln Ile Val
            340                 345                 350

ACG ACT GAC TTG CGG CAG AAG TGC ACG GAG TCT CAC ACG GGC ACC TCA   1104
Thr Thr Asp Leu Arg Gln Lys Cys Thr Glu Ser His Thr Gly Thr Ser
        355                 360                 365

GCC TCT GCC CCC TTA GCA GCC GGC ATC ATT GCT CTC ACC CTG GAG GCC   1152
Ala Ser Ala Pro Leu Ala Ala Gly Ile Ile Ala Leu Thr Leu Glu Ala
```

```
                370                 375                 380
AAT AAG AAC CTC ACA TGG CGG GAC ATG CAA CAC CTG GTG GTA CAG ACC      1200
Asn Lys Asn Leu Thr Trp Arg Asp Met Gln His Leu Val Val Gln Thr
385                 390                 395                 400

TCG AAG CCA GCC CAC CTC AAT GCC AAC GAC TGG GCC ACC AAT GGT GTG      1248
Ser Lys Pro Ala His Leu Asn Ala Asn Asp Trp Ala Thr Asn Gly Val
                405                 410                 415

GGC CGG AAA GTG AGC CAC TCA TAT GGC TAC GGG CTT TTG GAC GCA GGC      1296
Gly Arg Lys Val Ser His Ser Tyr Gly Tyr Gly Leu Leu Asp Ala Gly
                420                 425                 430

GCC ATG GTG GCC CTG GCC CAG AAT TGG ACC ACA GTG GCC CCC CAG CGG      1344
Ala Met Val Ala Leu Ala Gln Asn Trp Thr Thr Val Ala Pro Gln Arg
                435                 440                 445

AAG TGC ATC ATC GAC ATC CTC ACC GAG CCC AAA GAC ATC GGG AAA CGG      1392
Lys Cys Ile Ile Asp Ile Leu Thr Glu Pro Lys Asp Ile Gly Lys Arg
        450                 455                 460

CTC GAG GTG CGG AAG ACC GTG ACC GCG TGC CTG GGC GAG CCC AAC CAC      1440
Leu Glu Val Arg Lys Thr Val Thr Ala Cys Leu Gly Glu Pro Asn His
465                 470                 475                 480

ATC ACT CGG CTG GAG CAC GCT CAG GCG CGG CTC ACC CTG TCC TAT AAT      1488
Ile Thr Arg Leu Glu His Ala Gln Ala Arg Leu Thr Leu Ser Tyr Asn
                485                 490                 495

CGC CGT GGC GAC CTG GCC ATC CAC CTG GTC AGC CCC ATG GGC ACC CGC      1536
Arg Arg Gly Asp Leu Ala Ile His Leu Val Ser Pro Met Gly Thr Arg
        500                 505                 510

TCC ACC CTG CTG GCA GCC AGG CCA CAT GAC TAC TCC GCA GAT GGG TTT      1584
Ser Thr Leu Leu Ala Ala Arg Pro His Asp Tyr Ser Ala Asp Gly Phe
        515                 520                 525

AAT GAC TGG GCC TTC ATG ACA ACT CAT TCC TGG GAT GAG GAT CCC TCT      1632
Asn Asp Trp Ala Phe Met Thr Thr His Ser Trp Asp Glu Asp Pro Ser
530                 535                 540

GGC GAG TGG GTC CTA GAG ATT GAA AAC ACC AGC GAA GCC AAC AAC TAT      1680
Gly Glu Trp Val Leu Glu Ile Glu Asn Thr Ser Glu Ala Asn Asn Tyr
545                 550                 555                 560

GGG ACG CTG ACC AAG TTC ACC CTC GTA CTC TAT GGC ACC GCC CCT GAG      1728
Gly Thr Leu Thr Lys Phe Thr Leu Val Leu Tyr Gly Thr Ala Pro Glu
                565                 570                 575

GGG CTG CCC GTA CCT CCA GAA AGC AGT TAG                              1758
Gly Leu Pro Val Pro Pro Glu Ser Ser
                580                 585

(2) INFORMATION FOR SEQ ID NO:14:

(i) SEQUENCE CHARACTERISTICS:
        (A) LENGTH: 585 amino acids
        (B) TYPE: amino acid
        (D) TOPOLOGY: linear (ii) MOLECULE TYPE: protein (xi) SEQUENCE DESCRIPTION: SEQ ID NO:14:

Met Glu Leu Arg Pro Trp Leu Leu Trp Val Val Ala Ala Thr Gly Thr
1               5                   10                  15

Leu Val Leu Leu Ala Ala Asp Ala Gln Gly Gln Lys Val Phe Thr Asn
            20                  25                  30

Thr Trp Ala Val Arg Ile Pro Gly Gly Pro Ala Val Ala Asn Ser Val
        35                  40                  45

Ala Arg Lys His Gly Phe Leu Asn Leu Gly Gln Ile Phe Gly Asp Tyr
    50                  55                  60

Tyr His Phe Trp His Arg Gly Val Thr Lys Arg Ser Leu Ser Pro His
```

```
                65                  70                  75                  80
            Arg Pro Arg His Ser Arg Leu Gln Arg Glu Pro Gln Val Gln Trp Leu
                                85                  90                  95
            Glu Gln Gln Val Ala Lys Arg Arg Thr Lys Arg Asp Val Tyr Gln Glu
                            100                 105                 110
            Pro Thr Asp Pro Lys Phe Pro Gln Gln Trp Tyr Leu Ser Gly Val Thr
                            115                 120                 125
            Gln Arg Asp Leu Asn Val Lys Ala Ala Trp Ala Gln Gly Tyr Thr Gly
                        130                 135                 140
            His Gly Ile Val Val Ser Ile Leu Asp Asp Gly Ile Glu Lys Asn His
            145                 150                 155                 160
            Pro Asp Leu Ala Gly Asn Tyr Asp Pro Gly Ala Ser Phe Asp Val Asn
                            165                 170                 175
            Asp Gln Asp Pro Asp Pro Gln Pro Arg Tyr Thr Gln Met Asn Asp Asn
                        180                 185                 190
            Arg His Gly Thr Arg Cys Ala Gly Glu Val Ala Ala Val Ala Asn Asn
                        195                 200                 205
            Gly Val Cys Gly Val Gly Val Ala Tyr Asn Ala Arg Ile Gly Gly Val
                        210                 215                 220
            Arg Met Leu Asp Gly Glu Val Thr Asp Ala Val Glu Ala Arg Ser Leu
            225                 230                 235                 240
            Gly Leu Asn Pro Asn His Ile His Ile Tyr Ser Ala Ser Trp Gly Pro
                            245                 250                 255
            Glu Asp Asp Gly Lys Thr Val Asp Gly Pro Ala Arg Leu Ala Glu Glu
                        260                 265                 270
            Ala Phe Phe Arg Gly Val Ser Gln Gly Arg Gly Leu Gly Ser Ile
                    275                 280                 285
            Phe Val Trp Ala Ser Gly Asn Gly Gly Arg Glu His Asp Ser Cys Asn
                        290                 295                 300
            Cys Asp Gly Tyr Thr Asn Ser Ile Tyr Thr Leu Ser Ile Ser Ser Ala
            305                 310                 315                 320
            Thr Gln Phe Gly Asn Val Pro Trp Tyr Ser Glu Ala Cys Ser Ser Thr
                            325                 330                 335
            Leu Ala Thr Thr Tyr Ser Ser Gly Asn Gln Asn Glu Lys Gln Ile Val
                        340                 345                 350
            Thr Thr Asp Leu Arg Gln Lys Cys Thr Glu Ser His Thr Gly Thr Ser
                        355                 360                 365
            Ala Ser Ala Pro Leu Ala Ala Gly Ile Ile Ala Leu Thr Leu Glu Ala
                    370                 375                 380
            Asn Lys Asn Leu Thr Trp Arg Asp Met Gln His Leu Val Val Gln Thr
            385                 390                 395                 400
            Ser Lys Pro Ala His Leu Asn Ala Asn Asp Trp Ala Thr Asn Gly Val
                            405                 410                 415
            Gly Arg Lys Val Ser His Ser Tyr Gly Tyr Gly Leu Leu Asp Ala Gly
                        420                 425                 430
            Ala Met Val Ala Leu Ala Gln Asn Trp Thr Thr Val Ala Pro Gln Arg
                    435                 440                 445
            Lys Cys Ile Ile Asp Ile Leu Thr Glu Pro Lys Asp Ile Gly Lys Arg
                450                 455                 460
            Leu Glu Val Arg Lys Thr Val Thr Ala Cys Leu Gly Glu Pro Asn His
            465                 470                 475                 480
            Ile Thr Arg Leu Glu His Ala Gln Ala Arg Leu Thr Leu Ser Tyr Asn
                            485                 490                 495
```

```
Arg Arg Gly Asp Leu Ala Ile His Leu Val Ser Pro Met Gly Thr Arg
            500                 505                 510

Ser Thr Leu Leu Ala Ala Arg Pro His Asp Tyr Ser Ala Asp Gly Phe
        515                 520                 525

Asn Asp Trp Ala Phe Met Thr Thr His Ser Trp Asp Glu Asp Pro Ser
    530                 535                 540

Gly Glu Trp Val Leu Glu Ile Glu Asn Thr Ser Glu Ala Asn Asn Tyr
545                 550                 555                 560

Gly Thr Leu Thr Lys Phe Thr Leu Val Leu Tyr Gly Thr Ala Pro Glu
                565                 570                 575

Gly Leu Pro Val Pro Pro Glu Ser Ser
            580                 585
```

(2) INFORMATION FOR SEQ ID NO:15:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:15:

```
CTAGAATTCT AACTGCTTTC TGGAGGTACG GGCAG                         35
```

(2) INFORMATION FOR SEQ ID NO:16:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:16:

```
CTAGAATTCT TAGTGGTGAT GGTGATGATG ACTGCTTTCT GGAGGTACGG GCAG    54
```

(2) INFORMATION FOR SEQ ID NO:17:

(i) SEQUENCE CHARACTERISTICS:
        (A) LENGTH: 1776 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..1773

(ix) FEATURE:
        (A) NAME/KEY: mat_peptide
        (B) LOCATION: 1..1773

(xi) SEQUENCE DESCRIPTION: SEQ ID NO:17:

```
ATG GAG CTG AGG CCC TGG TTG CTA TGG GTG GTA GCA GCA ACA GGA ACC    48
Met Glu Leu Arg Pro Trp Leu Leu Trp Val Val Ala Ala Thr Gly Thr
 1               5                  10                  15

TTG GTC CTG CTA GCA GCT GAT GCT CAG GGC CAG AAG GTC TTC ACC AAC    96
Leu Val Leu Leu Ala Ala Asp Ala Gln Gly Gln Lys Val Phe Thr Asn
                20                  25                  30

ACG TGG GCT GTG CGC ATC CCT GGA GGC CCA GCG GTG GCC AAC AGT GTG   144
```

```
Thr Trp Ala Val Arg Ile Pro Gly Gly Pro Ala Val Ala Asn Ser Val
         35                  40                  45

GCA CGG AAG CAT GGG TTC CTC AAC CTG GGC CAG ATC TTC GGG GAC TAT       192
Ala Arg Lys His Gly Phe Leu Asn Leu Gly Gln Ile Phe Gly Asp Tyr
     50                  55                  60

TAC CAC TTC TGG CAT CGA GGA GTG ACG AAG CGG TCC CTG TCG CCT CAC       240
Tyr His Phe Trp His Arg Gly Val Thr Lys Arg Ser Leu Ser Pro His
 65                  70                  75                  80

CGC CCG CGG CAC AGC CGG CTG CAG AGG GAG CCT CAA GTA CAG TGG CTG       288
Arg Pro Arg His Ser Arg Leu Gln Arg Glu Pro Gln Val Gln Trp Leu
                 85                  90                  95

GAA CAG CAG GTG GCA AAG CGA CGG ACT AAA CGG GAC GTG TAC CAG GAG       336
Glu Gln Gln Val Ala Lys Arg Arg Thr Lys Arg Asp Val Tyr Gln Glu
             100                 105                 110

CCC ACA GAC CCC AAG TTT CCT CAG CAG TGG TAC CTG TCT GGT GTC ACT       384
Pro Thr Asp Pro Lys Phe Pro Gln Gln Trp Tyr Leu Ser Gly Val Thr
         115                 120                 125

CAG CGG GAC CTG AAT GTG AAG GCG GCC TGG GCG CAG GGC TAC ACA GGG       432
Gln Arg Asp Leu Asn Val Lys Ala Ala Trp Ala Gln Gly Tyr Thr Gly
     130                 135                 140

CAC GGC ATT GTG GTC TCC ATT CTG GAC GAT GGC ATC GAG AAG AAC CAC       480
His Gly Ile Val Val Ser Ile Leu Asp Asp Gly Ile Glu Lys Asn His
145                 150                 155                 160

CCG GAC TTG GCA GGC AAT TAT GAT CCT GGG GCC AGT TTT GAT GTC AAT       528
Pro Asp Leu Ala Gly Asn Tyr Asp Pro Gly Ala Ser Phe Asp Val Asn
                 165                 170                 175

GAC CAG GAC CCT GAC CCC CAG CCT CGG TAC ACA CAG ATG AAT GAC AAC       576
Asp Gln Asp Pro Asp Pro Gln Pro Arg Tyr Thr Gln Met Asn Asp Asn
             180                 185                 190

AGG CAC GGC ACA CGG TGT GCG GGG GAA GTG GCT GCG GTG GCC AAC AAC       624
Arg His Gly Thr Arg Cys Ala Gly Glu Val Ala Ala Val Ala Asn Asn
         195                 200                 205

GGT GTC TGT GGT GTA GGT GTG GCC TAC AAC GCC CGC ATT GGA GGG GTG       672
Gly Val Cys Gly Val Gly Val Ala Tyr Asn Ala Arg Ile Gly Gly Val
     210                 215                 220

CGC ATG CTG GAT GGC GAG GTG ACA GAT GCA GTG GAG GCA CGC TCG CTG       720
Arg Met Leu Asp Gly Glu Val Thr Asp Ala Val Glu Ala Arg Ser Leu
225                 230                 235                 240

GGC CTG AAC CCC AAC CAC ATC CAC ATC TAC AGT GCC AGC TGG GGC CCC       768
Gly Leu Asn Pro Asn His Ile His Ile Tyr Ser Ala Ser Trp Gly Pro
                 245                 250                 255

GAG GAT GAC GGC AAG ACA GTG GAT GGG CCA GCC CGC CTC GCC GAG GAG       816
Glu Asp Asp Gly Lys Thr Val Asp Gly Pro Ala Arg Leu Ala Glu Glu
             260                 265                 270

GCC TTC TTC CGT GGG GTT AGC CAG GGC CGA GGG GGG CTG GGC TCC ATC       864
Ala Phe Phe Arg Gly Val Ser Gln Gly Arg Gly Gly Leu Gly Ser Ile
         275                 280                 285

TTT GTC TGG GCC TCG GGG AAC GGG GGC CGG GAA CAT GAC AGC TGC AAC       912
Phe Val Trp Ala Ser Gly Asn Gly Gly Arg Glu His Asp Ser Cys Asn
     290                 295                 300

TGC GAC GGC TAC ACC AAC AGT ATC TAC ACG CTG TCC ATC AGC AGC GCC       960
Cys Asp Gly Tyr Thr Asn Ser Ile Tyr Thr Leu Ser Ile Ser Ser Ala
305                 310                 315                 320

ACG CAG TTT GGC AAC GTG CCG TGG TAC AGC GAG GCC TGC TCG TCC ACA      1008
Thr Gln Phe Gly Asn Val Pro Trp Tyr Ser Glu Ala Cys Ser Ser Thr
                 325                 330                 335

CTG GCC ACG ACC TAC AGC AGT GGC AAC CAG AAT GAG AAG CAG ATC GTG      1056
Leu Ala Thr Thr Tyr Ser Ser Gly Asn Gln Asn Glu Lys Gln Ile Val
             340                 345                 350
```

```
ACG ACT GAC TTG CGG CAG AAG TGC ACG GAG TCT CAC ACG GGC ACC TCA      1104
Thr Thr Asp Leu Arg Gln Lys Cys Thr Glu Ser His Thr Gly Thr Ser
        355                 360                 365

GCC TCT GCC CCC TTA GCA GCC GGC ATC ATT GCT CTC ACC CTG GAG GCC      1152
Ala Ser Ala Pro Leu Ala Ala Gly Ile Ile Ala Leu Thr Leu Glu Ala
370                 375                 380

AAT AAG AAC CTC ACA TGG CGG GAC ATG CAA CAC CTG GTG GTA CAG ACC      1200
Asn Lys Asn Leu Thr Trp Arg Asp Met Gln His Leu Val Val Gln Thr
385                 390                 395                 400

TCG AAG CCA GCC CAC CTC AAT GCC AAC GAC TGG GCC ACC AAT GGT GTG      1248
Ser Lys Pro Ala His Leu Asn Ala Asn Asp Trp Ala Thr Asn Gly Val
            405                 410                 415

GGC CGG AAA GTG AGC CAC TCA TAT GGC TAC GGG CTT TTG GAC GCA GGC      1296
Gly Arg Lys Val Ser His Ser Tyr Gly Tyr Gly Leu Leu Asp Ala Gly
                420                 425                 430

GCC ATG GTG GCC CTG GCC CAG AAT TGG ACC ACA GTG GCC CCC CAG CGG      1344
Ala Met Val Ala Leu Ala Gln Asn Trp Thr Thr Val Ala Pro Gln Arg
            435                 440                 445

AAG TGC ATC ATC GAC ATC CTC ACC GAG CCC AAA GAC ATC GGG AAA CGG      1392
Lys Cys Ile Ile Asp Ile Leu Thr Glu Pro Lys Asp Ile Gly Lys Arg
        450                 455                 460

CTC GAG GTG CGG AAG ACC GTG ACC GCG TGC CTG GGC GAG CCC AAC CAC      1440
Leu Glu Val Arg Lys Thr Val Thr Ala Cys Leu Gly Glu Pro Asn His
465                 470                 475                 480

ATC ACT CGG CTG GAG CAC GCT CAG GCG CGG CTC ACC CTG TCC TAT AAT      1488
Ile Thr Arg Leu Glu His Ala Gln Ala Arg Leu Thr Leu Ser Tyr Asn
                485                 490                 495

CGC CGT GGC GAC CTG GCC ATC CAC CTG GTC AGC CCC ATG GGC ACC CGC      1536
Arg Arg Gly Asp Leu Ala Ile His Leu Val Ser Pro Met Gly Thr Arg
            500                 505                 510

TCC ACC CTG CTG GCA GCC AGG CCA CAT GAC TAC TCC GCA GAT GGG TTT      1584
Ser Thr Leu Leu Ala Ala Arg Pro His Asp Tyr Ser Ala Asp Gly Phe
        515                 520                 525

AAT GAC TGG GCC TTC ATG ACA ACT CAT TCC TGG GAT GAG GAT CCC TCT      1632
Asn Asp Trp Ala Phe Met Thr Thr His Ser Trp Asp Glu Asp Pro Ser
530                 535                 540

GGC GAG TGG GTC CTA GAG ATT GAA AAC ACC AGC GAA GCC AAC AAC TAT      1680
Gly Glu Trp Val Leu Glu Ile Glu Asn Thr Ser Glu Ala Asn Asn Tyr
545                 550                 555                 560

GGG ACG CTG ACC AAG TTC ACC CTC GTA CTC TAT GGC ACC GCC CCT GAG      1728
Gly Thr Leu Thr Lys Phe Thr Leu Val Leu Tyr Gly Thr Ala Pro Glu
                565                 570                 575

GGG CTG CCC GTA CCT CCA GAA AGC AGT CAT CAT CAC CAT CAC CAC          1773
Gly Leu Pro Val Pro Pro Glu Ser Ser His His His His His His
            580                 585                 590

TAA                                                                   1776
```

(2) INFORMATION FOR SEQ ID NO:18:

(i) SEQUENCE CHARACTERISTICS:
        (A) LENGTH: 591 amino acids
        (B) TYPE: amino acid
        (D) TOPOLOGY: linear (ii) MOLECULE TYPE: protein (xi) SEQUENCE DESCRIPTION: SEQ ID NO:18:

```
Met Glu Leu Arg Pro Trp Leu Leu Trp Val Val Ala Ala Thr Gly Thr
1               5                   10                  15

Leu Val Leu Leu Ala Ala Asp Ala Gln Gly Gln Lys Val Phe Thr Asn
            20                  25                  30
```

```
Thr Trp Ala Val Arg Ile Pro Gly Gly Pro Ala Val Ala Asn Ser Val
         35                  40                  45
Ala Arg Lys His Gly Phe Leu Asn Leu Gly Gln Ile Phe Gly Asp Tyr
     50                  55                  60
Tyr His Phe Trp His Arg Gly Val Thr Lys Arg Ser Leu Ser Pro His
 65                  70                  75                  80
Arg Pro Arg His Ser Arg Leu Gln Arg Glu Pro Gln Val Gln Trp Leu
                 85                  90                  95
Glu Gln Gln Val Ala Lys Arg Arg Thr Lys Arg Asp Val Tyr Gln Glu
             100                 105                 110
Pro Thr Asp Pro Lys Phe Pro Gln Gln Trp Tyr Leu Ser Gly Val Thr
         115                 120                 125
Gln Arg Asp Leu Asn Val Lys Ala Ala Trp Ala Gln Gly Tyr Thr Gly
     130                 135                 140
His Gly Ile Val Val Ser Ile Leu Asp Asp Gly Ile Glu Lys Asn His
145                 150                 155                 160
Pro Asp Leu Ala Gly Asn Tyr Asp Pro Gly Ala Ser Phe Asp Val Asn
                 165                 170                 175
Asp Gln Asp Pro Asp Pro Gln Pro Arg Tyr Thr Gln Met Asn Asp Asn
             180                 185                 190
Arg His Gly Thr Arg Cys Ala Gly Glu Val Ala Ala Val Ala Asn Asn
         195                 200                 205
Gly Val Cys Gly Val Gly Val Ala Tyr Asn Ala Arg Ile Gly Gly Val
     210                 215                 220
Arg Met Leu Asp Gly Glu Val Thr Asp Ala Val Glu Ala Arg Ser Leu
225                 230                 235                 240
Gly Leu Asn Pro Asn His Ile His Ile Tyr Ser Ala Ser Trp Gly Pro
                 245                 250                 255
Glu Asp Asp Gly Lys Thr Val Asp Gly Pro Ala Arg Leu Ala Glu Glu
             260                 265                 270
Ala Phe Phe Arg Gly Val Ser Gln Gly Arg Gly Gly Leu Gly Ser Ile
         275                 280                 285
Phe Val Trp Ala Ser Gly Asn Gly Gly Arg Glu His Asp Ser Cys Asn
     290                 295                 300
Cys Asp Gly Tyr Thr Asn Ser Ile Tyr Thr Leu Ser Ile Ser Ser Ala
305                 310                 315                 320
Thr Gln Phe Gly Asn Val Pro Trp Tyr Ser Glu Ala Cys Ser Ser Thr
                 325                 330                 335
Leu Ala Thr Thr Tyr Ser Ser Gly Asn Gln Asn Glu Lys Gln Ile Val
             340                 345                 350
Thr Thr Asp Leu Arg Gln Lys Cys Thr Glu Ser His Thr Gly Thr Ser
         355                 360                 365
Ala Ser Ala Pro Leu Ala Ala Gly Ile Ile Ala Leu Thr Leu Glu Ala
     370                 375                 380
Asn Lys Asn Leu Thr Trp Arg Asp Met Gln His Leu Val Val Gln Thr
385                 390                 395                 400
Ser Lys Pro Ala His Leu Asn Ala Asn Asp Trp Ala Thr Asn Gly Val
                 405                 410                 415
Gly Arg Lys Val Ser His Ser Tyr Gly Tyr Gly Leu Leu Asp Ala Gly
             420                 425                 430
Ala Met Val Ala Leu Ala Gln Asn Trp Thr Thr Val Ala Pro Gln Arg
         435                 440                 445
```

```
Lys Cys Ile Ile Asp Ile Leu Thr Glu Pro Lys Asp Ile Gly Lys Arg
    450                 455                 460

Leu Glu Val Arg Lys Thr Val Thr Ala Cys Leu Gly Glu Pro Asn His
465                 470                 475                 480

Ile Thr Arg Leu Glu His Ala Gln Ala Arg Leu Thr Leu Ser Tyr Asn
                485                 490                 495

Arg Arg Gly Asp Leu Ala Ile His Leu Val Ser Pro Met Gly Thr Arg
            500                 505                 510

Ser Thr Leu Leu Ala Ala Arg Pro His Asp Tyr Ser Ala Asp Gly Phe
        515                 520                 525

Asn Asp Trp Ala Phe Met Thr Thr His Ser Trp Asp Glu Asp Pro Ser
    530                 535                 540

Gly Glu Trp Val Leu Glu Ile Glu Asn Thr Ser Glu Ala Asn Asn Tyr
545                 550                 555                 560

Gly Thr Leu Thr Lys Phe Thr Leu Val Leu Tyr Gly Thr Ala Pro Glu
                565                 570                 575

Gly Leu Pro Val Pro Pro Glu Ser Ser His His His His His His
            580                 585                 590
```

(2) INFORMATION FOR SEQ ID NO:19:

(i) SEQUENCE CHARACTERISTICS:
        (A) LENGTH: 72 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:19:

```
CTAGAATTCT TAGTGGTGAT GGTGATGATG TGCAGCTCCA CCAGCTGCAC TGCTTTCTGG    60

AGGTACGGGC AG                                                       72
```

(2) INFORMATION FOR SEQ ID NO:20:

(i) SEQUENCE CHARACTERISTICS:
        (A) LENGTH: 1794 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..1791

(ix) FEATURE:
        (A) NAME/KEY: mat_peptide
        (B) LOCATION: 1..1791

(xi) SEQUENCE DESCRIPTION: SEQ ID NO:20:

```
ATG GAG CTG AGG CCC TGG TTG CTA TGG GTG GTA GCA GCA ACA GGA ACC     48
Met Glu Leu Arg Pro Trp Leu Leu Trp Val Val Ala Ala Thr Gly Thr
  1               5                  10                  15

TTG GTC CTG CTA GCA GCT GAT GCT CAG GGC CAG AAG GTC TTC ACC AAC     96
Leu Val Leu Leu Ala Ala Asp Ala Gln Gly Gln Lys Val Phe Thr Asn
             20                  25                  30

ACG TGG GCT GTG CGC ATC CCT GGA GGC CCA GCG GTG GCC AAC AGT GTG    144
Thr Trp Ala Val Arg Ile Pro Gly Gly Pro Ala Val Ala Asn Ser Val
         35                  40                  45

GCA CGG AAG CAT GGG TTC CTC AAC CTG GGC CAG ATC TTC GGG GAC TAT    192
Ala Arg Lys His Gly Phe Leu Asn Leu Gly Gln Ile Phe Gly Asp Tyr
```

```
            50                      55                      60
TAC CAC TTC TGG CAT CGA GGA GTG ACG AAG CGG TCC CTG TCG CCT CAC      240
Tyr His Phe Trp His Arg Gly Val Thr Lys Arg Ser Leu Ser Pro His
 65                      70                      75                  80

CGC CCG CGG CAC AGC CGG CTG CAG AGG GAG CCT CAA GTA CAG TGG CTG      288
Arg Pro Arg His Ser Arg Leu Gln Arg Glu Pro Gln Val Gln Trp Leu
                     85                      90                      95

GAA CAG CAG GTG GCA AAG CGA CGG ACT AAA CGG GAC GTG TAC CAG GAG      336
Glu Gln Gln Val Ala Lys Arg Arg Thr Lys Arg Asp Val Tyr Gln Glu
                100                     105                     110

CCC ACA GAC CCC AAG TTT CCT CAG CAG TGG TAC CTG TCT GGT GTC ACT      384
Pro Thr Asp Pro Lys Phe Pro Gln Gln Trp Tyr Leu Ser Gly Val Thr
            115                     120                     125

CAG CGG GAC CTG AAT GTG AAG GCG GCC TGG GCG CAG GGC TAC ACA GGG      432
Gln Arg Asp Leu Asn Val Lys Ala Ala Trp Ala Gln Gly Tyr Thr Gly
            130                     135                     140

CAC GGC ATT GTG GTC TCC ATT CTG GAC GAT GGC ATC GAG AAG AAC CAC      480
His Gly Ile Val Val Ser Ile Leu Asp Asp Gly Ile Glu Lys Asn His
145                     150                     155                 160

CCG GAC TTG GCA GGC AAT TAT GAT CCT GGG GCC AGT TTT GAT GTC AAT      528
Pro Asp Leu Ala Gly Asn Tyr Asp Pro Gly Ala Ser Phe Asp Val Asn
                    165                     170                     175

GAC CAG GAC CCT GAC CCC CAG CCT CGG TAC ACA CAG ATG AAT GAC AAC      576
Asp Gln Asp Pro Asp Pro Gln Pro Arg Tyr Thr Gln Met Asn Asp Asn
                180                     185                     190

AGG CAC GGC ACA CGG TGT GCG GGG GAA GTG GCT GCG GTG GCC AAC AAC      624
Arg His Gly Thr Arg Cys Ala Gly Glu Val Ala Ala Val Ala Asn Asn
            195                     200                     205

GGT GTC TGT GGT GTA GGT GTG GCC TAC AAC GCC CGC ATT GGA GGG GTG      672
Gly Val Cys Gly Val Gly Val Ala Tyr Asn Ala Arg Ile Gly Gly Val
210                     215                     220

CGC ATG CTG GAT GGC GAG GTG ACA GAT GCA GTG GAG GCA CGC TCG CTG      720
Arg Met Leu Asp Gly Glu Val Thr Asp Ala Val Glu Ala Arg Ser Leu
225                     230                     235                 240

GGC CTG AAC CCC AAC CAC ATC CAC ATC TAC AGT GCC AGC TGG GGC CCC      768
Gly Leu Asn Pro Asn His Ile His Ile Tyr Ser Ala Ser Trp Gly Pro
                    245                     250                     255

GAG GAT GAC GGC AAG ACA GTG GAT GGG CCA GCC CGC CTC GCC GAG GAG      816
Glu Asp Asp Gly Lys Thr Val Asp Gly Pro Ala Arg Leu Ala Glu Glu
                260                     265                     270

GCC TTC TTC CGT GGG GTT AGC CAG GGC CGA GGG GGG CTG GGC TCC ATC      864
Ala Phe Phe Arg Gly Val Ser Gln Gly Arg Gly Gly Leu Gly Ser Ile
            275                     280                     285

TTT GTC TGG GCC TCG GGG AAC GGG GGC CGG GAA CAT GAC AGC TGC AAC      912
Phe Val Trp Ala Ser Gly Asn Gly Gly Arg Glu His Asp Ser Cys Asn
            290                     295                     300

TGC GAC GGC TAC ACC AAC AGT ATC TAC ACG CTG TCC ATC AGC AGC GCC      960
Cys Asp Gly Tyr Thr Asn Ser Ile Tyr Thr Leu Ser Ile Ser Ser Ala
305                     310                     315                 320

ACG CAG TTT GGC AAC GTG CCG TGG TAC AGC GAG GCC TGC TCG TCC ACA     1008
Thr Gln Phe Gly Asn Val Pro Trp Tyr Ser Glu Ala Cys Ser Ser Thr
                    325                     330                     335

CTG GCC ACG ACC TAC AGC AGT GGC AAC CAG AAT GAG AAG CAG ATC GTG     1056
Leu Ala Thr Thr Tyr Ser Ser Gly Asn Gln Asn Glu Lys Gln Ile Val
                340                     345                     350

ACG ACT GAC TTG CGG CAG AAG TGC ACG GAG TCT CAC ACG GGC ACC TCA     1104
Thr Thr Asp Leu Arg Gln Lys Cys Thr Glu Ser His Thr Gly Thr Ser
            355                     360                     365

GCC TCT GCC CCC TTA GCA GCC GGC ATC ATT GCT CTC ACC CTG GAG GCC     1152
```

```
Ala Ser Ala Pro Leu Ala Ala Gly Ile Ile Ala Leu Thr Leu Glu Ala
        370                 375                 380

AAT AAG AAC CTC ACA TGG CGG GAC ATG CAA CAC CTG GTG GTA CAG ACC    1200
Asn Lys Asn Leu Thr Trp Arg Asp Met Gln His Leu Val Val Gln Thr
385                 390                 395                 400

TCG AAG CCA GCC CAC CTC AAT GCC AAC GAC TGG GCC ACC AAT GGT GTG    1248
Ser Lys Pro Ala His Leu Asn Ala Asn Asp Trp Ala Thr Asn Gly Val
                405                 410                 415

GGC CGG AAA GTG AGC CAC TCA TAT GGC TAC GGG CTT TTG GAC GCA GGC    1296
Gly Arg Lys Val Ser His Ser Tyr Gly Tyr Gly Leu Leu Asp Ala Gly
            420                 425                 430

GCC ATG GTG GCC CTG GCC CAG AAT TGG ACC ACA GTG GCC CCC CAG CGG    1344
Ala Met Val Ala Leu Ala Gln Asn Trp Thr Thr Val Ala Pro Gln Arg
        435                 440                 445

AAG TGC ATC ATC GAC ATC CTC ACC GAG CCC AAA GAC ATC GGG AAA CGG    1392
Lys Cys Ile Ile Asp Ile Leu Thr Glu Pro Lys Asp Ile Gly Lys Arg
    450                 455                 460

CTC GAG GTG CGG AAG ACC GTG ACC GCG TGC CTG GGC GAG CCC AAC CAC    1440
Leu Glu Val Arg Lys Thr Val Thr Ala Cys Leu Gly Glu Pro Asn His
465                 470                 475                 480

ATC ACT CGG CTG GAG CAC GCT CAG GCG CGG CTC ACC CTG TCC TAT AAT    1488
Ile Thr Arg Leu Glu His Ala Gln Ala Arg Leu Thr Leu Ser Tyr Asn
                485                 490                 495

CGC CGT GGC GAC CTG GCC ATC CAC CTG GTC AGC CCC ATG GGC ACC CGC    1536
Arg Arg Gly Asp Leu Ala Ile His Leu Val Ser Pro Met Gly Thr Arg
            500                 505                 510

TCC ACC CTG CTG GCA GCC AGG CCA CAT GAC TAC TCC GCA GAT GGG TTT    1584
Ser Thr Leu Leu Ala Ala Arg Pro His Asp Tyr Ser Ala Asp Gly Phe
        515                 520                 525

AAT GAC TGG GCC TTC ATG ACA ACT CAT TCC TGG GAT GAG GAT CCC TCT    1632
Asn Asp Trp Ala Phe Met Thr Thr His Ser Trp Asp Glu Asp Pro Ser
    530                 535                 540

GGC GAG TGG GTC CTA GAG ATT GAA AAC ACC AGC GAA GCC AAC AAC TAT    1680
Gly Glu Trp Val Leu Glu Ile Glu Asn Thr Ser Glu Ala Asn Asn Tyr
545                 550                 555                 560

GGG ACG CTG ACC AAG TTC ACC CTC GTA CTC TAT GGC ACC GCC CCT GAG    1728
Gly Thr Leu Thr Lys Phe Thr Leu Val Leu Tyr Gly Thr Ala Pro Glu
                565                 570                 575

GGG CTG CCC GTA CCT CCA GAA AGC AGT GCA GCT GGT GGA GCT GCA CAT    1776
Gly Leu Pro Val Pro Pro Glu Ser Ser Ala Ala Gly Gly Ala Ala His
            580                 585                 590

CAT CAC CAT CAC CAC TAA                                            1794
His His His His His
        595

(2) INFORMATION FOR SEQ ID NO:21:

(i) SEQUENCE CHARACTERISTICS:
        (A) LENGTH: 597 amino acids
        (B) TYPE: amino acid
        (D) TOPOLOGY: linear (ii) MOLECULE TYPE: protein (xi) SEQUENCE DESCRIPTION: SEQ ID NO:21:

Met Glu Leu Arg Pro Trp Leu Leu Trp Val Val Ala Ala Thr Gly Thr
1               5                   10                  15

Leu Val Leu Leu Ala Ala Asp Ala Gln Gly Gln Lys Val Phe Thr Asn
            20                  25                  30

Thr Trp Ala Val Arg Ile Pro Gly Gly Pro Ala Val Ala Asn Ser Val
        35                  40                  45
```

-continued

```
Ala Arg Lys His Gly Phe Leu Asn Leu Gly Gln Ile Phe Gly Asp Tyr
    50                  55                  60

Tyr His Phe Trp His Arg Gly Val Thr Lys Arg Ser Leu Ser Pro His
65                  70                  75                  80

Arg Pro Arg His Ser Arg Leu Gln Arg Glu Pro Gln Val Gln Trp Leu
                85                  90                  95

Glu Gln Gln Val Ala Lys Arg Thr Lys Arg Asp Val Tyr Gln Glu
            100                 105                 110

Pro Thr Asp Pro Lys Phe Pro Gln Gln Trp Tyr Leu Ser Gly Val Thr
            115                 120                 125

Gln Arg Asp Leu Asn Val Lys Ala Ala Trp Ala Gln Gly Tyr Thr Gly
        130                 135                 140

His Gly Ile Val Val Ser Ile Leu Asp Asp Gly Ile Glu Lys Asn His
145                 150                 155                 160

Pro Asp Leu Ala Gly Asn Tyr Asp Pro Gly Ala Ser Phe Asp Val Asn
                165                 170                 175

Asp Gln Asp Pro Asp Pro Gln Pro Arg Tyr Thr Gln Met Asn Asp Asn
            180                 185                 190

Arg His Gly Thr Arg Cys Ala Gly Glu Val Ala Ala Val Ala Asn Asn
        195                 200                 205

Gly Val Cys Gly Val Gly Val Ala Tyr Asn Ala Arg Ile Gly Gly Val
210                 215                 220

Arg Met Leu Asp Gly Glu Val Thr Asp Ala Val Glu Ala Arg Ser Leu
225                 230                 235                 240

Gly Leu Asn Pro Asn His Ile His Ile Tyr Ser Ala Ser Trp Gly Pro
                245                 250                 255

Glu Asp Asp Gly Lys Thr Val Asp Gly Pro Ala Arg Leu Ala Glu Glu
            260                 265                 270

Ala Phe Phe Arg Gly Val Ser Gln Gly Arg Gly Gly Leu Gly Ser Ile
        275                 280                 285

Phe Val Trp Ala Ser Gly Asn Gly Gly Arg Glu His Asp Ser Cys Asn
290                 295                 300

Cys Asp Gly Tyr Thr Asn Ser Ile Tyr Thr Leu Ser Ile Ser Ser Ala
305                 310                 315                 320

Thr Gln Phe Gly Asn Val Pro Trp Tyr Ser Glu Ala Cys Ser Ser Thr
                325                 330                 335

Leu Ala Thr Thr Tyr Ser Ser Gly Asn Gln Asn Glu Lys Gln Ile Val
            340                 345                 350

Thr Thr Asp Leu Arg Gln Lys Cys Thr Glu Ser His Thr Gly Thr Ser
        355                 360                 365

Ala Ser Ala Pro Leu Ala Ala Gly Ile Ile Ala Leu Thr Leu Glu Ala
370                 375                 380

Asn Lys Asn Leu Thr Trp Arg Asp Met Gln His Leu Val Val Gln Thr
385                 390                 395                 400

Ser Lys Pro Ala His Leu Asn Ala Asn Asp Trp Ala Thr Asn Gly Val
                405                 410                 415

Gly Arg Lys Val Ser His Ser Tyr Gly Tyr Gly Leu Leu Asp Ala Gly
            420                 425                 430

Ala Met Val Ala Leu Ala Gln Asn Trp Thr Thr Val Ala Pro Gln Arg
        435                 440                 445

Lys Cys Ile Ile Asp Ile Leu Thr Glu Pro Lys Asp Ile Gly Lys Arg
450                 455                 460
```

```
Leu Glu Val Arg Lys Thr Val Thr Ala Cys Leu Gly Glu Pro Asn His
465                 470                 475                 480

Ile Thr Arg Leu Glu His Ala Gln Ala Arg Leu Thr Leu Ser Tyr Asn
            485                 490                 495

Arg Arg Gly Asp Leu Ala Ile His Leu Val Ser Pro Met Gly Thr Arg
            500                 505                 510

Ser Thr Leu Leu Ala Ala Arg Pro His Asp Tyr Ser Ala Asp Gly Phe
        515                 520                 525

Asn Asp Trp Ala Phe Met Thr Thr His Ser Trp Asp Glu Asp Pro Ser
        530                 535                 540

Gly Glu Trp Val Leu Glu Ile Glu Asn Thr Ser Glu Ala Asn Asn Tyr
545                 550                 555                 560

Gly Thr Leu Thr Lys Phe Thr Leu Val Leu Tyr Gly Thr Ala Pro Glu
            565                 570                 575

Gly Leu Pro Val Pro Pro Glu Ser Ser Ala Ala Gly Gly Ala Ala His
            580                 585                 590

His His His His His
        595

(2) INFORMATION FOR SEQ ID NO:22:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:22:

TGAGGGAGGT GGGGGAGGTC ATCACCACCA TCACCATCAT CATCACCATT            50

(2) INFORMATION FOR SEQ ID NO:23:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:23:

AATTAATGGT GATGATGATG GTGATGGTGG TGATGACCTC CCCCACCTCC C          51

(2) INFORMATION FOR SEQ ID NO:24:

(i) SEQUENCE CHARACTERISTICS:
        (A) LENGTH: 66 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:24:

GGACCCCTCT GGCGAGTGGG TCCTCGAGAT TGAAAACACC AGCGAAGCCA ACAACTATGG    60

GACGCT                                                              66

(2) INFORMATION FOR SEQ ID NO:25:

(i) SEQUENCE CHARACTERISTICS:
        (A) LENGTH: 69 base pairs
```

-continued (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:25:

TCAAGCGTCC CATAGTTGTT GGCTTCGCTG GTGTTTTCAA TCTCGAGGAC CCACTCGCCA      60

GAGGGGTCC                                                             69

(2) INFORMATION FOR SEQ ID NO:26:

(i) SEQUENCE CHARACTERISTICS:
            (A) LENGTH: 69 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:26:

TCAAGCGTCC CATAGTTGTT GGCTTCGCTG GTGTTTTCAA TCTCGAGGAC CCACTCGCCA      60

GAGGGGTCC                                                             69

(2) INFORMATION FOR SEQ ID NO:27:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:27:

ATTACAATTG CTGCAGGGAT CCAC                                            24

(2) INFORMATION FOR SEQ ID NO:28:

(i) SEQUENCE CHARACTERISTICS:
            (A) LENGTH: 6 amino acids
            (B) TYPE: amino acid
            (C) STRANDEDNESS: single
            (D) TOPOLOGY: linear (xi) SEQUENCE DESCRIPTION: SEQ ID NO:28:

Ala Ala Gly Gly Ala Ala
1               5

(2) INFORMATION FOR SEQ ID NO:29:

(i) SEQUENCE CHARACTERISTICS:
            (A) LENGTH: 4 amino acids
            (B) TYPE: amino acid
            (C) STRANDEDNESS: single
            (D) TOPOLOGY: linear (xi) SEQUENCE DESCRIPTION: SEQ ID NO:29:

Arg Val Arg Arg